US012637677B2

(12) United States Patent
Cruse

(10) Patent No.: US 12,637,677 B2
(45) Date of Patent: May 26, 2026

(54) EXON SKIPPING OF FC-EPSILON-RI-BETA AND MS4A6A IN COMBINATION FOR THE TREATMENT OF ALLERGIC DISEASES

(71) Applicant: North Carolina State University, Raleigh, NC (US)

(72) Inventor: Glenn P. Cruse, Apex, NC (US)

(73) Assignee: North Carolina State University, Raleigh, NC (US)

( * ) Notice: Subject to any disclaimer, the term of this patent is extended or adjusted under 35 U.S.C. 154(b) by 962 days.

(21) Appl. No.: 17/775,136

(22) PCT Filed: Nov. 9, 2020

(86) PCT No.: PCT/US2020/059682
§ 371 (c)(1),
(2) Date: May 6, 2022

(87) PCT Pub. No.: WO2021/092562
PCT Pub. Date: May 14, 2021

(65) Prior Publication Data
US 2022/0380777 A1     Dec. 1, 2022

Related U.S. Application Data

(60) Provisional application No. 62/932,664, filed on Nov. 8, 2019.

(51) Int. Cl.
*C12N 15/113*     (2010.01)
*C12Q 1/68*     (2018.01)

(52) U.S. Cl.
CPC ...... *C12N 15/1138* (2013.01); *C12N 2310/11* (2013.01); *C12N 2310/3233* (2013.01); *C12N 2320/31* (2013.01); *C12N 2320/33* (2013.01)

(58) Field of Classification Search
None
See application file for complete search history.

(56) References Cited

U.S. PATENT DOCUMENTS

| | | | |
|---|---|---|---|
| 5,989,849 | A | 11/1999 | Gewirtz et al. |
| 6,806,084 | B1 | 10/2004 | Debs et al. |
| 7,691,989 | B2 | 4/2010 | Genentech |
| 7,973,015 | B2 | 7/2011 | Van Ommen et al. |
| 8,236,557 | B2 | 8/2012 | Dongsheng et al. |
| 8,268,962 | B2 | 9/2012 | Heemskerk et al. |
| 8,304,398 | B2 | 11/2012 | 't Hoen et al. |
| 8,361,979 | B2 | 1/2013 | Aartsma-Rus et al. |
| 8,802,645 | B2 | 8/2014 | Van Ommen et al. |
| 9,080,170 | B2 | 7/2015 | Garcia et al. |
| 9,238,042 | B2 | 1/2016 | Schnell et al. |
| 9,598,703 | B2 | 3/2017 | Garcia et al. |
| 9,738,891 | B2 | 8/2017 | Leumann et al. |
| 9,862,945 | B2 | 1/2018 | Flanigan et al. |
| 10,030,894 | B2 | 7/2018 | Azuma et al. |
| 10,188,633 | B2 | 1/2019 | Nelson et al. |
| 10,590,420 | B2 | 3/2020 | Barkats et al. |
| 11,268,096 | B2 | 3/2022 | Cruse et al. |
| 11,279,934 | B2 | 3/2022 | Byrne et al. |
| 2008/0200409 | A1 | 8/2008 | Wilson et al. |
| 2011/0039334 | A1 | 2/2011 | Bennett et al. |
| 2012/0029059 | A1 | 2/2012 | Wilton et al. |
| 2013/0253033 | A1 | 9/2013 | Wilton et al. |
| 2016/0040120 | A1 | 2/2016 | Gottwald et al. |
| 2019/0062756 | A1 | 2/2019 | Cruse et al. |
| 2019/0317099 | A1 | 10/2019 | Halbert |
| 2021/0363531 | A1 | 11/2021 | Cruse |
| 2022/0372492 | A1 | 11/2022 | Cruse et al. |

FOREIGN PATENT DOCUMENTS

| | | |
|---|---|---|
| EP | 3 844 278 | 7/2021 |
| WO | WO 2005/080410 | 9/2005 |
| WO | WO 2005/085443 | 9/2005 |
| WO | WO 2007/028065 | 3/2007 |
| WO | WO 2017/136435 A1 | 8/2017 |
| WO | WO 2019/200383 A1 | 10/2019 |
| WO | WO 2020/046985 | 3/2020 |

OTHER PUBLICATIONS

Bitting et al., Allergy vol. 78:1204-1217, 2023.*
Office Action corresponding to Chinese Application No. 202080092446.5 dated Jun. 1, 2023.
Office Action corresponding to Canadian Application No. 3,110,353 dated Sep. 12, 2023.
Aartsma-Rus et al., "Guidelines for Antisense Oligonucleotide Design and Insight Into Splice-modulating Mechanisms". (Mol. Ther. 17(3): 548-553, 2009).
Aartsma-Rus et al., "Targeted exon skipping as a potential gene correction therapy for Duchenne muscular dystrophy". (Neuromuscular Disorders 12: S71-S77, 2002).
Advisory Action corresponding to U.S. Appl. No. 16/052,130 dated Oct. 9, 2020.
Alshahrani et al., "CEACAM2 negatively regulates hemi (ITAM-bearing) GPVI and CLEC-2 pathways and thrombus growth in vitro and in vivo". Blood, vol. 124, pp. 2431-2441 (2014).
Antonescu et al. (2005) "Acquired Resistance to Imatinib in Gastrointestinal Stromal Tumor Occurs Through Secondary Gene Mutation". Clin Cancer Res 11(11): 4182-4190.

(Continued)

*Primary Examiner* — Sean McGarry
(74) *Attorney, Agent, or Firm* — Jenkins, Taylor & Hunt, P.A.

(57) ABSTRACT

Compositions and methods for treating diseases and conditions mediated by the high affinity IgE receptor (FcεRI) are provided. Also provided are antisense oligomers for modulating splicing of mRNA encoding a MS4A6A protein, optionally in addition to antisense oligomers for modulating splicing of mRNA encoding the FcεRIβ protein, thereby down-regulating cell-surface expression of FcεRI, and uses of the antisense oligomers for inhibiting mast cell degranulation, cytokine release, migration, and proliferation; for inhibiting anaphylaxis reactions in individuals, for treating allergic conditions in individuals, for reducing the incidence of allergic reactions in individuals, for treating individuals at risk of developing anaphylactic reactions, and for treating mast cell-related diseases in individuals.

17 Claims, 15 Drawing Sheets
Specification includes a Sequence Listing.

(56)                    References Cited

OTHER PUBLICATIONS

Arechavala-Gomeza et al., Comparative Analysis of Antisense Oligonucleotide Sequences for Targeted Skipping of Exon 51 During Dystrophin Pre-mRNA Splicing in Human Muscle. (Hum. Gene Ther. Sep. 2007;18(9):798-810).

Arock et al. (2015) "KIT mutation analysis in mast cell neoplasms: recommendations of the European Competence Network on Mastocytosis". Leukemia 29(6): 1223-1232.

Asai et al. (2001) "Regulation of Mast Cell Survival by IgE". Immunity 14(6): 791-800.

Besmer et al. "A new acute transforming feline retrovirus and relationship of its oncogene v-kit with the protein kinase gene family". (1986) Nature 320(6061): 415-421.

Cruse et al. (2011) "Functional KCa3.1 K+ channels are required for human fibrocyte migration". J. Allergy and Clin. Immun. 128:1303-09.

Cruse et al. (2013) "A truncated splice-variant of the FcεRIβ receptor subunit is critical for microtubule formation and degranulation in mast cells". Immunity 38(5): 906-917.

Cruse et al. (2014) "Functional deregulation of kit: link to mast cell proliferative diseases and other neoplasms". Immunol Allergy Clin North Am 34(2): 219-237.

Cruse et al. A novel FcεRIβ-chain truncation regulates human mast cell proliferation and survival. Faseb J., Oct. 2010; 24(10):4047-4057.

Cruse et al. Functional KCa3.1 K+ channels are required for human lung mast cell migration, Thorax 61:880-85 (2006).

Cruse et al., "Exon skipping of FcεERIβ eliminates expression of the high-affinity 1gE receptor in mast cells with therapeutic potential for allergy," Proc Natl Acad Scie USA pp. 14115-14120 (2016).

Cruse et al., "Mast cells in airway diseases and interstitial lung disease". European Journal of Pharmacology, vol. 778, pp. 125-138 (2016).

Cruse et al., "The CD20 homologue MS4A4 directs trafficking of KIT toward clathrin-independent endocytosis pathways and thus regulates receptor signaling and recycling". Mol Biol Cell, vol. 26, pp. 1711-1727 (2015).

Dalerba et al., "Single-cell dissection of transcriptional heterogeneity in human colon tumors". Nat Biotechnol, vol. 29, pp. 1120-1127 (2011).

De Angelis et al., "Chimeric snRNA molecules carrying antisense sequences against the splice junctions of exon 51 of the dystrophin pre-mRNA induce exon skipping and restoration of a dystrophin synthesis in Delta 48-50 DMD cells". Proc Natl Acad Sci USA, vol. 99, pp. 9456-9461 (2002).

Dehlink et al., "Relationships between levels of serum IgE, cell-bound IgE, and IgE-receptors on peripheral blood cells in a pediatric population". PLoS One, vol. 5, Article ID e12204 (2010).

Denti et al., "Chimeric adeno-associated virus/antisense U1 small nuclear RNA effectively rescues dystrophin synthesis and muscle function by local treatment of mdx mice". Hum Gene Ther, vol. 17, pp. 565-574 (2006).

Disterer et al. (2013) "Exon Skipping of Hepatic APOB Pre-mRNA With Splice-switching Oligonucleotides Reduces LDL Cholesterol In Vivo". Mol Ther 21(3): 602-609.

Dombrowicz et al., "Allergy-associated FcRβ is a molecular amplifier of IgE-and IgG-mediated in vivo responses". Immunity, vol. 8, pp. 517-529 (1998).

Dombrowicz et al., "Anaphylaxis mediated through a humanized high affinity IgE receptor". J Immunol, vol. 157, pp. 1645-1651 (1996).

Donnadieu et al., "A second amplifier function for the allergy-associated FcεRI-β subunit". Immunity, vol. 12, pp. 515-523 (2000).

Dowling (2016) "Eteplirsen therapy for Duchenne muscular dystrophy: skipping to the front of the line". Nat Rev Neurol 12(12): 675-676.

Extended European Search Report corresponding to European Patent Application No. 19853725.0 dated Apr. 25, 2022.

Gazzoli Isabella et al: "Splice-Switching Oligonucleotides" In: "Oligonucleotide-Based Drugs and Therapeutics: Preclinical and Clinical Considerations for Development", pp. 445-489 (Jun. 15, 2018).

Godfrey et al. (2017) "Delivery is key: lessons learnt from developing splice-switching antisense therapies". EMBO Mol Med 9(5): 545-557.

Goyenvalle et al., "Rescue of dystrophic muscle through U7 snRNA—mediated exon skipping". Science, vol. 306, pp. 1796-1799 (2004).

International Preliminary Report on Patentability corresponding to International Patent Application No. PCT/US 2020/059682 dated May 19, 2022.

International Preliminary Report on Patentability corresponding to International Patent Application No. PCT/US2017/016042 dated Aug. 7, 2018.

International Preliminary Report on Patentability corresponding to International Patent Application No. PCT/US2019/048400 dated Mar. 2, 2021.

International Search Report and Written Opinion of the International Searching Authority corresponding to International Patent Application No. PCT/US2020/59682 dated Mar. 29, 2021.

International Search Report corresponding to International Patent Application No. PCT/US2017/016042 dated Apr. 25, 2017.

International Search Report corresponding to International Patent Application No. PCT/US2019/048400 dated Dec. 12, 2019.

Juliano (2016) "The delivery of therapeutic oligonucleotides". Nucleic Acids Res 44(14): 6518-6548.

Notice of Allowance of Allowance corresponding to U.S. Appl. No. 16/052,130 dated Nov. 1, 2021.

Notice of Allowance of Allowance corresponding to U.S. Appl. No. 16/052,130 dated Jul. 14, 2021.

Notice of Publication corresponding to International application No. PCT/US2020/059682 dated May 14, 2021.

Notice of Publication corresponding to International application No. PCT/US2017/016042 dated Aug. 10, 2017.

Notice of Publication corresponding to International application No. PCT/US2019/048400 dated Mar. 5, 2020.

Notice of Publication corresponding to European Application No. 20885567.6-1112 dated Aug. 18, 2022.

Notice of Publication corresponding to European Application No. 19853725.0-1111 dated Jun. 9, 2021.

Office Action corresponding to U.S. Appl. No. 16/052,130 dated Dec. 24, 2020.

Office Action corresponding to U.S. Appl. No. 16/052,130 dated Jun. 23, 2020.

Office Action corresponding to U.S. Appl. No. 16/052,130 dated Nov. 29, 2019.

Written Opinion of the International Searching Authority corresponding to International Patent Application No. PCT/US2017/016042 dated Aug. 10, 2017.

Written Opinion of the International Searching Authority corresponding to International Patent Application No. PCT/US2019/048400 dated Nov. 21, 2019.

Liang et al. (2001) Structural Organization of the Human MS4A Gene Cluster on Chromosome 11q12. Immunogenetics 53:357-368.

Office Action corresponding to Chinese Application No. 202080092446.5 dated Feb. 5, 2024.

* cited by examiner

SEQUENCE LISTING

```
<160> NUMBER OF SEQ ID NOS: 26

<210> SEQ ID NO 1
<211> LENGTH: 1791
<212> TYPE: DNA
<213> ORGANISM: Homo sapiens
<220> FEATURE:
<221> NAME/KEY: CDS
<222> LOCATION: (494)..(1240)

<400> SEQUENCE: 1
attccgaagg gttctgtgct aggaacctta cacgtgttgt ctcacataat ccttaaaact        60
cagaaatgat tttaaattaa atagcacaga gaggaaaact gactggagag ggagcctttg       120
cttagattag aaaactgaag cttcaagaac agacttgcct aacaacagga aacttgtatg       180
tctcgaagtg gcaattcaca cataaggctc catgactcct gaactctcac aaatattagt       240
tggctctttt catggtttta ctgaagttgc tagaagttta cagaaaagga agtgcaggaa       300
catttcacaa atctacaatc tgtgagtatc acatcctgta tagctgtaaa cactggaata       360
aggaagggct gatgactttc agaagatgaa ggtaagtaga aaccgttgat gggactgaga       420
aaccagagtt aaaacctctt tggagcttct gaggactcag ctggaaccaa cgggcacagt       480
tggcaacacc atc atg aca tca caa cct gtt ccc aat gag acc atc ata        529
            Met Thr Ser Gln Pro Val Pro Asn Glu Thr Ile Ile
             1               5                  10 gtg ctc cca tca aat gtc atc aac ttc tcc caa gca gag aaa ccc gaa        577
Val Leu Pro Ser Asn Val Ile Asn Phe Ser Gln Ala Glu Lys Pro Glu
         15                  20                  25 ccc acc aac cag ggg cag gat agc ctg aag aaa cat cta cac gca gaa        625
```

-continued

```
Pro Thr Asn Gln Gly Gln Asp Ser Leu Lys Lys His Leu His Ala Glu
    30                  35                  40 atc aaa gtt att ggg act atc cag atc ttg tgt ggc atg atg gta ttg        673
Ile Lys Val Ile Gly Thr Ile Gln Ile Leu Cys Gly Met Met Val Leu
45                  50                  55                  60 agc ttg ggg atc att ttg gca tct gct tcc ttc tct cca aat ttt acc        721
Ser Leu Gly Ile Ile Leu Ala Ser Ala Ser Phe Ser Pro Asn Phe Thr
                    65                  70                  75 caa gtg act tct aca ctg ttg aac tct gct tac cca ttc ata gga ccc        769
Gln Val Thr Ser Thr Leu Leu Asn Ser Ala Tyr Pro Phe Ile Gly Pro
                80                  85                  90 ttt ttt ttt atc atc tct ggc tct cta tca atc gcc aca gag aaa agg        817
Phe Phe Phe Ile Ile Ser Gly Ser Leu Ser Ile Ala Thr Glu Lys Arg
            95                  100                 105 tta acc aag ctt ttg gtg cat agc agc ctg gtt gga agc att ctg agt        865
Leu Thr Lys Leu Leu Val His Ser Ser Leu Val Gly Ser Ile Leu Ser
        110                 115                 120 gct ctg tct gcc ctg gtg ggt ttc att atc ctg tct gtc aaa cag gcc        913
Ala Leu Ser Ala Leu Val Gly Phe Ile Ile Leu Ser Val Lys Gln Ala
125                 130                 135                 140 acc tta aat cct gcc tca ctg cag tgt gag ttg gac aaa aat aat ata        961
Thr Leu Asn Pro Ala Ser Leu Gln Cys Glu Leu Asp Lys Asn Asn Ile
                145                 150                 155 cca aca aga agt tat gtt tct tac ttt tat cat gat tca ctt tat acc       1009
Pro Thr Arg Ser Tyr Val Ser Tyr Phe Tyr His Asp Ser Leu Tyr Thr
                160                 165                 170 acg gac tgc tat aca gcc aaa gcc agt ctg gct gga act ctc tct ctg       1057
Thr Asp Cys Tyr Thr Ala Lys Ala Ser Leu Ala Gly Thr Leu Ser Leu
            175                 180                 185 atg ctg att tgc act ctg ctg gaa ttc tgc cta gct gtg ctc act gct       1105
Met Leu Ile Cys Thr Leu Leu Glu Phe Cys Leu Ala Val Leu Thr Ala
        190                 195                 200 gtg ctg cgg tgg aaa cag gct tac tct gac ttc cct ggg agt gta ctt       1153
Val Leu Arg Trp Lys Gln Ala Tyr Ser Asp Phe Pro Gly Ser Val Leu
205                 210                 215                 220 ttc ctg cct cac agt tac att ggt aat tct ggc atg tcc tca aaa atg       1201
Phe Leu Pro His Ser Tyr Ile Gly Asn Ser Gly Met Ser Ser Lys Met
                225                 230                 235 act cat gac tgt gga tat gaa gaa cta ttg act tct taa gaaaaaggg         1250
Thr His Asp Cys Gly Tyr Glu Glu Leu Leu Thr Ser
                240                 245 agaaatatta atcagaaagt tgattcttat gataatatgg aaaagttaac cattatagaa     1310
aagcaaagct tgagtttcct aaatgtaagc ttttaaagta atgaacatta aaaaaaacca     1370
ttatttcact gtcatttaag atatgtgttc attggggatc tcttgatttg cctgacattg     1430
acttcagcaa aagcacgggg ctgtaaatta ccatttacta gattagccaa atagtctgaa     1490
tttccagaaa acaaggcaga atgatcattc ccagaaacat ttcccagaaa atgtttccca     1550
gaaaactaga cagaatgatc attcaatgga tcacagtgaa gcaaggaca caacttttta      1610 ttgtacccct taattgtcaa caggagttaa ctgatttgtt gtggtgctca gactttttta     1670
tacaggtgct agtgttttat cctatgtatt ttaactcatt agtgcataaa ggcaagcccc     1730
atataatgaa gtctcagggt atatgaaagt agctggcttc aaaataaaat ttttgagtgc     1790
a                                                                     1791

<210> SEQ ID NO 2
<211> LENGTH: 248
<212> TYPE: PRT
```

-continued

```
<213> ORGANISM: Homo sapiens

<400> SEQUENCE: 2

Met Thr Ser Gln Pro Val Pro Asn Glu Thr Ile Ile Val Leu Pro Ser
1               5                   10                  15

Asn Val Ile Asn Phe Ser Gln Ala Glu Lys Pro Glu Pro Thr Asn Gln
                20                  25                  30

Gly Gln Asp Ser Leu Lys Lys His Leu His Ala Glu Ile Lys Val Ile
            35                  40                  45

Gly Thr Ile Gln Ile Leu Cys Gly Met Met Val Leu Ser Leu Gly Ile
        50                  55                  60

Ile Leu Ala Ser Ala Ser Phe Ser Pro Asn Phe Thr Gln Val Thr Ser
65                  70                  75                  80

Thr Leu Leu Asn Ser Ala Tyr Pro Phe Ile Gly Pro Phe Phe Phe Ile
                85                  90                  95

Ile Ser Gly Ser Leu Ser Ile Ala Thr Glu Lys Arg Leu Thr Lys Leu
            100                 105                 110

Leu Val His Ser Ser Leu Val Gly Ser Ile Leu Ser Ala Leu Ser Ala
        115                 120                 125

Leu Val Gly Phe Ile Ile Leu Ser Val Lys Gln Ala Thr Leu Asn Pro
    130                 135                 140

Ala Ser Leu Gln Cys Glu Leu Asp Lys Asn Asn Ile Pro Thr Arg Ser
145                 150                 155                 160

Tyr Val Ser Tyr Phe Tyr His Asp Ser Leu Tyr Thr Thr Asp Cys Tyr
                165                 170                 175

Thr Ala Lys Ala Ser Leu Ala Gly Thr Leu Ser Leu Met Leu Ile Cys
            180                 185                 190

Thr Leu Leu Glu Phe Cys Leu Ala Val Leu Thr Ala Val Leu Arg Trp
        195                 200                 205

Lys Gln Ala Tyr Ser Asp Phe Pro Gly Ser Val Leu Phe Leu Pro His
    210                 215                 220

Ser Tyr Ile Gly Asn Ser Gly Met Ser Ser Lys Met Thr His Asp Cys
225                 230                 235                 240

Gly Tyr Glu Glu Leu Leu Thr Ser
                245

<210> SEQ ID NO 3
<211> LENGTH: 13060
<212> TYPE: DNA
<213> ORGANISM: Homo sapiens

<400> SEQUENCE: 3
attccgaagg gttctgtgct aggaacctta cacgtgttgt ctcacataat ccttaaaact        60
cagaaatgat tttaaattaa atagcacaga gaggaaaact gactggagag ggagcctttg       120
cttaggtagg caactttaac tggtttatta gcacattccc ctgaagggaa agggggtgtg       180
attgctcctg aagagaccaa agagactggg ctccttttta atcaaagctc aggaggagag       240
ctgcattcca ctgtttcaca gatgctgtga gggtgacaaa gatgcagggc acccactgga       300
aacacagacg gcactctgcg aaagaggaag gggcgccagg agcttgggtg agcaaggttg       360
gaggtgattc tgcccctctc cccaggcttt ctgtgtgagt ccattcctcc tctcagattt       420
attgttagaa cttaagacaa gccaattaca tttcataatg tctgtgtcat tcagacgctg       480
agaactaatc cagccttcta aatggtgctt cttaactcct ttcttcaaca ggagagttaa       540
tgtgtggaat taagtgcaga atccatggcc ctctgtggtg acggtgatgg ttcaggttgt       600
```

-continued

```
gtttctgggt tcattctgga agctccccca aggaaaggag gaaggaagct tgcagggtgg      660
ggctttgcca ttgccctgac tggctctggt ttccttgcct gatacattga agtcagcttc      720
caaagaatgc cacccaaggt tttgaagggg cacagtgcct ctgtcctcac aaaaccagcc      780
tgcatatgag tttactgaat tcatttaggt cctgctgaat cttttcccatt tgttccttct      840 ctgtttcaat atttcaatgc ttccctggag gggcccaacc tttctggagg gcaaagatct      900
gttgttagag aaaaagagca gccagaggag gaagatgact tgagggtagg cagcagttgg      960
gcaatcagta ttgaaaggtt gctttcagcc tgccaagact tggggaatta gaaaagcaag     1020
ataaaacaaa acaaacaaac aaactatata tataaaaaac aattttttaa aagttttttt     1080
atgttctata ttactattag ctatatatta atgaatgttc ctttaaagca gtgtagtcat     1140
tattgctatt attattatta tggttagtta tagacagtgg aatattgttc tttctctata     1200
ttatgattac tagcactatt actgttatta gttacatgtt attgaaagct tcaaagcagc     1260
ataggctttt tataaatatt tttgctcatc tttatgacaa ttctccagtg ttggtattgc     1320
tcctctattt aacagattag aaaactgaag cttcaagaac agacttgcct aacaacagga     1380
aacttgtatg tctcgaagtg gcaattcaca cataaggctc catgactcct gaactctcac     1440
aaatattagt tggctctttt catggtttta ctgaagttgc tagaagttta cagaaaagga     1500
agtgcaggaa catttcacaa atctacaatc tgtgagtatc acatcctgta tagctgtaaa     1560
cactggaata aggaagggct gatgactttc agaagatgaa ggtaagtaga aaccgttgat     1620
gggactgaga aaccagagtt aaaacctctt tggagcttct gaggactcag ctggaaccaa     1680
cgggcacagg taggtaatgc tggaagactt ttctcatctc actattccct tgccgtgacc     1740
tcattagagg agtaatttaa cttgaaactc cttgacagca gttaagagac actagggcct     1800
tttggaaata gagtgggcaa atggaaggag tatctgtttt taactctgtg tccgctgtat     1860
tctaattgca taaactcagt gagtcactta cctaaggttg tgtaattaat gggagcagag     1920
ctcttgtctc ttcaaatgtg tttagaccat ttgtaaactg ggcggtctgt gctttgagaa     1980
tggtgccgtg aaaagggatc caagctgagc ttagcaacaa ataccacaac ctacttggtc     2040
tttatgctaa aaagtgggga ggaccaacga cgcgagccta tgtgttatga gtccaagact     2100
tgttctcata ccactgcatg cagctgtttc tccagcctga gtaaactcag acacaggctg     2160
gcaatgccag gtgggaaatt aggaagaggt agaatgatct agagatttat gcaaaggctt     2220
cagactccag gaaagctgag atccaagact ggttttacag cttcccggct gtgtgaacca     2280
gggtgaacaa taagggtaac tgcaaatatt tcttcagcat taactctggg ccacacatat     2340
atgcaatagg tatattattt gcattcataa cttaaacttt attttgcatt ttcttattta     2400
ttacatgttt ttactaactt actaacatgc agagctgttg taaggattaa aagcactgca     2460
gggtaaaaat taagaatgtg tctggtaaaa tatgataaac atatctgagt gctaataaat     2520
agtattatta aacaagaaat aagtaagcag agttcattta ttagtctgaa aattcatcaa     2580
atatatggca atacagttgt tgtcagtagg actagaggaa agggaggttg ttgcatattg     2640
caaattttgt gtgaccattt gcctctggac attgagacct ctcaagattc atgttgctgc     2700
caccctgtga tgtgtttatt atctataatg gactgtgtca aacattatgg aaaaatcctc     2760
atgaaaccaa gattgtgtgg ttttcactgt tccatactat cagtttcttt ctctaatgga     2820
caggccaagc ctagactaat tggcaaagac tgagttactg ttttttggagt cagaacctgg     2880 gagctctgta cttttttaaga gctaaatcta tttttttctta catagttggc aacaccatca     2940
```

-continued

```
tgacatcaca acctgttccc aatgagacca tcatagtgct cccatcaaat gtcatcaact    3000
tctcccaagc agagaaaccc gaacccacca accaggggca ggatagcctg aagaaacatc    3060
tacacgcaga aatcaaagtt attggggtaa atctaattca gaacgtgttg gagaggggtt    3120
gggggaagtg ccaagagatg atatatgtct tgggactgga catctgtcgt gagtgtggag    3180
accctaaaat tttgctagag ggactttagg gtagaagcca cttggagaaa actgtcccag    3240
aacttttcca caagaggttg tcttaaaaat atattttccc ttattctgaa tatgaggaat    3300
tgattttcta ttgttgtctt tgtattttta caatacagtg cttttctata ttttctttta    3360
caaaagtaat ggtggtaaat aatgacatat tgtgtgtatg tgtatatatt ccacaactgc    3420
atgcttaata atccaaactg acttttttgca aataattttt ccctcactgc aaattagagg    3480
aaatatacaa ctcctttccc tcttttctcc taacgttttt gagaatggaa atgatattca    3540
ccttttgttt gtctgtttct cctctcaccc agaatttatt aaagaagctg tattgcatga    3600
agggaggaga gaaagaaggg atctatcttg gattgggagg gaaacacaga gttttggttt    3660
ctagaattgc ctctgcactt atgtgatctg aggtgaggca ctctgtttga ctggatttca    3720
ggacctggtg ggactggttt ccttgcctca tgtacaatca catgggtttc tatgaggctc    3780
atgtgacata aggtctagaa aactttttgg taaatgataa tagagctgtg aatctctgag    3840
gtggatgtca ggaaggaaaa ctacctccta agacagagct tcagttatac atgagaacat    3900
gcagtatttg gtttctgtcc ctgtgttagt ctgctaaggg ggatggcctc taaatgatga    3960
gaacacatgg acacgtagaa cagaacaatg cacactgagg cctttcagag ggtggagggt    4020
gggaggagag agaggatcag gaaaaataac taatggatac taggcttaat acctgggtga    4080
tgaaataatc tgtacagcaa accccccatga cacaagttta tctatgtaac agacatgcag    4140 ttgtacccctt gaacttaaaa taaaagctaa aaataaaaga gcttccagag cttcagctat    4200
agggttgtga actgcagttt ccgaggaagt gaccaaaggg gcaaactcca tgtccagtgg    4260
agtctgggag atgaggggag ggccttctgc actgccaata ctgcagagaa tgtgggggct    4320
ttcagatgtc ccctgttttc agagagatag aaagagagtt aactagtcat ggacttagag    4380
gtcctgagag ctgggaaagt aaatctcagc acttgctgtg agctggaagc aagtctcatg    4440
agcagaccag ggcctgagag gcagaaatgc agaagccttc ctgagcacct gccagacacc    4500
tgagactgtg gcttctgtgg cagagctgca caccctccag gatgtctttt catatttctc    4560
actccagagt ttccacaggg tttgtatcct cattaggatc ttgcagaagg cgataatgca    4620
ttagtgccat gggagcggca aaaaggccct gtctttacaa atgctggttt tcatcctcaa    4680
tctcactttc tcttcccaca gactatccag atcttgtgtg gcatgatggt attgagcttg    4740
gggatcattt tggcatctgc ttccttctct ccaaatttta cccaagtgac ttctacactg    4800
ttgaactctg cttacccatt cataggaccc ttttttgtga gtagagtttc tgaggagggc    4860 aggatgggc aaagagggga ggaagatgcc aatagcttag acttcccacc tgccagcttg    4920
ctatgtttga tctgccagga gcaaggagtc aacggtgaat cttgttctcc tgtcgggtag    4980
gatgacaggg gttgcttgat tttagatcaa tttcttatca gactcaaata aacatttctt    5040
ttgaagatca tcttattctt cacattatca tcttgagcta tgatgaagct agtgacttct    5100
ctccaggttt aggcgaaaaa aaaatccatg aattaggata aagttgggaa ggaacatttt    5160
atacaaaaaa aaaaaagagc ataaatggaa gacatcacac actcacagag aaaccacact    5220
gttatccccc ccatgcttgt ggggatcatg gaggaaggag aacttacacc tctgagcatt    5280
ttgaaaatac ttttactgca ttgactgatt cccaggtaag gctgagcaga tatctatgcc    5340
```

-continued

```
cagtgattga caggaaattc ctctgaaata gctgcaagtc tggagtttca aaaggactta    5400
gtagtccttt cctcagagaa ctgctttctc taagatgggg gctttctcat aggtaagttt    5460 cccctttcata gatgtttttt ccttcaactt cctgcaattc agtagctatt tgttttctt     5520 acatttgtgt atttgatgca ccaagaagtc cacctttttg tgtatcttgt ccatttttct    5580
tgtcttatta actaaagtta cacttggatt tggatttcat tggtttttccc caaatgacct   5640 ttttctgttc caagatccat gccaagctac tacattacac tacattacat tttgtcatga    5700
tgtctcctca gggtcctcta ggctgtctaa gattttcctt ttccttgaga actttgatag    5760
ttttgggtag cgctggctga gatttttata gaatgttcct aaatttgggt ttgtctgatt    5820 ttttttttttg atgtttagag tatggtgatg aatttttggg tggtgatgat gaggtaaagc   5880 accatttca tcaagtcgta tcaagggtca tgctaccaac ataatgtcac tgacacaatt     5940
aaccttgatt atgtggttgg ggtagtattt tccagatttc tcctctgtaa aattactact   6000 tttttttttta accattgctt ttatgtcctt ccctagagaa catcttacac caaaactgtc   6060
tcattttatt aaaaaaacaa aaattatttc ctggcttta aggtcttttt ttgtttagtg     6120
ggatattttt tgtttattag gatatatttc tgctatcttt ttttttttctg atgttatctg   6180 aatgttatat ggacaaaggg acaaatctat gtatttaaat ggaacttacc tcattgatca    6240
ctggtttctc agggattttc ccatgagagt tgtctataaa cattgtgata gtgacgtcga   6300
aggtactctg tacatggaat ctgacctgac cattttctct tttatcttag tttatcatct   6360
ctggctctct atcaatcgcc acagagaaaa ggttaaccaa gcttttggtg agtaagagag    6420
ctataaccca caacccaatg gatcaaaata aaacttagac agaactcttt aaggctagtc   6480
tttctacttt gaaaagttga aaactcagtt ccagagcagt tggttgttgt tagaattagg   6540
agctgggcct ggatcctctg tatccttgtt cagagaacat ttctccaatt attgtaccct    6600
acatcaaagt ctgcattcag gggattataa tattccctct gcccatgccg aagaatgtat   6660
cacagagaaa ttgtgcctgt ttatgaggtt ctttcggtga taactggcct tcaaattcag    6720
gttttcagtg gcaaggaagc tgacagtgtt ataaagcggt ctattggttg gggtccattc   6780
tttaagccca ggtgttacaa cccttgaaaa aaaaatgagt caaagtgttg ttcatgtgag   6840
gtatccaaag tagacacaga ggctactaca gtatactaca ttacatttag gcctgatgtc    6900
tcctcaggtt cctttagact ttctcagatt ttccttttcc ttgaggactt caatagtttt   6960
gggtagtgct ggctgactgt atcctttcat ctatctcacc agaagtataa tacttttatt    7020
ttgtttgagt ataaattctt gcaccctaaa aagttgtcct tagtcatttg tattggctaa   7080
caaaaaaaca aaacaacaac aacaaaaaac aaagctttac ccgtctttat cccttattcc    7140
agcaaaaact agagttggaa gtggcaggga gacaaagcct ggattatagg gagaatcttc    7200
tcttgtcttt aaagtttcat taagtcttcg ctcaatccat tatctctcaa ggggttgatg   7260
ttggagatta tgtgagagaa tgtcatacca tgcaattgca ccgagactca atttggaagc    7320
tctggctaca aaaatctccc aaagccagca aggaagtgag aaacggcatc cagaaaaatg   7380
ccaattcttt ttctcatcgg tatttagaga ttattatttg gaaccctcag ttagactcgg   7440
aactactaac tagatctgtg ctgtttaatt taacttctt tgaggatgga aatgaaatgt     7500
aactttctat gatgatagaa atgaaatgta actttctatg atgatggaaa tgcactacag   7560
ctgtactgta caatatggca gtcacatgtg gctatcgatg atgtgaaata tagtgcaact   7620
gaataaaaat ttctcttaat tttactttaa atatagatag tctatgtggc tattggcaac    7680
```

-continued

```
catactgagt agcctggcac aagggtagtg ctttcaaact tttaggagga aatatatggg   7740
cctgttactc cagagaacaa tcccacagtg aacatgcagg aagctcaagg atgcaggatg   7800
tggtctcggg gtgggctcag acttaccaga gacatcgagg ctttagcgag ttctactctt   7860
gtcacacatt gcaccagccc tttttgagat tgaagaagag tgccatctca agacaaatct   7920
agcttattct aagaaatata gactctaggc atcaagaata ctactggcta ctaggaggcc   7980
caggagtgta cacttcagtc attatgttgg gaaattgggg tcccagagta tcaactggtg   8040
agttcctaaa agaagaagtg cccatgtggg attaagtaac attctactgt atggctgtga   8100
ggtgtgccct ggagcctacc tacctgtaac tatagctctc agagtactct tagctcaatt   8160 ctctttctg tgtgagttgg agtacaaaag aagtcacttc tgaggttagt ttatctattc     8220
ccttcacttc ataaatgtat aaatgagaac cagagtggga aataaaatca aggaactgat   8280
tacccaaggg aataaaccaa ggcaagtcta gtactgtgac ttcaatattc tgacctccag   8340
ttcagacctt tttcttgtac ttcccgctgc ctcccacaca ttacaccatc cttgggcctg   8400
cacctagacc tctgcccaca gccaccccat actgcactca gtgtggccaa tcatatgcct   8460
gcccatgttc cagggcctgc ctgagactca gaaccacccc ctcactcatc tttgagaggt   8520 gtgctttga gagaagcaat gggcaggcga gagtgagcta ttaggttggt gcaaacataa      8580
ttgtggtttt atggcaaaaa ccacaattac ttttgcacca tgctaataca tgatctatct   8640
tttccatgtg gctgatgctt ccgccagggg ttttttgagtt gagcgagaga gaaactgcat  8700
ctggtacgtt gccaccttca ctttgggtca cgctctcttg gtaatgttgc aggtaaagcc   8760
tcatgaaagc cctgctatct gtcctgggga aagaatttag gagagtaaca ttctctacca   8820
caccactgag gtcctgctta aggtgaacca gttcgtatag tcattcattc agccaagaat   8880
taccctggag attgagagat ttttgctgga cactggagag gcatacagca ataaatgatc    8940
aatcccagac ctcctgaggg gacagataag ggaataactt acaatttaat ggcaaagatg   9000
cataacagat tcatgagtca ttagcaatga tccttaccca acatttctct ttcaggtgca    9060
tagcagcctg gttggaagca ttctgagtgc tctgtctgcc ctggtgggtt tcattatcct   9120
gtctgtcaaa caggccacct taaatcctgc ctcactgcag tgtgagttgg acaaaaataa    9180
tataccaaca agaagttatg tttcttactt ttatcatgat tcactttata ccacggactg   9240
ctatacagcc aaagccagtc tggctgtaag tattttaga tgggatgttc taatcttatg     9300
aggtattcaa aagccttgat ttcttgttat tccttctttt gaaaatctct ctattggttc    9360
tggtttgggc atctggggga aagccaggtt tatgtaaatc aaaggggact acagggatga    9420
gattaagggg attacatact aatagagtgg aattgaaaat gttaaataag gttgatgatg    9480
aaaaactaaa acttactgtt tgtagaggtt cttaattatc aaactaatcc aattttggag    9540
gcataaatta tgagtttatc aaaatgagaa tcttggtaca tggagtggtg aattaagaat    9600
ggaaacagag cagaaagacc caggagatca gaataggcca acaaggaaac agtatgtgtg    9660
catggtaagg agttaatttg gtttgagaag acatcagatt cagtactaag aaaaagagga    9720
taggaaatat gggatgagaa gataagggct tcttcttcta atgatcacaa taatgaataa    9780
tactgatcag gtgagaatgc aacattattg ttgcttttg ttatagctga aagaagtgtg     9840
atatattaaa tcaggagata agaaatatag ggagatggag agtgtaattg agaatgattg    9900
caggagaatt ctatctcttt ggaagaagaa aaataatgaa gtttggctaa tagaaataat   9960
atgtctgaag ttgaaagatt aaggggcatg tgcatggtca gcaacacatt gagagaaaaa  10020
caggcaacat aagagtaaag ggacggctgg gtcagtggct caccctata atacaagcat   10080
```

-continued

```
tttgggaggc cctggtgcat ggatcacgag gtcaggtgtt caagatgagc ctggccatga   10140
cggtgaaacc ccatctctac taaaagtaca aaaactagct gggtgtggtg gcgggcagcc   10200
gtaatcccag ctacttggga ggctgaggcg gagaattacc tgagcctggg aggtggcgga   10260
ggttgcagtg agctgagatc acgccactgc actccagcct gggtgacaga gcaagactcc   10320
gtctcaaaaa aaaaaaaaaa ggaataaaga aattgcagaa tatttgttgt cctgcaatca   10380
taaaaacaag ataagccaag aactcagctg gaagatggac agatagaaag gtctggtcaa   10440
agtcatgttt gtatagcact cattataaag agggccttgc tcccaaggta atggtataat   10500
gagaaaaagt acaagtaaat gaggctgaca gcaattggca cagattaata cctggcacag   10560
ccaattccac cttgggaaaa attctgaaga gaaatttcag agaaatttgg tagtgataaa   10620
gtataaattc atgatgggac gattttacat tggaaataag agagattctg tcaagtttgc   10680
ttgctggaac aatttccagt aatggaaaaa gttatatctt ctctttaact gtgtatataaat 10740 accacaaacc aaagtttcat gtgatcaaat tatttccgtt tattatcaga tggccagttc   10800
tgcacaaaga atgtctcagg acagaaatga tagaattcat tcttgtgagt tggtgttggt   10860
gattagcaac tctgacagtt tactaccttc actgttttt tctaagcctt acagttacac   10920
ccccaaaaaa aagaaaaaaa agaaaaaaca acaaagaaac aacaacaaaa atcaagaaga   10980
aatacaaagg ggttcagata catagacagg gatgtcaata ctaaattta caaaggactt   11040 gcacagtcaa aacctccttg atccttacaa atttctgaga aagaaatgtt agtatgcatg   11100
tttgatacat gaggaaacag gagctagaga aagagagaga cttgtccagg cttacacagc   11160
tactaagcag taaaggtgag actggaacgg agctgctgat tctcagtcct gggagttatt   11220
acgccactct gctttcttac cgagtgaaca atgtcatcag aactatggat gtctcaaaga   11280
agtaagaaat aagtgtatga agtagattag ttgatttaat tactattcat ctcccttct   11340 cctctcaagg aaatgagtta aggggttgaa ttaagacaat tgtgaggtgt gggaggagca   11400
gttttatctt cctgatggtg tcctttcttc attctctaat ggttgaggtg gtcttcatct   11460
ctatggtcac ctctcaacta ggcatgaagg cttcagctga cctaagcaac atcaatcttt   11520
tatttcttga cttttcaggga actctctctc tgatgctgat ttgcactctg ctggaattct   11580
gcctagctgt gctcactgct gtgctgcggt ggaaacaggc ttactctgac ttccctgggg   11640
tgagtgtgct ggccggcttc acttaacctt gcctagtgta tcttatccct gcactgtgtt   11700
gagtatgtca ccaagagtgg tagaaggaac aatcagtcag tcatgagata cacatgggag   11760
ggcatttgca ttgtgatgga agacagagaa gaaaagcaga tggcaattga gtagctgata   11820
agctgaaaat tcactggata tgaaaatagt taatcatgag aaatcaactg attcaatctt   11880
cctattttgt cagcgaaggg aatgagactc tgggaagtta aatgactggc ctggcattat   11940
gctatgagtt tgtgcctttg ctgaggacac tagaacctgg cttgcctccc ttataagcag   12000
aaacaatttc tgccacaacc actagtctct ttaatagtat tgacttggta aagggcattt   12060
acacacgtaa ctggatccag tgaatgtctt atgctctgca tttgccctg gtgatcttaa   12120 aattcgtttg ccttttaaa gctatattaa aaatgtattg ttgaatcaaa cccctatgga   12180
cttatggctt tatttaactg aattaaaaag ccttgattta tccaaaattg tattatagag   12240
tgtagaatga atactagggt gataaattgc aattatttga agaacctggt gatatgctct   12300
acttatcttg gattagctaa gaattctatg tatacagttg gaaaaatggc atatatacat   12360
ctatcttgaa cctgattgaa gtctgaagac ctaacatatt ttgtttcttc tagagtgtac   12420
```

-continued

```
ttttcctgcc tcacagttac attggtaatt ctggcatgtc ctcaaaaatg actcatgact    12480
gtggatatga agaactattg acttcttaag aaaaaaggga gaaatattaa tcagaaagtt    12540
gattcttatg ataatatgga aaagttaacc attatagaaa agcaaagctt gagtttccta    12600
aatgtaagct tttaaagtaa tgaacattaa aaaaaaccat tatttcactg tcatttaaga    12660
tatgtgttca ttggggatct cttgatttgc ctgacattga cttcagcaaa agcacggggc    12720
tgtaaattac catttactag attagccaaa tagtctgaat ttccagaaaa caaggcagaa    12780
tgatcattcc cagaaacatt tcccagaaaa tgtttcccag aaaactagac agaatgatca    12840
ttcaatggat cacagtgaag caaaggacac aactttttat tgtacccctt aattgtcaac    12900
aggagttaac tgatttgttg tggtgctcag acttttttat acaggtgcta gtgttttatc    12960
ctatgtattt taactcatta gtgcataaag gcaagcccca tataatgaag tctcagggta    13020
tatgaaagta gctggcttca aaataaaatt tttgagtgca                          13060
```

```
<210> SEQ ID NO 4
<211> LENGTH: 3648
<212> TYPE: DNA
<213> ORGANISM: Homo sapiens
<220> FEATURE:
<221> NAME/KEY: CDS
<222> LOCATION: (103)..(837)

<400> SEQUENCE: 4
aacccatttc aactgcctat tcagagcatg cagtaagagg aaatccacca agtctcaata        60
taataatatt ctttattcct ggacagctcg gttaatgaaa aa atg gac aca gaa       114
                                               Met Asp Thr Glu
                                                 1 agt aat agg aga gca aat ctt gct ctc cca cag gag cct tcc agt gtg       162
Ser Asn Arg Arg Ala Asn Leu Ala Leu Pro Gln Glu Pro Ser Ser Val
  5              10               15               20 cct gca ttt gaa gtc ttg gaa ata tct ccc cag gaa gta tct tca ggc       210
Pro Ala Phe Glu Val Leu Glu Ile Ser Pro Gln Glu Val Ser Ser Gly
             25               30               35 aga cta ttg aag tcg gcc tca tcc cca cca ctg cat aca tgg ctg aca       258
Arg Leu Leu Lys Ser Ala Ser Ser Pro Pro Leu His Thr Trp Leu Thr
         40               45               50 gtt ttg aaa aaa gag cag gag ttc ctg ggg gta aca caa att ctg act       306
Val Leu Lys Lys Glu Gln Glu Phe Leu Gly Val Thr Gln Ile Leu Thr
         55               60               65 gct atg ata tgc ctt tgt ttt gga aca gtt gtc tgc tct gta ctt gat       354
Ala Met Ile Cys Leu Cys Phe Gly Thr Val Val Cys Ser Val Leu Asp
     70               75               80 att tca cac att gag gga gac att ttt tca tca ttt aaa gca ggt tat       402
Ile Ser His Ile Glu Gly Asp Ile Phe Ser Ser Phe Lys Ala Gly Tyr
 85               90               95              100 cca ttc tgg gga gcc ata ttt ttt tct att tct gga atg ttg tca att       450
Pro Phe Trp Gly Ala Ile Phe Phe Ser Ile Ser Gly Met Leu Ser Ile
             105              110              115 ata tct gaa agg aga aat gca aca tat ctg gtg aga gga agc ctg gga       498
Ile Ser Glu Arg Arg Asn Ala Thr Tyr Leu Val Arg Gly Ser Leu Gly
             120              125              130 gca aac act gcc agc agc ata gct ggg gga acg gga att acc atc ctg       546
Ala Asn Thr Ala Ser Ser Ile Ala Gly Gly Thr Gly Ile Thr Ile Leu
         135              140              145 atc atc aac ctg aag aag agc ttg gcc tat atc cac atc cac agt tgc       594
Ile Ile Asn Leu Lys Lys Ser Leu Ala Tyr Ile His Ile His Ser Cys
     150              155              160
```

-continued

```
cag aaa ttt ttt gag acc aag tgc ttt atg gct tcc ttt tcc act gaa      642
Gln Lys Phe Phe Glu Thr Lys Cys Phe Met Ala Ser Phe Ser Thr Glu
165             170             175             180 att gta gtg atg atg ctg ttt ctc acc att ctg gga ctt ggt agt gct      690
Ile Val Val Met Met Leu Phe Leu Thr Ile Leu Gly Leu Gly Ser Ala
                185             190             195 gtg tca ctc aca atc tgt gga gct ggg gaa gaa ctc aaa gga aac aag      738
Val Ser Leu Thr Ile Cys Gly Ala Gly Glu Glu Leu Lys Gly Asn Lys
            200             205             210 gtt cca gag gat cgt gtt tat gaa gaa tta aac ata tat tca gct act      786
Val Pro Glu Asp Arg Val Tyr Glu Glu Leu Asn Ile Tyr Ser Ala Thr
        215             220             225 tac agt gag ttg gaa gac cca ggg gaa atg tct cct ccc att gat tta      834
Tyr Ser Glu Leu Glu Asp Pro Gly Glu Met Ser Pro Pro Ile Asp Leu
    230             235             240 taa gaatcacgtg tccagaacac tctgattcac agccaaggat ccagaaggcc          887
aaggtcttgt taaggggcta ctggaaaaat ttctattctc tccacagcct gctggtttta   947
cattagattt attcgcctga taagaatatt ttgtttctgc tgcttctgtc caccttaata  1007
ttctccttct atttgtagat atgatagact cctattttttc ttgtttttata ttatgaccac  1067 acacatctct gctggaaagt caacatgtag taagcaagat ttaactgttt gattataact  1127
gtgcaaatac agaaaaaaag aaggctggct gaaagttgag ttaaactttg acagtttgat  1187
aatatttggt tcttagggtt ttttttttttt tttagcattc ttaatagtta cagttgggca  1247
tgatttgtac catccaccca tacccacaca gtcacagtca cacacacata tgtattactt  1307
acactatata taacttccta tgcaaatatt ttaccaccag tcaataatac attttttgcca  1367 agacatgaag ttttataaag atctgtataa ttgcctgaat caccagcaca ttcactgaca  1427
tgatattatt tgcagattga caagtaggaa gtggggaatt ttattaagtt actcgttgtc  1487
tggggaggta aataggttaa aaacagggaa attataagtg cagagattaa catttcacaa  1547
atgtttagtg aaacatttgt gaaaaaagaa gactaaatta agacctgagc tgaaataaag  1607
tgagtggaaa tggaaataat ggttatatct aaaacatgta gaaaagagt aactggtaga   1667 ttttgttaac aaattaaaga ataaagttag acaagcaact ggttgactaa tacattaagc  1727
gtttgagtct aagatgaaag gagaacactg gttatgttga tagaatgata aaaagggtcg  1787
ggcgcggagg ctcacgcctg taatcccagc cctttgggag gccgaggtgg gcagatcacg  1847
aagtcagtag tttgagacca gcctggccaa catagtgaaa ccccgtctct actaaaaata  1907
caaaaaaaaa attagctggg tgtggtggca gtcacctgta gtcccagcta cttgggaggc  1967
tgaggcagga gaatcgcttc aacctgggag gcggaggttg cagtgagccg agatcgcacc  2027
agtgcactcc agccttggtg acaatgggag actccatctc aaaaaaaaaa aaaaaaaaaa  2087
aaaagataaa aagtcagaaa tctgaaaagt ggaggaagag tacaaataga cctaaattaa  2147 gctcatttttt aggctttgat tttggggaga caaaggggaaa tgcagccata gagggcctga  2207
tgacatccaa tacagagttc tggtaaagat aaaatttgat acaggtttgg tgtcattata  2267
agagaaatca ttattaaatg aagcaagtta acactctaag agaattattt tgagatagaa  2327
gtgaagctaa gctaaacttc acatgcctat aattggaggg aaaaactaag gataaaatct  2387
agcctagaag atacaataat tagtcataaa catgcattgt gaaactgtag agagcaggta  2447
gcccaaaata gagaaagatt agataaagag aaaataagta tccatcagag acagtatctc  2507
taggcttggg caagagaaaa gtccacagtg ataagcaact ccacctaagg catgaatatg  2567
cggcagagaa aacagcaata gtgaatgaat gcaaaaggtg ctgagaaatt ccacacatga  2627
```

-continued

```
gtattgtgat gagtaaatga ataaaacatt tgcaaagacc tttagagaaa gagaatggga    2687
gcatatgtga gaaataagat agttgattat gaatagaagg tagtgaagaa aagcaagcta    2747
agaaaaaatt ctgtttataa aagaaggaaa agatagttta tgtttttagc ctaagtataa    2807
gagtcctaca gatggactga aaaaaatcag tctgagagta ttagtcacaa ttaatgaaat    2867
aattacattt tatgtattga ggatgccaag attaaaaggt gacaggtaga tgttaatttc    2927
cctagattgt gaaagtgatc acgacaatca cacaacaaat aattaagtga cttggtatgc    2987
tttatttaat tgtagggcct gaggttttcc attctcattt ttctaaaata caattttgtt    3047
tctccaaatt tgacagcaga ataaaaaccc tacccttcca ctgtgtatca tgctaagctg    3107
catctctact cttgatcatc tgtaggtatt aatcacatca cttccatggc atggatgttc    3167
acatacagac tcttaacccct ggtttaccag gacctctagg agtggatcca atctatatct    3227
ttacagttgt atagtatatg atatctcttt tatttcactc aatttatatt ttcatcattg    3287
actacatatt tcttatacac aacacacaat ttatgaattt tttctcaaga tcattctgag    3347
agttgcccca ccctacctgc cttttatagt atgcccacct caggcagaca cagagcacaa    3407 tgctgggggtt ctcttcacac tatcactgcc ccaaattgtc tttctaaatt tcaacttcaa    3467
tgtcatcttc tccatgaaga ccactgaatg aacacctttt catccagcct taatttcttg    3527
ctccataact actctatccc acgatgcagt attgtatcat taattattag tgtgcttgtg    3587
acctccttat gtattctcaa ttacctgtat ttgtgcaata aattggaata atgtaacttg    3647
a                                                                    3648
```

\<210\> SEQ ID NO 5
\<211\> LENGTH: 244
\<212\> TYPE: PRT
\<213\> ORGANISM: Homo sapiens

\<400\> SEQUENCE: 5

```
Met Asp Thr Glu Ser Asn Arg Arg Ala Asn Leu Ala Leu Pro Gln Glu
1               5                   10                  15

Pro Ser Ser Val Pro Ala Phe Glu Val Leu Glu Ile Ser Pro Gln Glu
                20                  25                  30

Val Ser Ser Gly Arg Leu Leu Lys Ser Ala Ser Ser Pro Pro Leu His
        35                  40                  45

Thr Trp Leu Thr Val Leu Lys Lys Glu Gln Glu Phe Leu Gly Val Thr
    50                  55                  60

Gln Ile Leu Thr Ala Met Ile Cys Leu Cys Phe Gly Thr Val Val Cys
65                  70                  75                  80

Ser Val Leu Asp Ile Ser His Ile Glu Gly Asp Ile Phe Ser Ser Phe
                85                  90                  95

Lys Ala Gly Tyr Pro Phe Trp Gly Ala Ile Phe Phe Ser Ile Ser Gly
                100                 105                 110

Met Leu Ser Ile Ile Ser Glu Arg Arg Asn Ala Thr Tyr Leu Val Arg
        115                 120                 125

Gly Ser Leu Gly Ala Asn Thr Ala Ser Ser Ile Ala Gly Gly Thr Gly
    130                 135                 140

Ile Thr Ile Leu Ile Ile Asn Leu Lys Lys Ser Leu Ala Tyr Ile His
145                 150                 155                 160

Ile His Ser Cys Gln Lys Phe Phe Glu Thr Lys Cys Phe Met Ala Ser
                165                 170                 175

Phe Ser Thr Glu Ile Val Val Met Met Leu Phe Leu Thr Ile Leu Gly
```

-continued

```
              180              185              190
Leu Gly Ser Ala Val Ser Leu Thr Ile Cys Gly Ala Gly Glu Glu Leu
       195              200              205

Lys Gly Asn Lys Val Pro Glu Asp Arg Val Tyr Glu Glu Leu Asn Ile
    210              215              220

Tyr Ser Ala Thr Tyr Ser Glu Leu Glu Asp Pro Gly Glu Met Ser Pro
225              230              235              240

Pro Ile Asp Leu
```

```
<210> SEQ ID NO 6
<211> LENGTH: 9804
<212> TYPE: DNA
<213> ORGANISM: Homo sapiens

<400> SEQUENCE: 6
aacccatttc aactgcctat tcagagcatg cagtaagagg aaatccacca agtctcaata       60
taataatatt ctttattcct ggacagctcg gttaatgaaa aaatggacac agaaagtaat      120
aggagagcaa atcttgctct cccacaggag ccttccaggt aggtacaagg tattattttt      180
ttctaccctc agtcacttag tggcagggga agtcatagtc acggtgctta ggagatgaaa      240
ctttattgat ttaggcatgg atccatctag tttaattaat atattgggta tgaggaagct      300
acttgctgta cttccatgt ggttctctct ccctggagag gaacatttt actcagcttg       360 caaactggaa atagattttc tcacattaga agctcatttt ctgggtatga gacaggagag      420
ttcatactgt gtatgtagat ctctggcttc tgggtctgac atgtgctgag ggacacatat      480
ccttcacaca tgcttttata aatacttgat aaagtaacct gcttcttgat tggtctttat      540
aatccataag ctgtgggatg cttctctgaa gatgaaaata gtaatagagt cccatctagc      600
tattcaaagc cattccttca ttgtattctg tgcacatgaa gttggggttt gttactgaca      660
aaatatattc agatacattt ctatgttaaa aggattgtga gatgcatagg taaatgtgtt      720
tattttcagt tttacttgtc aacatagatg aatgagaaag aacttgaaag taacactgga      780
ttaagaatag gaaaatttgg catggatttt gctccatttt gtcccatcta atcacttgga      840
tagtgttcag gtgttcttgg tcagttactt ggatgctctg agctttagtt tcttggtgat      900
tacaatgaag atttgaatta caggatggct ttgaaaaaat aaacaaaact cccctttctg      960
tctgtcgaga atgttgcaca gggagttaca gaatgttctc atgactgaat tgcttttaaa     1020
tttcacagtg tgcctgcatt tgaagtcttg gaaatatctc cccaggaagt atcttcaggc     1080
agactattga agtcggcctc atccccacca ctgcatacat ggctgacagt tttgaaaaaa     1140
gagcaggagt tcctgggggt gagtgagcct cctccaactt tgactagagt aagggttggg     1200
tctagaaaag aatattgagt tgcatcaact gttttcccac ttggattcat gagaggtgtt     1260 aggtcctta aaaaacatgg tagataaaga gttgacacta actgggtcct tttgggaaga      1320
gagaagcatt tcctcataaa gactttaaat tgctaggacg agaatggcca acaggagtga     1380
aggattcata atctttatct ttacttagat gtaaagaaca attactgatg ttcaacatga     1440
ctacgtacat aaaggcgcat ggagaaaagt attggccttc catgcattag gtagtgcttg     1500
tatcaattct tatagtggct agggtatcct ggaaaatctt acgtgtggat catttctcag     1560
gacagtctag gacactaacg cagtttctca tgtttggctt ctattattaa aaaatgatac     1620
aatctcggga aaatttttt gattttcatg aaattcatgt gtttttctat aggtaacaca     1680
aattctgact gctatgatat gcctttgttt tggaacagtt gtctgctctg tacttgatat     1740
```

-continued

```
ttcacacatt gagggagaca tttttttcatc atttaaagca ggttatccat tctggggagc    1800
catatttgtg agtatatatc tataattgtt tctgaaataa cactgaacat aggttttttct    1860 cttttctcaga tctaaccagt tgtttattcc cagtattaac atgatattta taattcttaa    1920
ttataaatta tatgtgagca tatataacat agatatgctc attaacaaca acaaaagatt    1980 cttttttacaa ttaacggtgg gttaaacatt tagcccacag ttttatccca tgagaaacct    2040
gaatctaata caagttaaat gacttgccta agggccactt gactaatagt aattgaacct    2100
aaactttcag aatccaactc caggaacata cttctagcac tattcatcaa taaagttata    2160
tgataaatac atacaacttt atctgtcaac taaaaataac aacaaaggct gggcatggtg    2220
gctcacaccc gtaatcccag cactttggga ggctgaggca ggtggatcac ctgaggtcag    2280
gagtttgaga ccagcctgac caacatggtg aaacctcatc tctactaaat ataaaaaatt    2340
agctgagtgt gatagtgcat gcctgtaatc ccagctactt aagaggctga ggcaggaggc    2400
ttgtttgaac ctggaaggca gaggttgcag tgagctgaga ttgtgccatt gcactccagc    2460
ctgggcaata agagcgaaac tctgtctcaa aataataata ataataatag aaaataaagt    2520
tgtcttcatg aaaaatgagg aaagagattg ctgggggtgag aaacattaag atcaaagggc    2580
atatggtgac cttctatgcc ctagaaactc ttttaggtat tttctcctgg tatctctttt    2640
actcatcgtt ctatctggaa aaataggtgg atgagtgaga taataaggta tataacttttt    2700 taaaggtcta attgacatat aataaattgc aagtatttca gatgtacaat ttgctaacct    2760
tgacacacat agacacacat gaaaacatca ccacattaat acaatgtatg tatccatcat    2820
ttccaaaagc ttccctgtgt atctttgtaa ctctttcttc ctccctccac tccttgtcct    2880
ctcgttccca agaaaacatt gatctgcttt ctgtgaatat aaattaactt acatttttta    2940
gagctttata taagtatgtt ctctttactg tttgtcttcc ttcgctgcac agttattttg    3000
agattcttca agtttttttct ttatatcgat acttcattca caagaatata ttttaattct    3060
agactatgtc acattgactt tgtagtctgc taaatcctta gtgctcagat gacttgttca    3120
ggactctcct tgaacctgta cctctgttat aattgaaact tgtctctact gtcttttat    3180 ttcaaacaca gcttatgagg tgtctctcaa cccatcaaac tcacaatctg agtctttagg    3240
agattgcttt gaatttgtgc tattgactta tatttatatc aaatatgtaa atgtttggta    3300
aaaatatcat catgtacatt ttcataatta ctctatattc acatgatata tgtcagactc    3360
tggaaatatg catgccacag acacgtgttt cttgcctaaa ggggctgatg gaagacgcac    3420
atacaaatag acgattgcaa tagaatgaga gtggtggtct aatcgattca tgccctgatg    3480
ttgctggacg ttgctactcc aagagtaacc cctgcattgt cagggttagc atctcctgga    3540
agcctcatgt aaatgaagaa tttcatgctc catccaggac ctaatgaata agaatctgca    3600
ttttagcaag accctcatat gattcatata cacttttttt ttttttttt agatggagtc    3660 tcactcttgt cgcccaggct ggagtgcaat ggcatgatct ggctcactg caacctctgc    3720 ctcccgggtt caagtgattc tcctgtctca gcctccctag tagctgggac tacaggtgca    3780
tgccacagtg gctggctaat ttttgtattt ttagtagaga cagggtttca ccattttggt    3840
caggctggtc ttgaactcat gacctccggt gattcccccg cctcggcttc ccaaagtgct    3900
gggattacag acatgagcca ccacacccag ccttattcgt atacacattt aattctgaga    3960
agcactctat agaaaataag aataagaaaa tattgggctc acaggtgaca ttaataagta    4020
actttatcga gtaccccaaa tgttacctat gtttggaaga tggggttaaa aaggacacat    4080
tgaaaacaag aaactcattg tggctttttt ttcctccttt ttgaacagtt ttctatttct    4140
```

-continued

```
ggaatgttgt caattatatc tgaaaggaga aatgcaacat atctggtgag ttgcccgttt      4200
ctgtctttgt ccatccttga aaagataaga agaacagagt tttaagagtc ttaagggaaa      4260
cacatctttg tctcctatat tacttgtgaa tgtggatata tgattttgtt tcaatctatt      4320
ttgtgtccta aggctttttg caacagaagt tggatataat cattagaaac ataaattgta      4380
ccatttaaca tacaatgaag tttatgttta ccttgacgtt tcttctaaaa aaagtgtcct      4440
cacaccggca ttgtccttgt aggcatattc acatgatcaa ataaataatt agttttcaat      4500
taaggagaat atttgaggaa agaccgtacg tgttcatgtg gttcctgaag gcagtccagt      4560
gagaaagtaa tatatgctca ttaaacaatg cggacatttt cagggtttcc cttttttaacc      4620 aaaatttgga agcaatgtgg aatttactgg atgcatccag ccctgaaatg aagataggtt      4680
tattgaatgt gccagcaagt gcaggcccag gtctgagtgt tcttcattat tatcaggtga      4740
gaggaagcct gggagcaaac actgccagca gcatagctgg gggaacggga attaccatcc      4800
tgatcatcaa cctgaagaag agcttggcct atatccacat ccacagttgc cagaaatttt      4860
ttgagaccaa gtgctttatg gcttcctttt ccactgtatg tattttttttt tgtgtgggaa      4920 gactaagatt ctgggtccta atgtaagtaa gaagccctct tctcctgttc catgaacacc      4980
atccttttct gtaacttcta ttacacagta tagtggttct gtaagttcac acagcccagg      5040
gagatgctgg ctgcccactc ccctcaaccc aggcaaattc ctcggggtta aagttatcta      5100
ctgcaagtga cgatctctgg gttttttctgt gcctgtgttt gtgtgtgtgt gtgtgtgtgt      5160
gtgtgtgtgt gtgtatgtgt cactttaaaa ggactggtca gatggtaggg agatgaaaac      5220
aggagatgct ataagaaaat aaactttttgg ggcgaatacc atgtgactct ttttgtttgt      5280
catttgttgc tgttcaatag gaaattgtag tgatgatgct gtttctcacc attctgggac      5340
ttggtagtgc tgtgtcactc acaatctgtg gagctgggga agaactcaaa ggaaacaagg      5400
tagatagaag cccgatataa aatcttgaat gacaggttaa cgaattggag ctttattcct      5460
taaaaatatg gcctgggttt tctgaaacat ttcttccaga aaatagtttc tccaagtttt      5520
attactttgg tttacaaatc tcacatttta aatcacattt tataccata agtagcacac      5580 atttcataat atatccctct gaatgagggt tgggataata ggatctgtat aatgttagaa      5640
aatgccttaa agtgtgtgga gcatgagaga tggatgtgca gaaggcttgt gaggaaacca      5700
cccaggtatc tggccttgtt ttctgcccca gaagtagccg cctattcctg tttctgtttt      5760
attcctttgt ttcttgactt ttcctttcca acttgctcta aaacctcagt tttctttcct      5820
ttctgattca tgactaccaa atgtttccac ttgcctcacc cgtccattac acctttgata      5880
agaaccacca gcaccttgtg ctcatgtact tgcccatgtc tgatggaaga aacatactct      5940
ctccatctgt ccactttcct gaggcattca agtctagcca cctttttaaaa tcactctcct      6000 ccaggctggg cacggtggct cacgcctgta atctcagcac tttgtgaggc tgaggagggc      6060
ggatcacttg aagtcaggag ttcaaaacca gcctggccaa atggcaaaac caaatcttca      6120
attaaaacca aatcttaaac caaatctcta ctaaaaaata caacaaaaca aaacaacaac      6180
aacaaaaaca gaaaggaaa cattagccca gcgtggtggc aggtacctga ggttccagat      6240
acttgggagg ctgaagcagg agaatcgctt gagcccaaga gatggaggtt gcagtgagcc      6300
gagatcatgc cactgcacca cagccagggt gacagagcca tacttcccag cacattggga      6360
ggccaaagct gaagaataat ttgaggtgag gatttggaga ccagcctggc caacatggtg      6420
aaactccgtc tgtactaaaa atataaaact tagtggggca tggggcaca cacctgtaat      6480
```

-continued

```
ttcagctact taggaggctg aggcaggaga attgcttgaa cccgggaggc ggaagttgca   6540
gtgagccaag atcgtggcca ctgcactcca gcctgggtga catagtgaga ttctgtctca   6600
aaaaaaataa aagaaattta aaaaatcact ctcttccaaa gatagataaa taagacagca   6660
gatatactaa ggaataacct caccaacttg tcattgactg acatgatttc ttttgggccc   6720
acttggccag ctagtctggt ttggtttttct ggaaatgaaa gaaataatca gagtttaatg   6780
acagagagcg tgagacccag aaaagacaaaa gtagatgagg taagtctctt gagcgagact   6840
tctagggatg ggaaatttgt ggtgattgat atgaaatgat ttttcccttta tcaggttcca   6900 gaggatcgtg tttatgaaga attaaacata tattcagcta cttacagtga gttggaagac   6960
ccagggaaaa tgtctcctcc cattgattta taagaatcac gtgtccagaa cactctgatt   7020
cacagccaag gatccagaag gccaaggtct tgttaagggg ctactggaaa aatttctatt   7080
ctctccacag cctgctggtt ttacattaga tttattcgcc tgataagaat attttgtttc   7140
tgctgcttct gtccacctta atattctcct tctatttgta gatatgatag actcctattt   7200
ttcttgtttt atattatgac cacacacatc tctgctggaa agtcaacatg tagtaagcaa   7260
gatttaactg tttgattata actgtgcaaa tacagaaaaa aagaaggctg gctgaaagtt   7320
gagttaaact ttgacagttt gataatattt ggttcttagg gttttttttt tttttagca   7380 ttcttaatag ttacagttgg gcatgatttg taccatccac ccatacccac acagtcacag   7440
tcacacacac atatgtatta cttacactat atataacttc ctatgcaaat attttaccac   7500
cagtcaataa tacatttttg ccaagacatg aagtttttata aagatctgta taattgcctg   7560
aatcaccagc acattcactg acatgatatt atttgcagat tgacaagtag gaagtgggga   7620
attttattaa gttactcgtt gtctggggag gtaaataggt taaaaacagg gaaattataa   7680
gtgcagagat taacatttca caaatgttta gtgaaacatt tgtgaaaaaa gaagactaaa   7740
ttaagacctg agctgaaata aagtgagtgg aaatggaaat aatggttata tctaaaacat   7800
gtagaaaaag agtaactggt agattttgtt aacaaattaa agaataaagt tagacaagca   7860
actggttgac taatacatta agcgtttgag tctaagatga aaggagaaca ctggttatgt   7920
tgatagaatt ataaaaaggg tcgggcgcgg aggctcacgc ctgtaatccc agccctttgg   7980
gaggccgagg tgggcagatc acgaagtcag tagtttgaga ccagcctggc caacatagtg   8040
aaaccccgtc tctactaaaa atacaaaaaa aaaattagct gggtgtggtg gcagtcacct   8100
gtagtcccag ctacttggga ggctgaggca ggagaatcgc ttcaacctgg gaggcggagg   8160
ttgcagtgag ccgagatcgc accagtgcac tccagccttg gtgacaatgg gagactccat   8220
ctcaaaaaaa aaaaaaaaaa aaaaaaagat aaaaagtcag aaatctgaaa agtggaggaa   8280
gagtacaaat agacctaaat taagctcatt tttaggcttt gattttgggg agacaaaggg   8340
aaatgcagcc atagagggcc tgatgacatc caatacagag ttctggtaaa gataaaattt   8400
gatacaggtt tggtgtcatt ataagagaaa tcattattaa atgaagcaag ttaacactct   8460
aagagaatta ttttgagata gaagtgaagc taagctaaac ttcacatgcc tataattgga   8520
gggaaaaact aaggataaaa tctagcctag aagatacaat aattagtcat aaacatgcat   8580
tgtgaaactg tagagagcag gtagcccaaa atagagaaag attagataaa gagaaaataa   8640
gtatccatca gagacagtat ctctaggctt gggcaagaga aaagtccaca gtgataagca   8700
actccaccta aggcatgaat atgcggcaga gaaaacagca atagtgaatg aatgcaaaag   8760
gtgctgagaa attccacaca tgagtattgt gatgagtaaa tgaataaaac atttgcaaag   8820 accttttagag aaagagaatg ggagcatatg tgagaaataa gatagttgat tatgaataga   8880
```

```
aggtagtgaa gaaaagcaag ctaagaaaaa attctgttta taaaagaagg aaaagatagt      8940
ttatgttttt agcctaagta taagagtcct acagatggac tgaaaaaaat cagtctgaga      9000
gtattagtca caattaatga aataattaca ttttatgtat tgaggatgcc aagattaaaa      9060
ggtgacaggt agatgttaat ttccctagat tgtgaaagtg atcacgacaa tcacacaaca      9120
aataattaag tgacttggta tgctttattt aattgtaggg cctgaggttt tccattctca      9180
tttttctaaa atacaatttt gtttctccaa atttgacagc agaataaaaa ccctaccctt      9240
tcactgtgta tcatgctaag ctgcatctct actcttgatc atctgtaggt attaatcaca      9300
tcacttccat ggcatggatg ttcacataca gactcttaac cctggtttac caggacctct      9360
aggagtggat ccaatctata tctttacagt tgtatagtat atgatatctc ttttatttca      9420
ctcaatttat attttcatca ttgactacat atttcttata cacaacacac aatttatgaa      9480
ttttttctca agatcattct gagagttgcc ccaccctacc tgcctttat agtatgccca       9540 cctcaggcag acacagagca caatgctggg gttctcttca cactatcact gccccaaatt      9600
gtctttctaa atttcaactt caatgtcatc ttctccatga agaccactga atgaacacct      9660
tttcatccag ccttaatttc ttgctccata actactctat cccacgatgc agtattgtat      9720
cattaattat tagtgtgctt gtgacctcct tatgtattct caattacctg tatttgtgca      9780
ataaattgga ataatgtaac ttga                                             9804
```

```
<210> SEQ ID NO 7
<211> LENGTH: 1687
<212> TYPE: DNA
<213> ORGANISM: Mus musculus
<220> FEATURE:
<221> NAME/KEY: CDS
<222> LOCATION: (133)..(867)

<400> SEQUENCE: 7
gttacaagtt cacaagaagg aaccaaggat cagcctgaga gaacccagag ttaaggctct        60
tcgggttcct gagagctcgg ctggaagtga ctgggtgaca aggcacacag gctcagccgt       120
gggagctcaa tc atg att cca caa gta gtg acc agt gag act gtg gca atg       171
              Met Ile Pro Gln Val Val Thr Ser Glu Thr Val Ala Met
                1               5                   10 att tcg cca aat gga atg agt ctt ccc caa aca gac aaa ccc cag cct         219
Ile Ser Pro Asn Gly Met Ser Leu Pro Gln Thr Asp Lys Pro Gln Pro
  15                  20                  25 ttc cac cag tgg caa gac agc ctg aag aaa cat cta aag gct gag atc         267
Phe His Gln Trp Gln Asp Ser Leu Lys Lys His Leu Lys Ala Glu Ile
30                  35                  40                  45 aaa gtg atg gcg gca atc cag atc atg tgt gct gtg atg gtg ttg agt         315
Lys Val Met Ala Ala Ile Gln Ile Met Cys Ala Val Met Val Leu Ser
                50                  55                  60 ctg gga atc att ttg gca tct gtt ccc tcc aat cta cac ttt acc tca         363
Leu Gly Ile Ile Leu Ala Ser Val Pro Ser Asn Leu His Phe Thr Ser
            65                  70                  75 gtg ttt tca gtc ctg tta aaa tct ggc tac cca ttt ata gga gct ttg         411
Val Phe Ser Val Leu Leu Lys Ser Gly Tyr Pro Phe Ile Gly Ala Leu
        80                  85                  90 ttt ttt ata gtc tct gga att ctg tcc atc gtc acg gag aca aag tca         459
Phe Phe Ile Val Ser Gly Ile Leu Ser Ile Val Thr Glu Thr Lys Ser
    95                  100                 105 aca aaa att ttg gta gac agc agc ctg act ctg aat atc ctg agt gtt         507
Thr Lys Ile Leu Val Asp Ser Ser Leu Thr Leu Asn Ile Leu Ser Val
110                 115                 120                 125
```

-continued

```
tca ttt gct ttc atg ggc atc att atc atc tct gtc agc ctg gct ggt        555
Ser Phe Ala Phe Met Gly Ile Ile Ile Ile Ser Val Ser Leu Ala Gly
                130                 135                 140 ttg cat cct gcc tca gag cag tgc ttg cag agc aag gag ctt aga cca        603
Leu His Pro Ala Ser Glu Gln Cys Leu Gln Ser Lys Glu Leu Arg Pro
                145                 150                 155 act gaa tat cat tac tac caa ttc ttg gac agg aac gag tgc ttt gcc        651
Thr Glu Tyr His Tyr Tyr Gln Phe Leu Asp Arg Asn Glu Cys Phe Ala
                160                 165                 170 gcc aag tct gtt ctg gct gga gtc ttt tca ctg atg ctg atc agt act        699
Ala Lys Ser Val Leu Ala Gly Val Phe Ser Leu Met Leu Ile Ser Thr
                175                 180                 185 atg ttg gaa ctt ggc ctg gct gtc ctc act gcc atg ctg tgg tgg aaa        747
Met Leu Glu Leu Gly Leu Ala Val Leu Thr Ala Met Leu Trp Trp Lys
190                 195                 200                 205 cag agt cac tct aac atc cct ggg aat gtt atg ttc ctg cca cat agc        795
Gln Ser His Ser Asn Ile Pro Gly Asn Val Met Phe Leu Pro His Ser
                210                 215                 220 tca aat aat gac tcc aac atg gaa tca aag gta ctt tgt aac ccc tca        843
Ser Asn Asn Asp Ser Asn Met Glu Ser Lys Val Leu Cys Asn Pro Ser
                225                 230                 235 tat gag gaa caa ttg gtt tgt taa gaaaaacaaa acaaacaaa actaaatacc        897
Tyr Glu Glu Gln Leu Val Cys
                240 acaaaaacaa atggaactat accgcagaag atatgtcttc atgataatgc agaaattcca        957 accatcacag ggtagcaatg cttgctactt aaaatgtaga ctgttcatac agtgggtacc       1017 agtatgagtt gaatgtgtgt attactggca ccctattgat tttcatgacc ttggcttcag       1077 ccaaagccca gacctacaaa tggtggcctt tcttagaaaa ccaaacagaa tgtttcaggc       1137 cattgtagtg gggaaaaggg acaacatttt cttgccccct gcaattaaca gcaacagtta       1197 accattagca gtctttgtat tcagaatctc tgctatgacg tgggtcttct atcatatcag       1257 ttttattcac tggtgtgaat aaacaaggga cctgcaatga agtctgaaga agtttccatg       1317 ttgttggttc aaaataaagt cttttttgtga ttgtatattc ttttttgtatg gggttttgtg     1377 tgggtttttgt tgttgttgtt gttttgcttt tatgcacaga tcaagtcctc agtggtacat      1437 aaacacatgt gtttgctatt tttttttttgt tctctatcaa ccaaaaaaaa aaaaaaaaaa     1497 ggcatgggaa agagaaaaag gaatatatct gtgtctctgt gtttatgtgg tgtgtgtgtg      1557 tgtgtgtttt aaactaaaac tgaatgaaca ttcaaagttt agcaatgtat tttggaggta      1617 ccagataaca tacttatttc tagaatcgcc agagcaaatg agagacattt tgtcgcttct      1677 tataagaggc                                                             1687

<210> SEQ ID NO 8
<211> LENGTH: 244
<212> TYPE: PRT
<213> ORGANISM: Mus musculus

<400> SEQUENCE: 8

Met Ile Pro Gln Val Val Thr Ser Glu Thr Val Ala Met Ile Ser Pro
1               5                   10                  15

Asn Gly Met Ser Leu Pro Gln Thr Asp Lys Pro Gln Pro Phe His Gln
                20                  25                  30

Trp Gln Asp Ser Leu Lys Lys His Leu Lys Ala Glu Ile Lys Val Met
            35                  40                  45

Ala Ala Ile Gln Ile Met Cys Ala Val Met Val Leu Ser Leu Gly Ile
```

-continued

```
          50                    55                    60

Ile Leu Ala Ser Val Pro Ser Asn Leu His Phe Thr Ser Val Phe Ser
65                    70                    75                    80

Val Leu Leu Lys Ser Gly Tyr Pro Phe Ile Gly Ala Leu Phe Phe Ile
                    85                    90                    95

Val Ser Gly Ile Leu Ser Ile Val Thr Glu Thr Lys Ser Thr Lys Ile
                100                    105                    110

Leu Val Asp Ser Ser Leu Thr Leu Asn Ile Leu Ser Val Ser Phe Ala
          115                    120                    125

Phe Met Gly Ile Ile Ile Ile Ser Val Ser Leu Ala Gly Leu His Pro
          130                    135                    140

Ala Ser Glu Gln Cys Leu Gln Ser Lys Glu Leu Arg Pro Thr Glu Tyr
145                    150                    155                    160

His Tyr Tyr Gln Phe Leu Asp Arg Asn Glu Cys Phe Ala Ala Lys Ser
                    165                    170                    175

Val Leu Ala Gly Val Phe Ser Leu Met Leu Ile Ser Thr Met Leu Glu
                180                    185                    190

Leu Gly Leu Ala Val Leu Thr Ala Met Leu Trp Trp Lys Gln Ser His
          195                    200                    205

Ser Asn Ile Pro Gly Asn Val Met Phe Leu Pro His Ser Ser Asn Asn
          210                    215                    220

Asp Ser Asn Met Glu Ser Lys Val Leu Cys Asn Pro Ser Tyr Glu Glu
225                    230                    235                    240

Gln Leu Val Cys

<210> SEQ ID NO 9
<211> LENGTH: 11845
<212> TYPE: DNA
<213> ORGANISM: Mus musculus

<400> SEQUENCE: 9
gttacaagtt cacaagaagg aaccaaggat cagcctgaga gaacccagag ttaaggctct      60
tcgggttcct gagagctcgg ctggaagtga ctgggtgaca aggcacacag gctcaggtag     120
gcaaccctga agggacttcc ctctgtgtag cactctgttt ctgggactga gttacaagaa     180
cttgctgatg ctcatgaaag caatggagac acggggctc tttagaatta aatgggcaaa      240 ggcacaggc atctggctta cctctgtcct ggcatttta gctgcataat cttggtgatc       300
actgacataa ggagcagaac tctcaggtca ttcactgatt aggcagccta agggctgaga     360
atagcacaga gaacagaagg gagccaagat gagctcagaa accgattccc cagggaacat     420
ggtccttcca cctaacaagg gcatgattgt cagtatcatg acaaaacttg aaaaaagctt     480
aggactccag gacttctcat atgggtgcat tcagctgctt cttcacactg aagagactta     540
aacacaggct gccctggca ggtgggaaaa taaggagaga accagagtca gagacagctg       600
tgccgccaca cacaactgtg tgtaggcaac tggtcagtaa tgagaacttt gcctgtttat      660
ttagcattta tttgatgttg ctgtgcaaag catcattact tcctcatata catcaaagtt      720
ttgattctga atttgttact gattgtgatt ttattaatta atgtaaagga ttgtttttcaa     780 gaataaaaac actagattat gtctactaaa atatgataaa atgtgaggtg ctaatcctaa      840
aattggcact attagacaca cgaaacagat gcatagggtt gcacgttttg agtggtacat      900
agcatggatt ggaaagcact gaaggctgac tttagtacct catggatagc aaagcagccg      960
gacagtgcaa gtcattgaat aaagacaatg cacttgttct aggtgaaatt gggaaagagc    1020
```

-continued

```
cagagctaca tctgacaaat tttgtgtaaa catttgggca tagaaacaga aacctgtggg    1080
gatccaggat ttcccttcct atgaggtgtt tattatctaa aatcattgtg gtgtgtttaa    1140
cattttgaaa aaaataactc ctaaatctga gatgtgatgg ttttacattt ctctgtacca    1200
gcagtttctt ctgccaaagg acaggtcaag gatgcccaaa ggtgcacagt ctgggaggtg    1260
ggggcagaac tgggaagcat ggtttgtttt gtttgttgtt attttatgtt caaagccaag    1320
gcacttaatg acttactgaa aattcatgtg ctgtgtactc tgatcatgct tttccttccc    1380
atttcttttc ctagatcctc tcaaactatc caacactatc caactttgca tcttctctct    1440
ctctctctgt ctctgtctct gtctctgtct ctctgtctct ctctctctgt ctctgtctga    1500
ctctctctgt cactgtctct ctgtctctgt ctctgtctct gtctctgtct ctctgtctct    1560
ctgtctctgt ctctgtctct ctgtctctct gtctctctct gtctctctct gtctctgtct    1620
ctctctctca cacacacaca ttagcaaaaa caacaaaaaa ggagaatgaa atgtaaatca    1680
accaagcaaa cagaaccaaa actaaaccaa accactacaa tgggcacagt attttatcac    1740
acctgagtcc attttctctt ccagccgtgg gagctcaatc atgattccac aagtagtgac    1800
cagtgagact gtggcaatga tttcgccaaa tggaatgagt cttccccaaa cagacaaacc    1860
ccagcctttc caccagtggc aagacagcct gaagaaacat ctaaaggctg agatcaaagt    1920
gatggcggta aatcccactc agaacatcct ggggtgggta gagggcagag ggtgaggctc    1980
tatgtattag gaccagagat aaatttgggt ggggggagcc ttcagttttg acagaatgat    2040
cacagagtgg ccagtacatt ggtggaagcc ccatggcaag ctgcttacat cactaaaacc    2100
ttctaaaatt ggcaaataat tccgtttatt atgatgaact tggactacac ttcaatgacc    2160
ttattccatg tgtcattgag attttgttgt ttagttctct ttttttttct tttcattttt    2220
gaagcgtacc ttactaagtt attttattgg tgaaaatatt tgtagctaca ttctaggtgc    2280
tctctgagtg taaaaagctc ttctcctcct tagtgaaaag agacggtaca gaaagaccat    2340
tggttctcta ctctgtgttc attctagaat cacaaatgca actattttgg gtaaagggag    2400
aagaaaaaca tttgctgtga gttgttttc agtcttgtct gtactagcgc tatatgcatg    2460
ggtctctgtt acccagtctc agaacttaat ggaactgatg gcctcgtatt gggcatacat    2520
acaagccact ggattccttt gaagtacatg tagcaaaaag tttataagat ttcttaatac    2580
aaaattccaa gacctgtgag tctgagaggt gaaggaaggc atcaggaaga caaaattgcc    2640
cttttaatat ggaagcaagg gatcccaaga atgaacaacg ggactgaagg tcctgtggag    2700
cttgacagag acagtggacc tatgtagtag tctgtgggtt ctgaatgatg tgtggagagg    2760
tttccacatt ctagtgctca gagtgggaag ggtttcagat gcctgttttt cccacaatag    2820
ggagcagaga cttgttaccc atgcactcac gttcagccca gcctggagat gccagaaagg    2880
gtcatgagca tgcaatgggt tcaaggacag aaacgcctaa aggtgacccg aggctctagc    2940
agaactacat ccccaccaga atgagctttc ctctctcact gcagagcttg tacagtgtct    3000
gtgtgctcac tgggatgttt gtagaagatg acaatgcacg ggcaccatgg gaaaagtgga    3060
gaggtccttc ttgtcattgc tggtttaatc accatttccc ttctttcaac aggcaatcca    3120
gatcatgtgt gctgtgatgg tgttgagtct gggaatcatt ttggcatctg ttccctccaa    3180
tctacacttt acctcagtgt tttcagtcct gttaaaatct ggctacccat ttataggagc    3240
tttgtttgta agtagacttc tgtggggaat aagatgggga ggagagagaa gggagttttc    3300
acctagctgc attcctgtat actgtgaaaa aaaggtcaat ggtaaacctt gttctcatgt    3360
ctgtcatcag aggtcttagt tatatcatcc tgaagatttt tacatctaat ccatttctta    3420
```

```
taaatttcac cctatcatgt catctattga gcgatgatga ctttggtggc cacttgagtt    3480
tagggaaaag tctaggaagt ggcactcaaa tgatctagag ctttctgtat cgtgcaagtt    3540
cactcggtgg accccactgc aggaaagaac actttcattc ttttgatctg gctttttgga    3600
ggcattccgg gtgatagact agatattcct ctgagcctgc tccatgtctg gggtgaggag    3660
gtcatgaagg tccttttctc agaggaccgc tcttctctag acagatgtgg atgagtcccc    3720
cacacaagtg aggattcctc tcactggggc ttccaatctg cttagtacag ttttcccct     3780 tcctacattt cttcctttga ttcatccaca gctcaatctt tccttctctt gtgtcagtga    3840
tttctgattt tcatttctct gaccaatgta ttgtctgatt tcaccagatt tccatgattg    3900
ttctttgtcc cagtttccat tcaaagacac tgcattccac cacttctgtc tccagagtct    3960
ccactaagat gtccttatcc gaaccttctc agacttccct tgtccttgat gactttgact    4020
ttttcagatt tatgctggcc tagattttg taaatattta tgttcgagtt tgtctgatat    4080
tctgttaatc tttaatggag tagagagtgg tgactgtgtg ggtgacaatg acatcagtga    4140
catgccatac tgtaggtagc atgaagggtg catattatct acaacatgtc actgttgaca    4200
taaccctgat gtggtgatgt ctaggtcagt gctgtttctt tatatttctc tcctcaccat    4260
tgtgtgctct ttccattgag catctcttgc attagaagag acactcagtt cttttaactt    4320
tattagactc tatctctgaa actgtgggca tagctcagca gcaaacacat ccatagactt    4380
cacagaccct gaggttaatc cctattattg caaaggtaaa gatccagcat ttgtttatat    4440
ggacaggctg cttgacttta gagaatagaa atcacaagtt ttctacttga aaagaaaatc    4500
ctaaatgatt tgttacttgg tttcatttca tttcttggat aatagatcat gataaatcat    4560
gatttaaaat aatcagaact aaaggcttct ggaaatgaaa ccttatagtt cctttctctt    4620
gatctttaga accagttact gaaagtcctc tttctttta tatgtgtttg ttaatatctt     4680
cccttatttc cttaaggaaa caaaaaacaa aaacctattg tagagcactc tcaaactttt    4740
accaaaatct gaaaggggta cttttcctaaa ctcatttttg gatgccagca ttatgttgat    4800
gccaaaatag tgatgtaatg ctggccagga acatgacagg aaatgaaaag tgcaggccaa    4860
tgtcttagag gatgtagctc ccaaattcct cactaaaata ccagcatgct ggaaattgca    4920
tatttaaaat tacctcaata tgttcaagtg agatttactg aaagaagttt gcatggtttt    4980
tatattcaaa tcagagtccc attactttat tgatgaaagg agagacaacc ctgaaaacta    5040
ttttttattc tctctccttg taggtcaaag catagactct aaaataatct aaatccatat    5100
tttcccttgc aattaacaaa acatccttt gctatccctt aaagtgctta tgaatttga     5160 tgggataaat ttctgctctt ttcttttact tttctgaata gtgcatggac aaaaagacac    5220
acttgtgagc ctaagtttgt ggatcattgg tcatttggtc cgtgagagtt tgtcataaac    5280
accgtagagt aaactgtagt cactttgtac atagaaattg aactgccaat gttttcttct    5340
tgtctgagca gttatagtc tctggaattc tgtccatcgt cacggagaca aagtcaacaa     5400
aaattttggt gagtacaaga gtcatatccc agaactaatg agcacaaaac ctcagggctg    5460 ggctttaat ctctacagtg attacttctt caatttgtga gctgattctg ggttctccat     5520
ttccctacat ggaacacact ctttctgtca tggtgatgaa aatcatagtg tgcctgatgt    5580
ctgagaccag tgccaagaaa tctcatgtcc tgctctctta tgatgccatt gtgtaggcag    5640
caggcaacga tggttatttt gatcatctaa gtgactggat tgagaagcac ctaaaagact    5700
aataaaaaat acctctgggg gtgttctagt tctaaactgt gattgctcca ttcactaata    5760
```

-continued

```
taaagactac gatggaataa aagggagaaa ttgaactgtg gttagcatag gtatcctctc    5820
actgggcttc ccgaccatca tgttgtgagc tgttctgctc tgccacccaa gtcccacaat    5880
ggtcagctga gcctctgaaa ctgagccaac atattttat cttgagttgt ttatgtgagg      5940
cactttgtca tggcaaggaa aagtctaaca acacaaattt tactcttcag tactaaagct    6000
attgtcctta tttttaaaga gttttattta ttgtggatat actatgcaat ctcaccattt    6060
aaaagtcata tgaatcccta gagaaaacat tcatgttttt cctctatatc tccataaagg    6120
aaaggctttt gctgtgttgg ctatacaatt tgaactggga agcagaatgc tggaattctg    6180
aaactctcag taactatttg ttttagctaa gaattcagct ttcgtacttt atttccttcc    6240
agtgaaaaac tagtcttgga cagaaaaaag ctggactata gaaagaagtt ttgaacaatg    6300
taaagattca cctagtcttc agtcacacat tcctcaagag ttgattcaga aagtcattgg    6360
agagaatgcc atgtaatgca atagcttagg gatttagtta tgaagagctg actaacctag    6420
tctcccaaat atatagaatg ttaattactt tcctgatgct gtaataaaaa aaataccatg    6480
actaaaagca attaaacata taagtagtct gcaagtagat taaggctcat gactgatgct    6540
tcacaaatgc tgaagaatgt tcttttcata caagtgtaga gagactaaag aagactccca    6600
gttaggatga acctagtgta ttccaagagc acacatacta tcagtatcca gattgcaaat    6660
attgttcaag gtgtccaaga gtttgatttt agtcactatt tgtgaaaaga agcatcgaaa    6720
agcaccaagt tctgagtgat ttacacaatc tctctaaaat ataagtgacc taaaattaaa    6780
tcaaactcaa gtgccataca gctctgtgtg ccctaaatat acctacctgt aactgtagct    6840
ttcagactga tcttagctca attttcattt tctatacatt gaaaaagaaa gaaagccact    6900
atcaagaaat tttctttgct tcactgacac cataagtgtt atggagaaga gatccaaagt    6960
gagcattaga actgagtgat gccgatcagt gagactccaa ggacctctgg ccctgtagcc    7020
tcaatttacc aacatctagt cccattctgt ttctttctgc ctcacactgt ttccacacat    7080
aacatcctta gtcacgtatc tagatttctg tctacagccc tagttatagt caatcattag    7140
gatttccaga atacaaggtc tacctgacac tgagaacaaa ttcctcacac tcacctttgt    7200
gtatatgagc gtttgagaga ggtagaatgt aaggactgcc tcaccagcct tttctgtgtg    7260
attgaggttt ggaaaggatg tgttattcta aataaattgg ccagtattag atgtgtccat    7320
actcaactgt tgaaataact caactcaaaa gaaggaatgg ttcattttgg ctcatatttc    7380
agaggcttag cagtgtatca ttttggtgaa tctatttgtt ttgagcttgt agacaggcaa    7440
taagtggctt atgctaaaaa agcaaagatg tgtgccatgt ggcagcaagg gagaaaaaag    7500
agagtaagat gaaggtttta tgttctgata tatccccttc ctgggctttt ctctgaagac    7560
aaacctttga ttaaaaggta tttccttttt aatcaagagg catttctgac acaaattatc    7620
tacctgagga tcaggtcttt aataattgag gttcaggtga tgtcaagttc acactacagc    7680
aatgagaatg ttgaaggaca gaaacatggc taatgcctgt acctgttcct cttttcacac    7740
tctctagaga gttttccaat tttacattag aggattccat caaaagtcat cggtgaagat    7800
tttgccaggg tagtatttta attttcacca ttgaaatcct gtttatctat cttattgtca    7860
tttaggtttg gaatgagtgt gttcctagac attcataaga cctaataaat gtggtgatgg    7920
tggttgggta gagtcaccta gcaaatatca tctgggaaat ggagtatagg gaaaatagac    7980
ctggaaaacc agggctctcc ttttttcttct ggtagcaatt attcattagg aagaataaag    8040
aaataaatta ttaatctttc agctgctaat gaagccaaat aacaagaatt gctgcaccat    8100
tttggaagaa aggtataaat gaaacgtgct gcttcttcca ggtagacagc agcctgactc    8160
```

-continued

```
tgaatatcct gagtgtttca tttgctttca tgggcatcat tatcatctct gtcagcctgg   8220
ctggtttgca tcctgcctca gagcagtgct tgcagagcaa ggagcttaga ccaactgaat   8280
atcattacta ccaattcttg gacaggaacg agtgctttgc cgccaagtct gttctggctg   8340
taagtatttc taaaggctgt agtgaacgtt tttagttatg gggaaatagt actctttttc   8400
ctatcttttg aaactctgtc actctgtttg gtttgagatc ttagctgaat aaagcaaagg   8460
taaataatga tagagctttt taaccccaaa tcattttaac tttgaaatta ttctggatta   8520
aaagctttaa cacctttttcc agagggccgg atatatagat tggaaagaga tgtcagagat   8580
gccgttagca caataagatt cataaccaaa agactctggt gattttgact tgccaacaag   8640
gaaaccatgc acatatgtag tagagggagt aaagtgagct gagcaagact cagctaagca   8700
ctgagaaatg gattgtgaca aggacaggag tggggcgggg gtgtcagatg tctgctccct   8760
caagtgctca cagtagccag cactgggctg tgtggataca acctcactgt tgcttccatc   8820
atccgcaaag agatgggatt gttaaaagag aaaagaaata cagcgaggtg gagaagagta   8880
gaactggcag tgatgtgagg gactgccatc ttgttggaag aaagcaatgc aatttgacta   8940
acaggaataa catgccttca attacaacat ctaagaacat acacgtggtc cgcatcacat   9000
ggagcgaaca ttgggtaaga taacaatgaa gatcctgcat tatattaatt ctcttatgac   9060
aataaaagta aaataagaaa aaccacagct ccaaaatggt gagatagttg ggtctggtca   9120
acctcaggct ttctgtttcc ttatggatct gggtccagtg tttcttcctt agttaagaaa   9180
accacaagaa gaaaaagtgt gtgtaaatta gatgcataat aatgtgagta aagtaacatt   9240
tggaataact aagcctgact ttagaagctt gaagcattgg ggagaaattc gcatgaatca   9300
caaagtaaga tgacatcatg ggatagtttc acattgtatg tagtttcact gcttgtgtgg   9360 gggggataa atgaagagct tacaatgtca cattcatcat ccttcccatc aagtggtttt   9420
catgaaggac acctccggac aaaggctatg ggatatgtgt tctttactta gacccttctt   9480
ggagctgatt tgtgatgtct cggactgtaa aaactggatt gcttttctgc cttttagca    9540 tcacaaaaag aaatgcatcc caaggaagaa ggttctatca atgctaattt ctaaaaagag   9600
cttgcagggt cagaacctca ccaaccctca ctagtctctg cagagaaaat actacacagg   9660
tgtgataaga gagcacaaag aagctggaga agcaaagatt tgctcagcct cacactaagg   9720
aactgttgac tctgtcctgg gactcctctc tgctccctca ttcattgtca gaatctgtgc   9780
ccaagaggga tgagaagtgg tcagaaatgg ctttgttgat ttagtttgtc atcttcaccc   9840
acttctgcca agcagtgaag ggatcaggac atcaattta gcccatttgt agttttggga    9900
agatcctttc ccttctctga tggtggagat ggtttcatct ctacagtcac ctcccaccca   9960
ggagtgaggc cttcagctga ctcagtcaca ccgacctctc ttctcctgaa tttagggagt   10020
cttttcactg atgctgatca gtactatgtt ggaacttggc ctggctgtcc tcactgccat   10080
gctgtggtgg aaacagagtc actctaacat ccctgggtg agtattctaa aggcctcctg   10140
aatcttcctg atatttctct gggacatgtt ggtctatgct gtcatgaatg gcagatagaa   10200
tgaaatcagt cacaatgaca tgaatatcag gtgatttgga cagggaggtg ggacagtagg   10260
tgatggggta gaaggtaatt gtgtagctga tgagagctat ctagacatgg aaacagacaa   10320
accatgttct tcccttccct attgcaaaca aagaaactga ggttctgaga agttaaatat   10380
atatcccgac attgtgatga atttgcctgt gtttggaatg ttcaagtgta gctgcctccc   10440
ctctaactag gaatactttc tcctacagca actagtctct ttaacaatct tgacctgata   10500
```

-continued

```
aagacaaatt gcacactgga gtgtattcag tcagcatctt aggatatgtt tttcttcctt    10560
ctgatattac tttatttctt gcataaagac actaaggaaa taatgtttgt taattgcatg    10620
caaccgttct cagccagctc gaggggtttg cttcagtaat tgaaccgaaa agctttgctc    10680
tgaccagacc tttatttaga gtgtggaaag gagaggagat gatatatata tatcaaatat    10740
atatatcaca taaggtgtgc tagtctcacc ttggaatatc tacaacattg aatgaaattc    10800
tatcatgtat atacatgtgc ctatgtatct atcttccgtc ctatatgcat aaacatatgt    10860
atgcatatat gtatatatat atatatgtat tcattcacaa tctgaaacca catattttct    10920
tttttctaga atgttatgtt cctgccacat agctcaaata atgactccaa catggaatca    10980
aaggtacttt gtaacccctc atatgaggaa caattggttt gttaagaaaa acaaaacaaa    11040
acaaaactaa ataccacaaa aacaaatgga actataccgc agaagatatg tcttcatgat    11100
aatgcagaaa ttccaaccat cacagggtag caatgcttgc tacttaaaat gtagactgtt    11160
catacagtgg gtaccagtat gagttgaatg tgtgtattac tggcacccta ttgattttca    11220
tgaccttggc ttcagccaaa gcccagacct acaaatggtg gcctttctta gaaaaccaaa    11280
cagaatgttt caggccattg tagtggggaa aagggacaac attttcttgc cccctgcaat    11340
taacagcaac agttaaccat tagcagtctt tgtattcaga atctctgcta tgacgtgggt    11400
cttctatcat atcagtttta ttcactggtg tgaataaaca agggacctgc aatgaagtct    11460
gaagaagttt ccatgttgtt ggttcaaaat aaagtctttt tgtgattgta tattctttt    11520 gtatggggtt ttgtgtgggt tttgttgttg ttgttgtttt gcttttatgc acagatcaag    11580
tcctcagtgg tacataaaca catgtgtttg ctattttttt tttgttctct atcaaccaaa    11640
aaaaaaaaaa aaaaaggcat gggaaagaga aaaaggaata tatctgtgtc tctgtgttta    11700
tgtggtgtgt gtgtgtgtgt gttttaaact aaaactgaat gaacattcaa agtttagcaa    11760
tgtattttgg aggtaccaga taacatactt atttctagaa tcgccagagc aaatgagaga    11820
cattttgtcg cttcttataa gaggc                                          11845
```

```
<210> SEQ ID NO 10
<211> LENGTH: 2759
<212> TYPE: DNA
<213> ORGANISM: Mus musculus
<220> FEATURE:
<221> NAME/KEY: CDS
<222> LOCATION: (99)..(806)

<400> SEQUENCE: 10
ggtattcaga gccaacccat cttaactgcc catccagagc acaccgcatt tctgtgtaac       60
agtatctttc attcctggat agcccaatta atgaaaaa atg gac aca gaa aat agg      116
                                        Met Asp Thr Glu Asn Arg
                                          1               5 agc aga gca gat ctt gct ctc cca aat cca caa gaa tcc tcc agt gca        164
Ser Arg Ala Asp Leu Ala Leu Pro Asn Pro Gln Glu Ser Ser Ser Ala
            10               15               20 cct gac att gaa ctc ttg gaa gca tct cct gcc aaa gca gcc cca cca        212
Pro Asp Ile Glu Leu Leu Glu Ala Ser Pro Ala Lys Ala Ala Pro Pro
        25               30               35 aag cag aca tgg cgg aca ttt ttg aag aaa gag ttg gag ttc ctg gga        260
Lys Gln Thr Trp Arg Thr Phe Leu Lys Lys Glu Leu Glu Phe Leu Gly
    40               45               50 gca aca caa att ctg gtt ggt ttg ata tgc ctt tgt ttt gga aca att        308
Ala Thr Gln Ile Leu Val Gly Leu Ile Cys Leu Cys Phe Gly Thr Ile
55               60               65               70
```

-continued

```
gtc tgc tcc gta ctc tat gtt tca gac ttt gat gaa gaa gtg ctt tta        356
Val Cys Ser Val Leu Tyr Val Ser Asp Phe Asp Glu Glu Val Leu Leu
                75                  80                  85 ctt tat aaa cta ggc tat cca ttc tgg ggt gca gtg ctg ttt gtt ttg        404
Leu Tyr Lys Leu Gly Tyr Pro Phe Trp Gly Ala Val Leu Phe Val Leu
                90                  95                  100 tct gga ttt ttg tca att atc tcc gaa aga aaa aac aca ttg tat ctg        452
Ser Gly Phe Leu Ser Ile Ile Ser Glu Arg Lys Asn Thr Leu Tyr Leu
                105                 110                 115 gtg aga ggc agc ctg gga gca aac att gtc agt agc atc gct gca ggg        500
Val Arg Gly Ser Leu Gly Ala Asn Ile Val Ser Ser Ile Ala Ala Gly
        120                 125                 130 acg ggg atc gcc atg ctg atc ctc aat ctg acc aat aac ttc gct tat        548
Thr Gly Ile Ala Met Leu Ile Leu Asn Leu Thr Asn Asn Phe Ala Tyr
135                 140                 145                 150 atg aac aac tgc aag aat gta acc gaa gac gac ggc tgc ttt gtg gct        596
Met Asn Asn Cys Lys Asn Val Thr Glu Asp Asp Gly Cys Phe Val Ala
                155                 160                 165 tct ttc acc aca gaa ctg gtg ttg atg atg ctg ttt ctc acc atc ctg        644
Ser Phe Thr Thr Glu Leu Val Leu Met Met Leu Phe Leu Thr Ile Leu
                170                 175                 180 gcc ttt tgc agt gct gtg ttg ttc act atc tat agg att gga caa gag        692
Ala Phe Cys Ser Ala Val Leu Phe Thr Ile Tyr Arg Ile Gly Gln Glu
                185                 190                 195 tta gaa agt aaa aag gtc cca gat gat cgt ctt tat gaa gaa tta aat        740
Leu Glu Ser Lys Lys Val Pro Asp Asp Arg Leu Tyr Glu Glu Leu Asn
        200                 205                 210 gtg tat tca cca att tac agt gag ttg gaa gac aaa ggg gaa aca tct        788
Val Tyr Ser Pro Ile Tyr Ser Glu Leu Glu Asp Lys Gly Glu Thr Ser
215                 220                 225                 230 tct cca gtt gat tca taa gaatcagggg accaggacaa tctgattcaa             836
Ser Pro Val Asp Ser
                235 gtataatctt gaaagttgat cttttacaa aattctcgca aaatttctgt ttgttccaca      896 ttctgtcagt ttttcaattg gattgttctg cagatgccac tcttttagtt atgctgtatc     956 tgatcttcta aatatctccc tttttgcgga tatcattcac tccaatttc ttgtttttgtg    1016 tcacaatttc acatacatct tttctggaaa gtcatcaagg aataagttgg ctttattgta    1076 tgtctacttt catgaacaaa aggaagatat ggaagaatta ccctgagaat ttaactaacc    1136 ttagataatc aggtaatatt tggctcttag ttcattttag aattctcaac agctatagtt    1196 atatgtgata tatatccacc atatcaagcc ttctgtatgt attttaacat gatatacact    1256 tttctgtgta gatatattttc caccctcaat aataatgggg ttattttaga gacataaagc   1316 tttgtgaaaa gacgacatca tctggttgat gagtacattc acctgcacag gtatcgctca    1376 gtggtttgcc aattggtgag tagtaggcaa tagagaacat tatcaaacca ttcagtctag    1436 tgagatggat aggtacattc agggatactg tgagtatcct ttagtaagac acatgggaag    1496 aatgaagaat aaactgatga agacttgagc tagaaggtag tcaatgggaa tgacaagaaa    1556 tgattgtgta taacacatgt acgtaaatat ctaccaaaag ttggtagaga ttggcatgtt    1616 tgcctagaat ctcagcacaa ggccagcctc tgttacatag tgagttagag gccagcctgg    1676 ctatatgata tcctacatca aaggaccaaa ggagaaattg gttcaagttg ttaatacctt    1736 aaaggatagt taaacaaaca gcagtttgat atattcagtg tttgattctt taataaaact    1796 aaatgaataa cattgagggg gagggaagca gtaatgtaga agtctggatg gtggaagagt    1856 agtagagaca acttaaaact cagttttaga cttttgttct gagatgggta taagagtgat    1916
```

-continued

```
cattaaataa ggagggaaga caccaggaga attattttga gatagaacta aggcagtcaa    1976
actccacatg cctacactta gaaggggaaa gtaaggatca aaagtagaaa ccctaacaag    2036
tcaggtaagc atattacaga acattaacca gcagatgcct atagtgggga aaagttagac    2096
aaagcgaaaa taattaccca ccagagaccg tgcatgtagg cttgggaaag acaagagaaa    2156
atagcaactc caaatgaatg ctaactctga agagggtgtg ggcagaggac cagaacattt    2216
gcaaaggtgc ccagagagca gaccatgaat agaaggtagt gaggaaaaac aaacaaacaa    2276
acaaacaaac acccccaaaa cagctgagaa aatgattttg ttgctcctat taagattttt    2336
aaaagaaaca aaaagagatg ttgaaaaatc tgtttgctgg gatcagttgg tgtgttctcc    2396
atgtgtccaa gggacaggta acttttctaa atcttcatgt aaggctcgcc tcatttacat    2456
ccgtctctcc acacagccat atcctcaatt cacagttact ctatcacggt agtaaactgt    2516
gcgtgtgatc tccttatgta tcttcaggca gtgtttatcc agtaaatcag agttatttaa    2576
cttgatattt gtattagcaa atgaagttga aagaatatga gggaagtctt gaggaagaaa    2636
atcgatggtg gatatgatca tatttcactg tacacatttg taaagttctc agaaataaag    2696
aaaactcatt ttaaaaagaa ccatgtacat taaaacaatt gattaaatgg tgccaaggac    2756
aaa                                                                  2759
```

<210> SEQ ID NO 11
<211> LENGTH: 235
<212> TYPE: PRT
<213> ORGANISM: Mus musculus

<400> SEQUENCE: 11

```
Met Asp Thr Glu Asn Arg Ser Arg Ala Asp Leu Ala Leu Pro Asn Pro
1               5                   10                  15

Gln Glu Ser Ser Ser Ala Pro Asp Ile Glu Leu Leu Glu Ala Ser Pro
            20                  25                  30

Ala Lys Ala Ala Pro Pro Lys Gln Thr Trp Arg Thr Phe Leu Lys Lys
        35                  40                  45

Glu Leu Glu Phe Leu Gly Ala Thr Gln Ile Leu Val Gly Leu Ile Cys
    50                  55                  60

Leu Cys Phe Gly Thr Ile Val Cys Ser Val Leu Tyr Val Ser Asp Phe
65                  70                  75                  80

Asp Glu Glu Val Leu Leu Leu Tyr Lys Leu Gly Tyr Pro Phe Trp Gly
                85                  90                  95

Ala Val Leu Phe Val Leu Ser Gly Phe Leu Ser Ile Ile Ser Glu Arg
            100                 105                 110

Lys Asn Thr Leu Tyr Leu Val Arg Gly Ser Leu Gly Ala Asn Ile Val
        115                 120                 125

Ser Ser Ile Ala Ala Gly Thr Gly Ile Ala Met Leu Ile Leu Asn Leu
    130                 135                 140

Thr Asn Asn Phe Ala Tyr Met Asn Asn Cys Lys Asn Val Thr Glu Asp
145                 150                 155                 160

Asp Gly Cys Phe Val Ala Ser Phe Thr Thr Glu Leu Val Leu Met Met
                165                 170                 175

Leu Phe Leu Thr Ile Leu Ala Phe Cys Ser Ala Val Leu Phe Thr Ile
            180                 185                 190

Tyr Arg Ile Gly Gln Glu Leu Glu Ser Lys Lys Val Pro Asp Asp Arg
        195                 200                 205

Leu Tyr Glu Glu Leu Asn Val Tyr Ser Pro Ile Tyr Ser Glu Leu Glu
```

-continued

```
            210             215             220

Asp Lys Gly Glu Thr Ser Ser Pro Val Asp Ser
225                 230                 235

<210> SEQ ID NO 12
<211> LENGTH: 8200
<212> TYPE: DNA
<213> ORGANISM: Mus musculus

<400> SEQUENCE: 12
ggtattcaga gccaacccat cttaactgcc catccagagc acaccgcatt tctgtgtaac        60
agtatctttc attcctggat agcccaatta atgaaaaaat ggacacagaa aataggagca       120
gagcagatct tgctctccca aatccacaag aatcctccag gtaagcaaag actatttttt       180
tttcattgaa gttatttatc aagacagaaa ttcacagtgc tgggcatgca gatgccaatt       240
catagattta ttcacagatt ccagtaagtt acttaagttt cttagtgtct tactctctta       300
gcagttggga acaaggcttt tacttcactt gaaaactgga gatatcagat tttctaacat       360
tagagacttg tgctttttggg tatgagacag ggagtttgaa catacagatc tcatgcctct       420
gtatatagag ctcacaggat ttacaaaatg atcttgatcc tggttggccc ttgtgcttag       480
ggcatgggat cctgcaccca agattgaaat aggaatagag actgagctag ctcctcaaag       540
cagtcctctg catatgaagt tgtacacggc ctttattgac agagcacatg cagaaacatt       600
tctatgctaa aacctgtttg aggctgacag gcgggcatat cataagacag agatttaaga       660
aagaacttat ggaaacccag gatgaacgag agcatgcagc attttttttt tgtttgtttg       720
ttctattatg gtctatgtaa acacttggat aatgttcaag tgttgatggt tggttgcttt       780
gactctctga gacttttctc aggcaccaca ccagagagtt caactgcgtg attctcttga       840
ggaacaacta acacacaatg ctccagattc agacagttaa gaacatcaca cagggagtta       900
gaagattttt gtatgattaa gttttttgtaa atttcagtgc acctgacatt gaactcttgg       960
aagcatctcc tgccaaagca gccccaccaa agcagacatg gcggacattt ttgaagaaag      1020
agttggagtt cctgggagtg agtgcctggc ctttattctc aactcaaaat gcaggctggc      1080
tctaggacag agtatttagt tatattaaca ttttctctca tgggctgatg gtgtcctata      1140
gcattcttga taggcgagga attgacggta ttatttgcac actctgggaa gagaaaagca      1200
ttttcttata aagacattaa gttgctaggt catgaatgga aaacaggaat gaaggataca      1260
aaatgtctcc tgttagttag atagaaagaa caattatgca tgcctgacat aagtatgcaa      1320
ataaagctgt gtgtgacatg tattgataat gtatgcgtta gagtctgcta gtcatggctc      1380
aggatatata gtgaatagaa gacagtggac aaatctcaca aatgggtcaa tccaaggaaa      1440
gcctatgata ccaaacagat tttgcatatt cagtcttaca gagaaattgg tacaattttg      1500
agaaaataga tcctaacttt ataaaattca tgttttccac aggcaacaca aattctggtt      1560
ggtttgatat gcctttgttt tggaacaatt gtctgctccg tactctatgt ttcagacttt      1620
gatgaagaag tgctttttact ttataaacta ggctatccat tctggggtgc agtgctggtg      1680
agaacatatc tgtaattgtt tctgaaataa tgctaagcag agattttctt ttaatcaaag      1740
ctaattaatt ttcttttaat caagtgctta tctctagcat ttcaataata tctacagttc      1800
ttcatttata tatacatagc atctctaaat gtagtttcca aagcactttc cacatatact      1860
cattaacaag agcaaaagat tcttatcaca gttaactgtg gttataaaac cattaacata      1920
ctttcattga ctgaaaaact tgacactcta tgaaactgta aaagaataaa tacataaata      1980
```

-continued

```
tttaaaagtt aaatgactga agacttatat tcaagaaaat acccttaaca ctacctagta    2040
ataaaactac ctggtatatg tacttacata tattttatcc attaataaaa aataagattg    2100
aagagtggcc ttagtagtta aggatgcttg ctgctcttcc acaggacctg agttcagttc    2160
ttagtaccat gtcatgtgca tatggctgcc agtgactctt gctcaaggag ataagaacct    2220
tcttctggcc ttcttgggcc ttcatacaga ttagcatata tacacacaga catatacaca    2280
cactagcaca tatatgtttt taaaaatcta aaacaataca atagtgtaaa aagttatctt    2340
taagaatgga ggggaaagac atatttcaga tgagaacaaa gttaacaaca ttggatgaac    2400
acaattcctt ttaaaaattc tactgtctag aaagcaaatg actgaatgag attacaaggt    2460
catatagcct tgtatctgtg tagtacacat acaataaata gcatattctg catatagaag    2520
gtgtaagatt tgagaaaatt tgactcatat atatgtacat atatatatac atatatatgt    2580
atatataaaa tattagctta tatctcaacc tcattattac aagcctatcc atgattttgt    2640
aagttacatt catttcccta caactcttcc tgtcccactc tgctaccaga cttctcatct    2700
tgaagcaatc actataattg aaaattagtt ttcaattttt acagctttgt aggaaaagaa    2760
ctgtatgcta caatgtttta tatgcctacc tttcttcatt catatcatca ttgtgtatta    2820 tcttttatc aatagttaag ttataaaaat gtattcaaat ctaaggaaac cattgcattg    2880
gtttgatatg ctgctatgta gttcttcgat ctcctggtca tatggccaag aatcatcttg    2940
accatttacc acattttcct tgaaatttct ttccattttt caaagatttc atttttaaaaa    3000 tttattcatt tattctctct ctctctgtat gtgtatgtat gtctctgtct ctgtctctgt    3060
ctctgtctct gtctctgtct ctctctctct ctctccctct ctctctctct ctctcgtgtg    3120
tgtgtgtgtg tgtgtgtgtg tgtgtgtgtg tgtgtgtatg taccagtgcc atagctcacg    3180
tagaggtcag atgtcagaga acaactgtaa gatgtcaggt cttttttttgc tactttgtga    3240 gatcaaaaaa ttgaacttgg gttctgttac aagcacttct acccactggg gcatctcata    3300
gactcaagct cctgactctt taagtgtcta ggaacacaaa tctcaatttc ttagaaggta    3360
gtctgatttt gaagcttcaa gttttactt ttactagata tttgcaaatg tatattttca    3420
tagttaacta tatgaccatg tgctgcatat cagactccat agctacacaa ggctggcctg    3480
aagaagctga cagtgtaagt caggacatat gaactaagca ttacaataaa tgagaccact    3540
gttacagtta tacagcagat atcactagcc cttgctatct gcccagtagg tatcaaagtc    3600
aaccttatag aggagccatg taaacaaaaa aaaaaaaaaa aaacaaacaa acaaaaaaaa    3660
aaaacgaaga gcctcgggtc atctaagacc taatgagtag gagcctatgt gcttcttttg    3720 cttcttttc tctttcttac agtgtagctc aggctttcct catccgtaca accttcctgc    3780
ctcagactcc tgagagctgg gattgcaggc atgtgccacc acacagcttg gaacttgtat    3840
tttatcagga gtttcacatg gtctgtataa ggaattggct ttgagaaata tttttacagga    3900 gataataaat aatggtctca tgggagattt tagtggatag ccttctagaa catctaaaac    3960
tcatttttat attttgagga taggcgaaaa agtacaccag agagcagaaa ctcactttgg    4020
tctctcccct gtttccttt ggacagtttg ttttgtctgg attttttgtca attatctccg    4080 aaagaaaaaa cacattgtat ctggtgagtt gcactcatgt tattcattct tccaaggtaa    4140
gaaaagtaaa attgtagggg tgttaagaga ggcacacgag aatcaactac attatagaga    4200
gtgtagatgt gtgctttttt cccccatctc tttgtgctgg aaagcatttt tgcaagataa    4260
actggataaa atcgttagaa acataaattg tgtcaccttaa taaacagtga aatttgatta    4320
ctttgatacc atttaaaggg acccacacag gtattgtctt tgtatgtatt tatagtctct    4380
```

-continued

```
tttagttaag tcaattgaga tgacttgagg ataaactacg catgcatata tgtctttttt      4440
ttttcttatc ctggagattg aacctctgac cttttgcaat gcctcactct gtgttcactg      4500
ctgagtacat ccccagccct tattcttttc ttgaatgcat ctcagaggga aacatgctta      4560
ccaggtgttg agtatatttg caagagtccc ctatttaact ggggtttgga accagttttg      4620
agttactata caggaccagc tctgtaagac agatcagttg gtcagctgct gccacaccca      4680
gtcccagggc tgaatgttct atgccatcag gtgagaggca gcctgggagc aaacattgtc      4740
agtagcatcg ctgcagggac ggggatcgcc atgctgatcc tcaatctgac caataacttc      4800
gcttatatga acaactgcaa gaatgtaacc gaagacgacg gctgctttgt ggcttctttc      4860
accacagtat gtatttctta tgaaaacact aactctctgg gtcctgtctt aagtgtgaaa      4920
acccttcctc ttccagagac accgtcctcc ctttggaatc tccatctcta aaatagagtt      4980
ctgtactaag gaggtaatgg tcttactcct actcctggcc acattcctta aggttggagt      5040
catcacctcc aatcagtcac ttcctggttt cctatttatg tatcagtgtg ttatgtctgc      5100
tcttaagctt cagagttcct gagaaagggg gtgcttctct aagggaagcg attgggggta      5160
catccacctg tgactttcac ttttttcgttg gttgctgttt gacaggaact ggtgttgatg      5220
atgctgtttc tcaccatcct ggccttttgc agtgctgtgt tgttcactat ctataggatt      5280
ggacaagagt tagaaagtaa aaaggtcagt aggaaatctt gactagcgta tgctggagaa      5340
tttgtgcttt attcttttag aacatgtcct gaattttctg aaattattgg ctggaaaact      5400
atttctcaaa aaactggctc ttgtatctca tattggagat cttattttat acactgaaat      5460
ggcatgagat cacagcacag tcctgtgagg ttaggcaaat ggaactgtta tcattgtaga      5520
cattgtgggt gctctggaga ggttgggtgt gagaagtgag ttatcagcag tgtgtgatgg      5580
aaacattcag ctgttgggct tttctttttt ttgggggggg ggagcttgtt atatttgttt      5640
ctgttctctc cctttctttt atatatatct ttcccctctt tattgctctc aaaaaagcct      5700
taggtttggc ttatctctta gttcatggtg acaactgtgt tttcacctgc tgcacaaact      5760
cattatattc ttggtgagaa tttccaattc tcagccactg ttgctaactc aaatctgaca      5820
aatggaacct acaacccact ctctatgtcc acttttagac acagcccagt tgttacactt      5880
cttagtgacc actgtcttca gtcagaagag aaaccaacat tttagatata gagtaacctc      5940
aataacttgt cacttacata gtttctttta gcccccattg gccaacccat ctgatctagt      6000
ttctggacat taaaggtcca gacactccag gatcatgaga ggcaaggtga aattcaaaaa      6060
gatagataga agagatgcat ccatgatgag acttctagaa atgtaaagat ctgggtaatt      6120
gatatgggac gttttttctc tttatcaggt cccagatgat cgtctttatg aagaattaaa      6180
tgtgtattca ccaatttaca gtgagttgga agacaaaggg gaaacatctt ctccagttga      6240
ttcataagaa tcaggggacc aggacaatct gattcaagta taatcttgaa agttgatctt      6300
tttacaaaat tctcgcaaaa tttctgtttg ttccacattc tgtcagtttt tcaattggat      6360
tgttctgcag atgccactct tttagttatg ctgtatctga tcttctaaat atctcccttt      6420
ttgcggatat cattcactcc aatttttcttg ttttgtgtca caatttcaca tacatctttt      6480
ctggaaagtc atcaaggaat aagttggctt tattgtatgt ctactttcat gaacaaaagg      6540
aagatatgga agaattaccc tgagaattta actaacctta gataatcagg taatatttgg      6600
ctcttagttc attttagaat tctcaacagc tatagttata tgtgatatat atccaccata      6660
tcaagccttc tgtatgtatt ttaacatgat atacacttttt ctgtgtagat atatttccac      6720
```

-continued

```
cctcaataat aatggggtta tttttagagac ataaagcttt gtgaaaagac gacatcatct    6780
ggttgatgag tacattcacc tgcacaggta tcgctcagtg gtttgccaat tggtgagtag    6840
taggcaatag agaacattat caaaccattc agtctagtga gatggatagg tacattcagg    6900
gatactgtga gtatccttta gtaagacaca tgggaagaat gaagaataaa ctgatgaaga    6960
cttgagctag aaggtagtca atgggaatga caagaaatga ttgtgtataa cacatgtacg    7020
taaatatcta ccaaaagttg gtagagattg gcatgtttgc ctagaatctc agcacaaggc    7080
cagcctctgt tacatagtga gttagaggcc agcctggcta tatgatatcc tacatcaaag    7140
gaccaaagga gaaattggtt caagttgtta ataccttaaa ggatagttaa acaaacagca    7200
gtttgatata ttcagtgttt gattctttaa taaaactaaa tgaataacat tgaggggggag    7260 ggaagcagta atgtagaagt ctggatggtg gaagagtagt agagacaact taaaactcag    7320
ttttagactt ttgttctgag atgggtataa gagtgatcat taaataagga gggaagacac    7380
caggagaatt attttgagat agaactaagg cagtcaaact ccacatgcct acacttagaa    7440
ggggaaagta aggatcaaaa gtagaaaccc taacaagtca ggtaagcata ttacagaaca    7500
ttaaccagca gatgcctata gtggggaaaa gttagacaaa gcgaaaataa ttacccacca    7560
gagaccgtgc atgtaggctt gggaaagaca agagaaaata gcaactccaa atgaatgcta    7620
actctgaaga gggtgtgggc agaggaccag aacatttgca aaggtgccca gagagcagac    7680
catgaataga aggtagtgag gaaaaacaaa caaacaaaca aacaaacacc cccaaaacag    7740
ctgagaaaat gattttgttg ctcctattaa gattttttaaa agaaacaaaa agagatgttg    7800
aaaaatctgt ttgctgggat cagttggtgt gttctccatg tgtccaagggg acaggtaact    7860 tttctaaatc ttcatgtaag gctcgcctca tttacatccg tctctccaca cagccatatc    7920
ctcaattcac agttactcta tcacggtagt aaactgtgcg tgtgatctcc ttatgtatct    7980
tcaggcagtg tttatccagt aaatcagagt tatttaactt gatatttgta ttagcaaatg    8040
aagttgaaag aatatgaggg aagtcttgag gaagaaaatc gatggtggat atgatcatat    8100
ttcactgtac acatttgtaa agttctcaga aataaagaaa actcatttta aaaagaacca    8160
tgtacattaa aacaattgat taaatggtgc caaggacaaa                          8200
```

```
<210> SEQ ID NO 13
<211> LENGTH: 20
<212> TYPE: DNA
<213> ORGANISM: Homo sapiens

<400> SEQUENCE: 13
gaggactcag ctggaaccaa                                                    20

<210> SEQ ID NO 14
<211> LENGTH: 20
<212> TYPE: DNA
<213> ORGANISM: Homo sapiens

<400> SEQUENCE: 14
ggcagacaga gcactcagaa                                                    20

<210> SEQ ID NO 15
<211> LENGTH: 328
<212> TYPE: DNA
<213> ORGANISM: Homo sapiens

<400> SEQUENCE: 15
atgagaccat catagtgctc ccatcaaatg tcatcaactt ctcccaagca gagaaacccg      60
```

-continued

```
aacccaccaa ccaggggcag gatagcctga agaaacatct acacgcagaa atcaaagtta      120
ttgggactat ccagatcttg tgtggcatga tggtattgag cttggggatc attttggcat      180
ctgcttcctt ctctccaaat tttacccaag tgacttctac actgttgaac tctgcttacc      240
cattcatagg accctttttt tttatcatct ctggctctct atcaatcgcc acagagaaaa      300
ggttaaccaa gcttttggtg catagcag                                         328
```

```
<210> SEQ ID NO 16
<211> LENGTH: 189
<212> TYPE: DNA
<213> ORGANISM: Homo sapiens

<400> SEQUENCE: 16
atgagaccat catagtgctc ccatcaaatg tcatcaactt ctcccaagca gagaaacccg       60
aacccaccaa ccaggggcag gatagcctga agaaacatct acacgcagaa atcaaagtta      120
ttgggtttat catctctggc tctctatcaa tcgccacaga gaaaaggtta accaagcttt      180
tggtgcata                                                              189
```

```
<210> SEQ ID NO 17
<211> LENGTH: 203
<212> TYPE: PRT
<213> ORGANISM: Homo sapiens

<400> SEQUENCE: 17

Met Thr Ser Gln Pro Val Pro Asn Glu Thr Ile Ile Val Leu Pro Ser
1               5                   10                  15

Asn Val Ile Asn Phe Ser Gln Ala Glu Lys Pro Glu Pro Thr Asn Gln
            20                  25                  30

Gly Gln Asp Ser Leu Lys Lys His Leu His Ala Glu Ile Lys Val Ile
            35                  40                  45

Gly Phe Ile Ile Ser Gly Ser Leu Ser Ile Ala Thr Glu Lys Arg Leu
        50                  55                  60

Thr Lys Leu Leu Val His Ser Ser Leu Val Gly Ser Ile Leu Ser Ala
65                  70                  75                  80

Leu Ser Ala Leu Val Gly Phe Ile Ile Leu Ser Val Lys Gln Ala Thr
                85                  90                  95

Leu Asn Pro Ala Ser Leu Gln Cys Glu Leu Asp Lys Asn Asn Ile Pro
            100                 105                 110

Thr Arg Ser Tyr Val Ser Tyr Phe Tyr His Asp Ser Leu Tyr Thr Thr
            115                 120                 125

Asp Cys Tyr Thr Ala Lys Ala Ser Leu Ala Gly Thr Leu Ser Leu Met
        130                 135                 140

Leu Ile Cys Thr Leu Leu Glu Phe Cys Leu Ala Val Leu Thr Ala Val
145                 150                 155                 160

Leu Arg Trp Lys Gln Ala Tyr Ser Asp Phe Pro Gly Ser Val Leu Phe
                165                 170                 175

Leu Pro His Ser Tyr Ile Gly Asn Ser Gly Met Ser Ser Lys Met Thr
            180                 185                 190

His Asp Cys Gly Tyr Glu Glu Leu Leu Thr Ser
        195                 200
```

```
<210> SEQ ID NO 18
<211> LENGTH: 198
<212> TYPE: PRT
<213> ORGANISM: Homo sapiens
```

<400> SEQUENCE: 18

Met Asp Thr Glu Ser Asn Arg Arg Ala Asn Leu Ala Leu Pro Gln Glu
1               5                   10                  15

Pro Ser Ser Val Pro Ala Phe Glu Val Leu Glu Ile Ser Pro Gln Glu
            20                  25                  30

Val Ser Ser Gly Arg Leu Leu Lys Ser Ala Ser Ser Pro Pro Leu His
        35                  40                  45

Thr Trp Leu Thr Val Leu Lys Lys Glu Gln Glu Phe Leu Phe Ser Ile
        50                  55                  60

Ser Gly Met Leu Ser Ile Ile Ser Glu Arg Arg Asn Ala Thr Tyr Leu
65                  70                  75                  80

Val Arg Gly Ser Leu Gly Ala Asn Thr Ala Ser Ser Ile Ala Gly Gly
                85                  90                  95

Thr Gly Ile Thr Ile Leu Ile Ile Asn Leu Lys Lys Ser Leu Ala Tyr
            100                 105                 110

Ile His Ile His Ser Cys Gln Lys Phe Phe Glu Thr Lys Cys Phe Met
        115                 120                 125

Ala Ser Phe Ser Thr Glu Ile Val Val Met Met Leu Phe Leu Thr Ile
        130                 135                 140

Leu Gly Leu Gly Ser Ala Val Ser Leu Thr Ile Cys Gly Ala Gly Glu
145                 150                 155                 160

Glu Leu Lys Gly Asn Lys Val Pro Glu Asp Arg Val Tyr Glu Glu Leu
                165                 170                 175

Asn Ile Tyr Ser Ala Thr Tyr Ser Glu Leu Glu Asp Pro Gly Glu Met
                180                 185                 190

Ser Pro Pro Ile Asp Leu
        195

<210> SEQ ID NO 19
<211> LENGTH: 250
<212> TYPE: DNA
<213> ORGANISM: Homo sapiens

<400> SEQUENCE: 19
gtctttacaa atgctggttt tcatcctcaa tctcactttc tcttcccaca gactatccag        60
atcttgtgtg gcatgatggt attgagcttg gggatcattt tggcatctgc ttccttctct       120
ccaaatttta cccaagtgac ttctacactg ttgaactctg cttacccatt cataggaccc       180
ttttttgtga gtagagtttc tgaggagggc aggatggggc aaagagggga ggaagatgcc       240
aatagcttag                                                              250

<210> SEQ ID NO 20
<211> LENGTH: 76
<212> TYPE: DNA
<213> ORGANISM: Homo sapiens

<400> SEQUENCE: 20
gtctttacaa atgctggttt tcatcctcaa tctcactttc tcttcccaca gactatccag        60
atcttgtgtg gcatga                                                        76

<210> SEQ ID NO 21
<211> LENGTH: 89
<212> TYPE: DNA
<213> ORGANISM: Homo sapiens

<400> SEQUENCE: 21

-continued

```
ttacccattc ataggaccct tttttgtgag tagagtttct gaggagggca ggatggggca      60
aagaggggag gaagatgcca atagcttag                                        89

<210> SEQ ID NO 22
<211> LENGTH: 25
<212> TYPE: DNA
<213> ORGANISM: Homo sapiens

<400> SEQUENCE: 22
tctggatagt ctgtgggaag agaaa                                            25

<210> SEQ ID NO 23
<211> LENGTH: 50
<212> TYPE: DNA
<213> ORGANISM: Homo sapiens

<400> SEQUENCE: 23
tcaatctcac tttctcttcc cacagactat ccagatcttg tgtggcatga                 50

<210> SEQ ID NO 24
<211> LENGTH: 25
<212> TYPE: DNA
<213> ORGANISM: Homo sapiens

<400> SEQUENCE: 24
gccctcctca gaaactctac tcaca                                            25

<210> SEQ ID NO 25
<211> LENGTH: 50
<212> TYPE: DNA
<213> ORGANISM: Homo sapiens

<400> SEQUENCE: 25
ttacccattc ataggaccct tttttgtgag tagagtttct gaggagggca                 50

<210> SEQ ID NO 26
<211> LENGTH: 28
<212> TYPE: DNA
<213> ORGANISM: Homo sapiens

<400> SEQUENCE: 26
atagatatat actcacaaat atggctcc                                         28
```

1

EXON SKIPPING OF FC-EPSILON-RI-BETA AND MS4A6A IN COMBINATION FOR THE TREATMENT OF ALLERGIC DISEASES

CROSS-REFERENCE TO RELATED PATENT APPLICATIONS

This application claims benefit of U.S. Provisional Application Ser. No. 62/932,664, filed Nov. 8, 2019, the disclosure of which is incorporated herein by reference in its entirety.

GRANT STATEMENT

This invention was made with government support under grant number ES025128 awarded by the National Institutes of Health. The government has certain rights in the invention.

TECHNICAL FIELD

The presently disclosed subject matter relates to the use of antisense oligonucleotides to modulate cell surface expression of FcεRIβ protein, thereby modulating IgE-mediated immune responses. More particularly, the presently disclosed subject matter relates in some embodiments to compositions and methods for modulating cell surface expression of FcεRIβ protein by inducing exon skipping in both FcεRIβ and MS4A6A pre-mRNAs.

BACKGROUND

More than 30 million people in the United States suffer from asthma and prevalence is increasing. Most asthma therapies rely on dampening inflammation with glucocorticosteroids and relieving airway constriction with beta-agonists. More directed approaches that target the source of inflammation are needed. Mast cells play a key role in allergic asthma through the release of mediators that drive inflammation and directly induce bronchoconstriction in response to IgE-directed antigens. Mast cells infiltrate key structures in the lung such as submucosal glands, airway epithelium and the airway smooth muscle (ASM) bundles in asthma. Mast cell infiltration into the ASM in asthma is likely critical for the development of airway hyperresponsiveness since this key feature is one of the only immunopathological differences evident in asthmatics compared to patients with eosinophilic bronchitis, which is phenotypically similar to asthma except these patients do not exhibit airway hyperresponsiveness. This feature of asthma strongly implicates mast cells as the driver of airway hyperresponsiveness. However, emerging asthma therapies attempt to combat the effects of individual pleiotropic mediators or induce immune tolerance, which can be either ineffective or have serious adverse effects. None of the currently available drugs to treat asthma specifically target mast cell function.

SUMMARY

Rather than the administration of β-agonists, glucocorticoids, or allergen to produce hypersensitization, the presently disclosed subject matter relies on a different approach, namely altering cellular responses to IgE-directed antigens. This approach is based on the finding that one or more genes at human 11q12-q13 are strongly linked to allergy and asthma susceptibility, and the knowledge that the MS4A gene family is clustered around 11q12-q13. It is also known that the gene MS4A1, which encodes the protein CD20, and MS4A2, which encodes the FcεRIβprotein, are associated with activation and proliferation of B-cells and mast cells, respectively. Furthermore and as disclosed herein, the human MS4A6A gene (also referred to herein and in the literature as the human MS4A6 gene) is also located within this region of human chromosome 11. Thus, these genes are considered candidates for the linkage of these genetic regions with allergy.

As such, the presently disclosed subject matter provides in some embodiments antisense oligomers comprising 10 to 50 linked nucleosides, wherein the antisense oligomers are targeted to a region of a pre-mRNA molecule encoding an MS4A6A protein or a region of a pre-mRNA molecule encoding an FcεRIβ protein. The targeted regions may comprise sequences involved in splicing of the MS4A6A-encoding pre-mRNA and/or the FcεRIβ-encoding pre-mRNA such that hybridization of the antisense oligomer to the MS4A6A-encoding pre-mRNA and/or the FcεRIβ-encoding pre-mRNA alters splicing of the MS4A6A-encoding pre-mRNA and/or the FcεRIβ-encoding pre-mRNA. Hybridization of the antisense oligomer to the MS4A6A-encoding pre-mRNA and/or the FcεRIβ-encoding pre-mRNA may in some embodiments reduce cell surface expression of a high affinity IgE receptor (FcεRI).

In some embodiments, the targeted region comprises at least a portion of a polynucleotide sequence selected from the group consisting of an intron sequence, an exon sequence, a sequence comprising an intron/exon junction, a splice donor sequence, a slice acceptor sequence, a splice enhancer sequence, a splice branch point sequence, a polypyrimidine tract, and/or an exon encoding a first transmembrane domain. In some embodiments, the targeted region of the MS4A6A-encoding pre-mRNA may comprise a polynucleotide sequence selected from an intron 3 sequence, an exon 4 sequence, a sequence comprising an intron 3/exon 4 junction, an exon 4 splice donor sequence, an exon 4 slice acceptor sequence, an exon 4 splice enhancer sequence, an exon 4 splice branch point sequence, or an exon 4 polypyrimidine tract. In some embodiments, the targeted region of the pre-mRNA comprises a polynucleotide sequence encoding the first transmembrane domain of the target protein.

In some embodiments, one or more antisense oligomers are targeted to regions of an MS4A6A-encoding pre-mRNA transcribed from an MS4A6A gene (a "MS4A6A pre-mRNA"), and in some embodiments one or more antisense oligomers are targeted to regions of an FcεRIβ-encoding pre-mRNA transcribed from an MS4A2 gene (a "MS4A2 pre-mRNA"). The MS4A6A and FcεRIβ proteins encoded by the transcription products may be from any mammal, including in some embodiments a human, in some embodiments a mouse, in some embodiments a dog, in some embodiments a cat, and in some embodiments a horse (e.g., the encoded MS4A6A and/or FcεRIβ protein may be a human MS4A6A and/or FcεRIβ protein, a murine MS4A6A and/or FcεRIβ protein, a canine MS4A6A and/or FcεRIβ protein, a feline MS4A6A and/or FcεRIβ protein, or an equine MS4A6A and/or FcεRIβ protein, or an MS4A6A and/or FcεRIβ protein from any other mammal). In some embodiments, the MS4A6A pre-mRNA and/or the FcεRIβ pre-mRNA encodes a human MS4A6A protein and/or FcεRIβ protein, respectively. In some embodiments, the human MS4A6A pre-mRNA comprises SEQ ID NO: 3 or a subsequence thereof. In some embodiments, the murine MS4A6 pre-mRNA comprises SEQ ID NO: 9 or a subsequence thereof. In some embodiments, the human MS4A6A protein comprises SEQ ID NO: 2 or a subsequence thereof. In some embodiments, the murine MS4A6 protein comprises SEQ ID NO: 8 or a subsequence thereof. In some embodiments, the human MS4A2 pre-mRNA comprises SEQ ID NO: 6 or a subsequence thereof. In some embodiments, the murine MS4A2 pre-mRNA comprises SEQ ID NO: 12 or a subsequence thereof. In some embodiments, the human MS4A2 protein comprises SEQ ID NO: 5 or a subsequence thereof. In some embodiments, the murine MS4A6A protein comprises SEQ ID NO: 11 or a subsequence thereof. In some embodiments, the murine MS4A6 nucleotide sequence corresponds to one of Accession NOs. NM_027209.3, NM_028595.4, and NM_026835.2 of the GENBANK® biosequence database, which encode the proteins disclosed as Accession Nos. NP_081485.2, NP_082871.2, and NP_081111.1 of the GENBANK® biosequence database, respectively.

Hybridization of antisense oligomers as set forth herein to MS4A6A pre-mRNAs and/or MS4A2 pre-mRNAs in some embodiments result in the production of a mature MS4A6A or MS4A2 mRNA molecule that lacks a portion or all of exon 4 (MS4A6A) or exon 3 (MS4A2) of the mature MS4A6A mRNA and/or the MS4A2 mRNA, respectively. In some embodiments, hybridization of an antisense oligomer as set forth herein to an MS4A2 pre-mRNA results in production of an mRNA molecule encoding a truncated FcεRIβ protein. The truncated FcεRIβ protein may be t-FcεRIβ. In some embodiments, hybridization of an antisense oligomer as set forth herein to an MS4A6A pre-mRNA and/or to an MS4A2 pre-mRNA results in reduced localization of an FcεRIβ protein to the membrane of a cell expressing high affinity IgE receptor (FcεRI).

In some embodiments, the presently disclosed subject matter provides antisense oligomers comprising 10 to 50 linked nucleosides, wherein the 10 to 50 linked nucleosides comprise a targeting nucleic acid sequence sufficiently complementary to a target nucleic acid sequence in an MS4A6A-encoding pre-mRNA and/or an MS4A2-encoding pre-mRNA, such that the oligomer specifically hybridizes to the target sequence.

Hybridization of the antisense oligomer to the MS4A6A-encoding pre-mRNA and/or the MS4A6A-encoding pre-mRNA alters splicing of the pre-mRNA. Hybridization of the antisense oligomer to the MS4A6A-encoding pre-mRNA and/or the MS4A6A-encoding pre-mRNA in some embodiments reduces cell surface expression of high affinity IgE receptor (FcεRI).

In some embodiments, the targeting sequence in the antisense oligomer comprises at least 6 contiguous nucleobases fully complementary to at least 6 contiguous nucleobases in the target sequence, wherein the target sequence is a subsequence of any one of SEQ ID NOs: 3, 6, 9, and 12. The targeting sequence in the antisense oligomer may be at least 80% complementary over its entire length to an equal length of contiguous nucleobases in the target sequence. The targeting sequence may comprise at least a portion of a polynucleotide sequence selected from an intron sequence, an exon sequence, a sequence comprising an intron/exon junction, a splice donor sequence, a slice acceptor sequence, a splice enhancer sequence, a splice branch point sequence, a polypyrimidine tract, and/or an exon encoding a first transmembrane region. In some embodiments, the polynucleotide sequence is an MS4A2 sequence that is selected from an intron 2 sequence, an exon 3 sequence, a sequence comprising an intron 2/exon 3 junction, an exon 3 splice donor sequence, an exon 3 slice acceptor sequence, an exon 3 splice enhancer sequence, an exon 3 splice branch point sequence, an exon 3 polypyrimidine tract, an exon encoding the first transmembrane domain of MS4A2, or a combination thereof. In some embodiments, the polynucleotide sequence is an MS4A6A sequence that is selected from an intron 3 sequence, an exon 4 sequence, a sequence comprising an intron 3/exon 4 junction, an exon 4 splice donor sequence, an exon 4 slice acceptor sequence, an exon 4 splice enhancer sequence, an exon 4 splice branch point sequence, an exon 4 polypyrimidine tract, an exon encoding the first transmembrane domain of MS4A6A, or a combination thereof.

In some embodiments, the target nucleic acid sequences may be in an MS4A6A-encoding pre-mRNA transcribed from an MS4A6A gene. The encoded MS4A6A protein may be from any mammal, including a human, a mouse, a dog, a cat, or a horse. In some embodiments, the MS4A6A pre-mRNA encodes a human MS4A6A protein. In some embodiments, the target nucleic acid sequences may be in an MS4A6A-encoding pre-mRNA transcribed from an MS4A2 gene. The encoded MS4A6A/FcεRIβ protein may be from any mammal, including a human, a mouse, a dog, a cat, or a horse. In some embodiments, the MS4A2 pre-mRNA encodes a human FcεRIβ protein.

The presently disclosed antisense oligomers can in some embodiments comprise, consist essentially of, or consist of 10 to 50 linked nucleosides, wherein the 10 to 50 linked nucleosides comprise, consist essentially of, or consist of a nucleic acid sequence at least partially complementary to a target nucleic acid sequence in a pre-mRNA molecule, which encodes a protein comprising in some embodiments SEQ ID NO: 2, in some embodiments SEQ ID NO: 5, in some embodiments SEQ ID NO: 8, and in some embodiments SEQ ID NO: 11. The protein may be encoded by an MS4A6A transcript comprising either of SEQ ID NOs: 1 and 7 or an MS4A2 transcript comprising either of SEQ ID NOs: 4 and 10. In some embodiments, hybridization of the antisense oligomer to the pre-mRNA may alter splicing of the pre-mRNA. Hybridization of the antisense oligomer to the pre-mRNA may reduce cell surface expression of high affinity IgE receptor (FcεRI). In some embodiments, an antisense oligomer of the presently disclosed subject matter targets an MS4A6A gene product, and in some embodiments the antisense oligomer comprises, consists essentially of, or consists of SEQ ID NO: 22. In some embodiments, an antisense oligomer of the presently disclosed subject matter targets an MS4A2 gene product, and in some embodiments the antisense oligomer comprises, consists essentially of, or consists of SEQ ID NO: 26.

In some embodiments, the MS4A6A target sequence may comprise at least a portion of a polynucleotide sequence selected from the group consisting of SEQ ID NOs: 1, 3, 7, and 9, or an MS4A2 sequence comprising a portion of a polynucleotide sequence selected from the group consisting of SEQ ID NOs: 4, 6, 10, and 12. The portion may be at least 10 contiguous nucleotides. The target sequence may comprise a sequence at least 90% identical to a sequence selected from the group consisting of at least a portion of a polynucleotide sequence selected from the group consisting of SEQ ID NOs: 1, 3, 4, 6, 7, 9, 10, and 12.

In some embodiments, the MS4A6A targeting sequence or the MS4A2 targeting sequence may comprise at least 10 contiguous nucleobases that are fully complementary in sequence to at least 10 contiguous nucleobases in a sequence selected from SEQ ID NOs: 1, 3, 4, 6, 7, 9, 10, and 12. The targeting sequence may comprise a sequence at least 80% identical to a nucleotide sequence that is complementary to at least a portion of a sequence selected from SEQ ID NO: 1, 3, 4, 6, 7, 9, 10, and 12. Exemplary, non-limiting MS4A2 target and targeting sequence are disclosed in U.S. Patent Application Publication No. 2019/0062756, which is incorporated by reference in its entirety, including the Sequence Listing.

These antisense oligomers may be in some embodiments an antisense RNA molecule, which in some embodiments further comprises a modification selected from a nucleoside modification, an internucleoside modification, a sugar modification, a sugar-internucleoside linkage modification, and combinations thereof. Such modifications may increase resistance to degradation of the antisense RNA molecule by a ribonuclease. A morpholino oligomer is an exemplary, non-limiting modified antisense oligomer.

In some embodiments, the presently disclosed subject matter also provides expression vectors that express an antisense oligomer as set forth herein, while in some embodiments the presently disclosed subject matter relates to pharmaceutical compositions comprising, consisting essentially of, or consisting of an antisense oligomer as set forth herein.

In some embodiments, the presently disclosed subject matter relates to methods for modulating splicing of MS4A6A and/or MS4A2 mRNAs (for example, pre-mRNAs) in a cell by contacting the cell with one or more antisense oligomers, expression vectors, and/or compositions as set forth herein, thereby modulating splicing of the MS4A6A and/or MS4A2 mRNA. The amount of full-length MS4A6A-encoding and/or MS4A2-encoding mRNA produced by the cell may be reduced by in some embodiments at least 50%, in some embodiments at least 60%, in some embodiments at least 70%, in some embodiments at least 80%, in some embodiments at least 90%, in some embodiments at least 95%, in some embodiments at least 97%, and in some embodiments at least 99%, or in some embodiments can be completely eliminated.

In some embodiments, the presently disclosed subject matter relates to methods for reducing cell surface expression of FcεRI in a cell. In some embodiments, the presently disclosed methods comprise contacting the cell with at least one antisense oligomer, expression vector, or composition as set forth herein, thereby reducing expression of FcεRI on the surface of the cell. The amount of FcεRI expressed on the cell surface may be reduced by in some embodiments at least 50%, in some embodiments at least 60%, in some embodiments at least 70%, in some embodiments at least 80%, in some embodiments at least 90%, in some embodiments at least 95%, in some embodiments at least 97%, in some embodiments at least 99%, or in some embodiments can be completely eliminated. In some embodiments, the at least one antisense oligomer modulates splicing of an MS4A6A mRNA. In some embodiments, the at least one antisense oligomer modulates splicing of an MS4A2 mRNA. In some embodiments, the presently disclosed method comprises contacting the cell with at least two antisense oligomers, expression vectors, and/or compositions as set forth herein, wherein the at least two antisense oligomers, expression vectors, and/or compositions comprise at least one first antisense oligomer that modulates splicing of an MS4A6A mRNA and at least one second antisense oligomer that modulates splicing of an MS4A2/FcεRIβ mRNA. In some embodiments, the at least one first antisense oligomer comprises, consists essentially of, or consists of SEQ ID NO: 22. In some embodiments, the at least one second antisense oligomer targets an MS4A2 gene product, and in some embodiments the antisense oligomer comprises, consists essentially of, or consists of SEQ ID NO: 26.

In some embodiments, the presently disclosed subject matter relates to methods for modulating FcεRI receptor complex-dependent degranulation in a mast cell. In some embodiments, the presently disclosed methods comprise contacting the mast cell with at least one antisense oligomer, expression vector, and/or composition as set forth herein, thereby modulating FcεRI receptor complex-dependent degranulation in the mast cell. FcεRI receptor complex-dependent degranulation may be reduced by in some embodiments at least 50%, in some embodiments at least 60%, in some embodiments at least 70%, in some embodiments at least 80%, in some embodiments at least 90%, in some embodiments at least 95%, in some embodiments at least 97%, in some embodiments at least 99%, or in some embodiments can be completely eliminated. In some embodiments, the presently disclosed method comprises contacting the mast cell with at least two antisense oligomers, expression vectors, and/or compositions as set forth herein, wherein the at least two antisense oligomers, expression vectors, and/or compositions comprise at least one first antisense oligomer that modulates splicing of an MS4A6A mRNA and at least one second antisense oligomer that modulates splicing of an MS4A2/FcεRIβ mRNA. In some embodiments, the at least one first antisense oligomer comprises, consists essentially of, or consists of SEQ ID NO: 22. In some embodiments, the at least one second antisense oligomer targets an MS4A2 gene product, and in some embodiments the antisense oligomer comprises, consists essentially of, or consists of SEQ ID NO: 26.

In some embodiments, the presently disclosed subject matter relates to methods for modulating FcεRI receptor complex-dependent mast-cell migration. In some embodiments, the presently disclosed methods comprise contacting the mast cell with at least one antisense oligomer, expression vector, and/or composition as set forth herein, thereby modulating FcεRI receptor complex-dependent degranulation in the mast cell. FcεRI receptor complex-dependent degranulation may be reduced by in some embodiments at least 50%, in some embodiments at least 60%, in some embodiments at least 70%, in some embodiments at least 80%, in some embodiments at least 90%, in some embodiments at least 95%, in some embodiments at least 97%, in some embodiments at least 99%, or in some embodiments can be completely eliminated. In some embodiments, the presently disclosed method comprises contacting the mast cell with at least two antisense oligomers, expression vectors, and/or compositions as set forth herein, wherein the at least two antisense oligomers, expression vectors, and/or compositions comprise at least one first antisense oligomer that modulates splicing of an MS4A6A mRNA and at least one second antisense oligomer that modulates splicing of an MS4A2/FcεRIβ mRNA. In some embodiments, the at least one first antisense oligomer comprises, consists essentially of, or consists of SEQ ID NO: 22. In some embodiments, the at least one second antisense oligomer targets an MS4A2 gene product, and in some embodiments the antisense oligomer comprises, consists essentially of, or consists of SEQ ID NO: 26.

In some embodiments, the presently disclosed subject matter relates to methods for modulating cytokine release. In some embodiments, the presently disclosed methods comprise contacting a cytokine-producing cell with at least one antisense oligomer, expression vector, and/or a composition as set forth herein, thereby modulating cytokine release. The cytokine may be in some embodiments a vasoactive amine, in some embodiments a proteoglycan, in some embodiments a protease, in some embodiments a growth factor, in some embodiments a chemokine, in some embodiments a pro-inflammatory lipid mediator, in some embodiments a histamine, in some embodiments a serotonin, in some embodiments heparin, in some embodiments tryptase, in some embodiments chymase, in some embodiments TNFα, in some embodiments IL-1, in some embodiments IL-6, in some embodiments IL-8, in some embodiments IL-10, in some embodiments TNFα, in some embodiments VEGF, in some embodiments TGFβ, in some embodiments CCL2-4, in some embodiments a prostaglandin, and/or in some embodiments a leukotriene. The amount of at least one cytokine released may be reduced by in some embodiments at least 50%, in some embodiments at least 60%, in some embodiments at least 70%, in some embodiments at least 80%, in some embodiments at least 90%, in some embodiments at least 95%, in some embodiments at least 97%, in some embodiments at least 99%, or in some embodiments can be completely eliminated. These methods may be performed on a cell in culture or in the body of an individual.

In some embodiments, the presently disclosed subject matter relates to methods for inhibiting an anaphylactic reaction in an individual by administering to the individual at least one antisense oligomer, expression vector, and/or composition as set forth herein.

In some embodiments, the presently disclosed subject matter relates to methods for treating allergic conditions in individuals by administering one or more antisense oligomers, expression vectors, and/or composition as set forth herein, to an individual in need of such treatment. The allergic condition treated may be asthma, atopic dermatitis, chronic rhinitis, chronic sinusitis, and/or allergic conjunctivitis.

In some embodiments, the presently disclosed subject matter relates to methods for reducing the incidence and/or severity of an allergic reaction in an individual by administering one or more antisense oligomers, expression vectors, and/or compositions as set forth herein to an individual acutely and/or chronically experiencing allergic reactions or at risk of having an allergic reaction.

In some embodiments, the presently disclosed subject matter relates to methods for treating an individual at risk of developing an anaphylactic reaction by administering one or more antisense oligomers, expression vectors, and/or compositions as set forth herein to the individual at risk of developing an anaphylactic reaction.

In some embodiments, the presently disclosed subject matter relates to methods for treating a mast cell-related disease in an individual comprising administering one or more antisense oligomers, expression vectors, and/or compositions as set forth herein to an individual in need of such treatment. The mast cell-related disease may be mastocytosis, or a mast cell tumor, including mastocytoma.

In some embodiments, the individuals to whom the one or more antisense oligomers, expression vectors, and/or compositions as set forth herein are administered is to a mammal, optionally a human, mouse, dog, cat, or horse.

Accordingly, it is an object of the presently disclosed subject matter to provide compositions and methods for modulating expression of MS4A6A and MS4A2 gene products. This and other objects are achieved in whole or in part by the presently disclosed subject matter.

An object of the presently disclosed subject matter having been stated above, other objects and advantages of the presently disclosed subject matter will become apparent to those of ordinary skill in the art after a study of the following description of the presently disclosed subject matter and non-limiting EXAMPLES and Figures

BRIEF DESCRIPTION OF THE FIGURES

FIG. 1A: RT-PCR of FcεRIβ in human LAD2 cells demonstrated efficient exon skipping with a shift in size of 150 basepairs (bp) from the full length product (FL-FcεRIβ) to the truncated product (t-FcεRIβ). β-actin was used as a control. FIG. 1B: Transfection of FcεRIβ SSO into LAD2 cells resulted in a 58% reduction in surface FcεRI expression without affecting KIT expression. Black bars: control; gray bars: FcεRIβ SSO. FIG. 1C: FcεRIβ SSO transfection slightly, but significantly reduced IgE-dependent mast cell degranulation. Black circles: control; gray circles: FcεRIβ SSO. FIG. 1D: $Ca^{2+}$ influx was not significantly affected by FcεRIβ SSOs in LAD2. Black circles: control; gray circles: FcεRIβ SSO. Data are mean±SEM from at least 3 independent experiments. Statistics: two way ANOVA and Sidak's post-test. $p < 0.01$; *$p < 0.001$; ****$p < 0.0001$; n.s. not significant.

FIG. 2A: The majority of the MS4A gene family contain multiple splice variants. Thus, primers for all of the MS4A gene family were designed to amplify a region of mRNA that was identical between all known variants. MS4A6A amplified two (2) bands and sequencing and cloning experiments determined that mast cells expressed a novel truncation of MS4A6A. FIG. 2B: Mast cells expressed MS4A4 variant 1 and variant 3. FIG. 2C: Graphic representation of the MS4A gene family members with full length (FL) and truncated (t) splice variants expressed in huMCs. A combination of splice variant-specific RT-PCR, cloning of open reading frames, and sequencing were employed to determine expression. TM1-TM4: transmembrane domains 1-4, respectively. ITAM: immunoreceptor tyrosine-based activation motif, depicted with dark gray boxes. Light gray boxes: exons.

FIGS. 4A and 4B: Transfection of human mast cells with GFP FcεRIβ and MS4A6A constructs showed good GFP expression. FIG. 4C: Western blots from the transfected mast cells showed that an anti-MS4A6A (α-MS4A6) antibody bound to MS4A6A but not FcεRIβ α-β-actin: β-actin detected with an anti-β-actin antibody: FIG. 4D. shRNA knockdown of MS4A6A resulted in reduced expression of both MS4A6A splice variants. β-actin: β-actin loading control. FIGS. 4E and 4F: Quantification of protein expression by Western blot (FIG. 4E) agreed with mRNA expression assessed by QPCR with shMS4A6A treatment (FIG. 4F). FIGS. 4G and 4H: shMS4A6A modestly, but significantly, reduced human mast cell degranulation (FIG. 4G) and calcium influx (FIG. 4H) in response to IgE crosslinking (XL). Black symbols: control: white symbols: shMS4A6. FIG. 4I: shMS4A6A reduced surface FcεRIα expression by roughly 40%. These data appeared to mirror the data of FcεRIβ SSO treatment reported previously (Cruse et al., 2016).

FIG. 5A: SSOs targeting either FcεRIβ or MS4A6A efficiently and specifically induced exon skipping of each mRNA. Double SSOs efficiently skipped both mRNAs. FIGS. 5B and 5C: Cell number and viability were not significantly affected by skipping. FIG. 5D: Surface FcεRIα expression was reduced by skipping either FcεRIβ 60%) or MS4A6A (40%), but skipping both significantly increased the reduction in receptor expression at the surface (80%). FIG. 5E: Expression of the α and γ subunits of FcεRI were not affected by exon skipping, suggesting that the reduced FcεRIα surface expression was due to trafficking. FIGS. 5F and 5G: Exon skipping either FcεRIβ or MS4A6A alone was ineffective at reducing degranulation, but exon skipping both mRNAs markedly reduced degranulation (FIG. 5F) in response to IgE XL, but not in response to compound 48/80 (FIG. 5G) that acts through the GPCR MRGX2 receptor.

FIGS. 6A-6D. To confirm the role of FcεRIβ and MS4A6A in human mast cells was also applicable to primary cells, cord blood-derived mast cells were employed. CBDMCs are immature cells that require priming with IL-4 to express FcεRIα on the surface and to degranulate in response to IgE XL. FIG. 6E: Once primed, exon skipping of FcεRIβ (dark gray; second from left in each group) and MS4A6A (light gray; third from left in each group) was comparable to LAD2 cells, except that CBDMCs were more sensitive to single skipping of both proteins as compared to skipping of both proteins together (medium gray; far right in each group). This was likely due to the low expression level of surface FcεRIα (see FIG. 6C) in these immature cells. FIG. 6F. IgE-independent activation was examined by adding ionomycin and this was unaffected by SSOs. Example experiment shown. Black bars: control (far left in each group); Dark gray bars: FccRIα skipping alone (second from left in each group). Light gray bars: MS4A6 skipping alone (third from left in each group). Medium gray bars: FcεRIα and MS4A6 skipping together (far right in each group).

FIG. 8A. IL-8 cytokine release from CBDMCs in response to IgE XL presented as pg/ml. FIG. 8B. Due to variation between CBDMC donors in the amount of cytokine released in response to IgE XL, data was analyzed as percent inhibition with SSO treatment for each donor, which effectively normalize the data for each donor. These data showed that inhibition of cytokine production was only significantly induced when FcεRIβ (dark gray bars; second from left in each group) was targeted or when both FcεRIβ and MS4A6 was targeted (medium gray bars; far left in each group), but not when MS4A6 alone (light gray bars; third from left in each group) was targeted. Data are the mean±SEM from three experiments.

BRIEF DESCRIPTION OF THE SEQUENCE LISTING

Figure 1A:
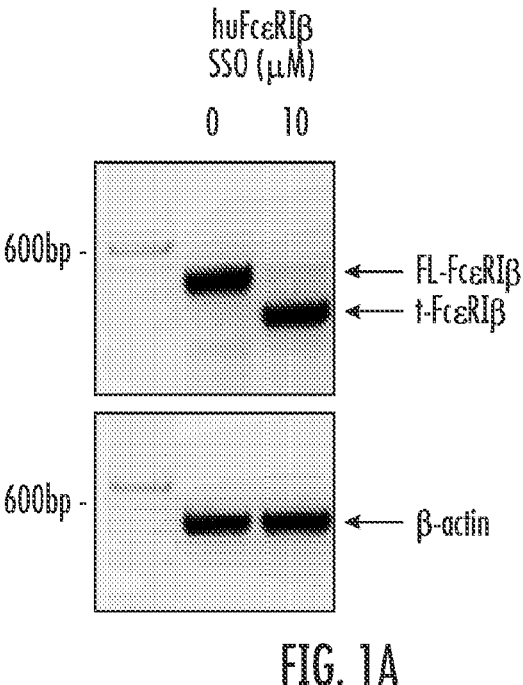
FIGS. 1A-1D. Human FcεRIβ Splice Switching Oligonucleotides (SSOs) are ineffective at reducing FcεRI function.

SEQ ID NO: 1 is the nucleotide sequence of an exemplary human MS4A6A gene product of the presently disclosed subject matter. It corresponds to Accession No. NM_152852.3 of the GENBANK® biosequence database.

SEQ ID NO: 2 is the amino acid sequence encoded by SEQ ID NO: 1. It corresponds to Accession No. NP_690591.1 of the GENBANK® biosequence database. The protein that corresponds to SEQ ID NO: 2 includes four (4) transmembrane domains, which include amino acids 49-71 (transmembrane domain 1; TM1), amino acids 86-105 (transmembrane domain 2; TM2), 112-134 (transmembrane domain 3; TM3), and amino acids 180-202 (transmembrane domain 4; TM4).

SEQ ID NO: 3 is an exemplary nucleotide sequence the human MS4A6A genomic locus. It corresponds to the reverse complement of nucleotides 60,171,607-60,184,666 of Accession No. NC_000011.10 of the GENBANK® biosequence database.

SEQ ID NO: 4 is the nucleotide sequence of an exemplary human MS4A2 gene product of the presently disclosed subject matter. It corresponds to Accession No. NM_000139.5 of the GENBANK® biosequence database.

SEQ ID NO: 5 is the amino acid sequence encoded by SEQ ID NO: 4. It corresponds to Accession No. NP_000130.1 of the GENBANK® biosequence database.

SEQ ID NO: 6 is an exemplary nucleotide sequence the human MS4A2 genomic locus. It corresponds to nucleotides 60,088,664-60,098,467 of Accession No. NC_000011.10 of the GENBANK® biosequence database.

SEQ ID NO: 7 is the nucleotide sequence of an exemplary murine MS4A6A gene product of the presently disclosed subject matter. It corresponds to Accession No. NM_027209.3 of the GENBANK® biosequence database.

SEQ ID NO: 8 is the amino acid sequence encoded by SEQ ID NO: 7. It corresponds to Accession No. NP_081485.2 of the GENBANK® biosequence database.

SEQ ID NO: 9 is an exemplary nucleotide sequence the murine MS4A6A genomic locus. It corresponds to nucleotides 11,518,519-11,530,403 of Accession No. NC_000085.6 of the GENBANK® biosequence database.

SEQ ID NO: 10 is the nucleotide sequence of an exemplary murine MS4A2 gene product of the presently disclosed subject matter. It corresponds to Accession No. NM_013516.2 of the GENBANK® biosequence database.

SEQ ID NO: 11 is the amino acid sequence encoded by SEQ ID NO: 10. It corresponds to Accession No. NP_038544.1 of the GENBANK® biosequence database.

SEQ ID NO: 12 is an exemplary nucleotide sequence the murine MS4A2 genomic locus. It corresponds to the reverse complement of nucleotides 11,615,520-11,623,719 of Accession No. NC_000085.6 of the GENBANK® biosequence database.

SEQ ID NOs: 13 and 14 are the sequences of exemplary oligonucleotide primers that can be employed to amplify a 472 basepair (bp) subsequence of the exemplary human MS4A6A gene product of SEQ ID NO: 1.

SEQ ID NO: 15 is the nucleotide sequence of exons 3-6 of the exemplary human MS4A6A gene product of SEQ ID NO: 1.

SEQ ID NO: 16 is the nucleotide sequence of the exemplary human MS4A6A gene product of SEQ ID NO: 1 after targeting designed to delete exon 4. It corresponds to exon 3 fused to exons 5 and 6 of SEQ ID NO: 1.

SEQ ID NO: 17 is the predicted amino acid sequence encoded by the exemplary human MS4A6A gene product of SEQ ID NO: 1 after targeting designed to delete exon 4. It corresponds to the amino acid sequence encoded by SEQ ID NO: 16, and also corresponds to amino acids 1-49 of SEQ ID NO: 2 fused to amino acids 95-247 of SEQ ID NO: 2.

SEQ ID NO: 18 is the predicted amino acid sequence encoded by the exemplary human MS4A2 gene product of SEQ ID NO: 4 after targeting designed to delete exon 3. It corresponds to amino acids 1-61 of SEQ ID NO: 5 fused to amino acids 108-244 of SEQ ID NO: 5.

SEQ ID NO: 19 presents an exemplary sequence with possible targets for oligo design (SEQ ID NO: 19) with respect to the human MS4A6A transcription products.

SEQ ID NOs: 20 and 21 present additional exemplary target sequences to target the human MS4A6A transcription products, and correspond to nucleotides 1-76 of SEQ ID NO: 19 and nucleotides 162-250 of SEQ ID NO: 19, respectively. In some embodiments, subsequences of SEQ ID NOs: 20 and 21 can be employed as exemplary target sequences, including but not limited to nucleotides 27-76 of SEQ ID NO: 20 and nucleotides 1-40 of SEQ ID NO: 21.

SEQ ID NOs: 22-25 present exemplary targeting and target sequences for targeting exon 4 of the human MS4A6A gene product. SEQ ID NO: 22 is the nucleotide sequence of an exemplary oligonucleotide employed in the targeting experiments disclosed herein, which can target a human MS4A6A gene product comprising SEQ ID NO: 23, and SEQ ID NO: 24 is the nucleotide sequence of an exemplary oligonucleotide that can target a human MS4A6A gene product comprising SEQ ID NO: 25.

SEQ ID NO: 26 is the nucleotide sequence of an exemplary oligonucleotide employed in the MS4A2 targeting experiments disclosed herein.

DETAILED DESCRIPTION

FcεRIβ Splice Switching Oligonucleotides (SSOs) eliminate critical protein-protein interactions resulting in loss of surface FcεRI expression in mouse mast cells (MCs), but are less efficient in human cells (Cruse et al., 2016). It is possible that, in humans, FcεRIβ-like proteins from the same gene family as FcεRIβ (i.e., the MS4A gene family) can compensate for FcεRIβ, to act as novel regulators of, and potential subunits for FcεRI. It was found that human (hu)MCs express FcεRIβ (MS4A2), MS4A4, and MS4A6A, and it is possible that MS4A6A stabilizes surface expression of FcεRI and initiates signaling through a C-terminal hemi-ITAM exhibiting redundancy with FcεRIβ. It is also possible that MS4A4 functions in FcεRI signaling, but through a distinct mechanism from that of FcεRIβ and MS4A6A. MS4A4 does not contain an ITAM or hemi-ITAM and thus likely does not trigger signaling in the same way as FcεRIβ or MS4A6A. Rather, it is possible that MS4A4 promotes recruitment of FcεRI complexes into lipid rafts to amplify signaling through PLCγ1, increasing Ca$^{2+}$ release from stores and Store-Operated Ca$^{2+}$ Entry (SOCE). Overall, and while not wishing to be bound by any particular theory of operation, in addition to the known function of FcεRIβ in trafficking FcεRI to the cell surface, FcεRIβ-like proteins could dynamically interact with FcεRI at the plasma membrane in humans to regulate FcεRI and MC responses to IgE. Particularly, and as disclosed herein, it has been established that FcεRIβ and MS4A6A proteins compete to associate with FcεRI and promote distinct signaling complexes through their ITAM and hemi-ITAM motifs, respectively.

The presently disclosed subject matter not only elucidates novel functions for understudied genes, but also facilitates translation of the presently disclosed therapeutic approaches to allergy into humans, to identifying innovative therapeutic targets, and to establishing novel IgE signaling mechanisms. MS4A6A contains a potential hemi-ITAM making it unique within the MS4A family. Therefore, altered ratios of FcεRIβ and MS4A6A in FcεRI complexes could act to fine-tune MC responsiveness in allergic individuals through deregulation of FcεRI on and off signals. In addition, also disclosed herein is that alternative splicing can change protein function and interaction with receptors, adding another layer of regulation.

MCs play a key role in allergic diseases by releasing proinflammatory mediators in response to IgE and antigen (for reviews see Cruse & Bradding, 2016; Virk et al., 2016). However, no currently available drugs directly and specifically target MC function. Disclosed herein is a pioneering therapeutic strategy that utilizes SSOs to induce alternative splicing of FcεRIβ (Cruse et al., 2016). FcεRIβ SSOs target protein-protein interactions resulting in loss of surface FcεRI expression in mice demonstrating potential to improve care for asthma and other allergic diseases. However, FcεRIβ SSOs are less effective in huMCs compared to mouse (mo) MCs (Cruse et al., 2016). The lack of translation to huMCs highlights the need to better understand FcεRI complex formation in each species. In humans and mice, FcεRI are expressed exclusively in MCs and basophils as tetrameric complexes where FcεRIβ subunits are expressed (Küster et al., 1992; Maurer et al., 1994; Kinet, 1999; Kraft et al., 2004). However, in humans FcεRI also exist as trimeric complexes that lack FcεRIβ and are expressed on several cell types (Bieber et al., 1992; Maurer et al., 1994; Maurer et al., 1996; Holloway et al., 2001; Cheung et al., 2010; Dehlink et al., 2010; Vasudev et al., 2012; Greer et al., 2014; Platzer et al., 2015). Mice do not express trimeric FcεRI (Kinet, 1999; Kraft & Kinet, 2007; Gould & Sutton, 2008). Therefore, FcεRIβ may be less critical for FcεRI trafficking in humans and trimeric FcεRI could account for the lack of translation of FcεRIβ SSOs. However, studies in mice with humanized FcεRIα, which express trimeric FcεRI, combined with targeted disruption of FcεRIβ generates mice expressing only trimeric FcεRI, and these mice demonstrate that trimeric FcεRI does not elicit a strong degranulation response or a robust Ca$^{2+}$ signal (Dombrowicz et al., 1998). Therefore, data presented herein are incompatible with trimeric FcεRI and suggested that the low efficacy of FcεRIβ SSOs in huMCs is through a different mechanism.

The suggestion that unidentified FcεRIβ-like proteins could exist and function in human FcεRI was proposed as a caveat of seminal experiments characterizing human and mouse FcεRI (Alber et al., 1991). The data presented herein show that FcεRIβ-like proteins exist. The MS4A genes are a family of 16 genes in humans, that are related to MS4A1 (CD20) and MS4A2 (FcεRIβ), and expressed in immune cells (Liang & Tedder, 2001; Liang et al., 2001). They are 4-pass transmembrane (TM) proteins with similar topology, but low homology to tetraspanins. The MS4A genes cluster around chromosome 11q12-q13 (Liang & Tedder, 2001; Liang et al., 2001), a region linked to allergy and asthma susceptibility (Lympany et al., 1992; Sandford et al., 1993; Stafford et al., 1994). In addition, MS4A2, MS4A4A and MS4A6A have been associated with development of Alzheimer's disease with genome-wide association studies (Hollingworth et al., 2011; Naj et al., 2011). Expression of several MS4A family members have also been implicated in neoplasia (Bangur et al., 2004; Koslowski et al., 2008; Dalerba et al., 2011; Michel et al., 2013; Ye et al., 2014). However, the functions of the MS4A gene cluster are largely unknown, so significance of linkage to disease states remains uncertain. MS4A proteins have been proposed to act as distinct Ca$^{2+}$ channels (Bubien et al., 1993; Koslowski et al., 2008). In addition, MS4A proteins may act as chemoreceptors in olfactory necklace sensory neurons where they recognize various ligands including fatty acids and pheromones to trigger $Ca^{2+}$ responses in these specialized neurons (Greer et al., 2016).

A therapeutic strategy that utilizes exon skipping of a subunit of the high affinity IgE receptor, FcεRIβ, which is critical for trafficking the FcεRI complex to the cell surface, is disclosed in U.S. Patent Application Publication No. 2019/0062756. Exon skipping of FcεRIβ with a Mast cell Targeting Oligonucleotide (MTO) thus eliminates its function in trafficking resulting in loss of surface FcεRI expression and responsiveness to allergens in vitro and in vivo in mice, to specifically target and downregulate mast cells and basophils, which are critical for the immediate allergic response.

The presently disclosed approach utilizes a novel platform for therapeutic antisense oligonucleotides to eliminate trafficking of the IgE receptor to the plasma membrane. The power of this approach is that it targets a protein exclusively expressed in mast cells and basophils enabling the specific targeting of these cells and downregulation of their function. FcεRIβ has been considered as a potential therapeutic target for allergy and asthma, but until the MTO discovery, no viable approach to target this gene with a drug had emerged. Clinical therapeutic utility of antisense oligonucleotides that induce exon skipping has been demonstrated in Duchenne muscular dystrophy where the drugs are well tolerated. However, the use of oligonucleotides to skip mutated exons requires sequencing of patient DNA to identify the causative mutation. Each mutated exon in patients requires clinical trials for the oligonucleotides targeting that exon, slowing drug development and increasing cost. The presently disclosed approach is innovative because skipping of a non-mutant exon is employed to alter the function of a protein by eliminating specific protein-protein interactions that result in altered trafficking and loss of surface expression of a receptor that is critical for an allergic response. Therefore, since a non-mutated exon is targeted, the presently disclosed MTO technology targets the same exon in all patients relieving the burden on development.

However, despite the efficacy of the presently disclosed approach to target FcεRIβ in mouse cells, efficacy in human mast cells is reduced. The reason for the reduced efficacy of targeting FcεRIβ in human cells is not clear, but could be related to fundamental differences between human and mouse FcεRI expression. In both humans and mice, tetrameric FcεRI are expressed exclusively in mast cells and basophils where the FcεRIβ subunit is expressed. However, in humans FcεRI can exist as a trimeric FcεRI complex that lacks FcεRIβ and is expressed on several cell types, while mice appear to lack expression of trimeric FcεRI and thus FcεRI expression is restricted to mast cells and basophils. It has been established the expression of five MS4A genes in mast cells and determined splice variant expression that draws comparisons to FcεRIβ. Exon 3 of FcεRIβ is critical for the function of FcεRIβ in trafficking the FcεRI complex. The highly conserved splicing of the corresponding exons encoding for the 1st and 2nd transmembrane domains of the majority of the MS4A proteins indicates that this exon could also be critical for their trafficking. To examine the importance of alternative splicing of MS4A6A, the same exon skipping methods that were successfully used for FcεRIβ are disclosed herein as applicable to MS4A6A. It was further identified that exon skipping MS4A6A results in reduction of surface FcεRI expression comparable to knockdown of MS4A6A. Quantitative RT-PCR of the other FcεRI subunits, FcεRIα and FcεRIγ revealed that mRNA were not reduced with exon skipping FcεRIβ or MS4A6A and confirmed that the effects were not due to downregulation of gene expression, but rather trafficking of the receptor. These data suggest that the equivalent exon of MS4A6A is comparable to FcεRIβ and thus critical for the function of the full length protein in trafficking FcεRI in human cells. Taken together, these data suggested that FcεRIβ and MS4A6A have partially redundant roles in FcεRI trafficking to the plasma membrane and that targeting either protein alone is insufficient to achieve maximal inhibition of degranulation. However, simultaneous exon skipping of FcεRIβ and MS4A6A results in additive reduction in surface FcεRI expression, which leads to a marked reduction in degranulation.

A novel therapeutic strategy for allergic disease that works well in mouse cells has been identified, but equivalent efficacy in human cells was not observed (see U.S. Patent Application Publication No. 2019/0062756). The mechanism for the reduced efficacy in human cells has been identified and is disclosed herein, and it has been determined that MS4A6A protein can compensate for FcεRIβ in human cells and that this protein can be targeted in the same way as FcεRIβ. Therefore, in order for the presently disclosed therapeutic approach to work in humans, a combination of mast cell-targeting oligonucleotides that target both FcεRIβ and MS4A6A can be employed.

Thus, disclosed herein are novel methods for treating atopic diseases, including methods for treating diseases and syndromes mediated by the high-affinity Fc-epsilon receptor (FcεRI). The presently disclosed subject matter is based in part on the inventors' discovery of a novel, truncated isoform of the FcεRIβ protein (FcεRIβ), which lacks the first and second membrane-spanning regions, and the mRNA transcript for which is truncated in exon 3 (Cruse et al., 2010; see also U.S. Patent Application Publication No. 2019/0062756, the contents of which are incorporated herein by reference in its entirety). This truncated FcεRIβ protein does not traffic to the plasma membrane, resulting in reduced expression of FcεRI on the plasma membrane. The finding of t-FcεRIβ, and its related effects, led to the discovery of selective editing of the FcεRIβ mRNA transcript, using antisense technology, to produce t-FcεRIβ, results in decreased cell-surface expression of the FcεRIβ protein. This in turn leads to a decrease in symptoms resulting from IgE-mediated diseases. Thus, methods and compounds as set forth herein are useful for treating FcεRI-mediated diseases by down-regulating cell-surface expression of FcεRI.

Antisense technology has been demonstrated to be an effective method for modifying the expression levels of gene products (see for example, U.S. Pat. No. 8,765,703, U.S. Pat. No. 8,946,183, and U.S. Patent Publication No. 2015/0376615, which are incorporated herein by reference in their entirety). Antisense technology works by interfering with known steps in the normal processing of mRNA. Briefly, RNA molecules are transcribed from genomic DNA in the nucleus of the cell. These newly synthesized mRNA molecules, called primary mRNA or pre-mRNA, must be processed prior to transport to the cytoplasm for translation into protein at the ribosome. Such processing includes the addition of a 5' methylated cap and the addition of a poly(A) tail to the 3' end of the mRNA.

Maturation of 90-95% of mammalian mRNAs then occurs with splicing of the mRNA. Introns (or intervening sequences) are regions of a primary transcript (or the DNA encoding it) that are not included in the coding sequence of the mature mRNA. Exons (expressed sequences) are regions of a primary transcript (or the DNA encoding it) that remain in the mature mRNA when it reaches the cytoplasm. During the splicing process, exons in the pre-mRNA molecule are spliced together to form the mature mRNA sequence. Splice junctions, also referred to as splice sites, are utilized by cellular apparatus to determine which sequences are removed and where the ends to be joined start and stop. Sequences on the 5' side of the junction are called the 5' splice site, or splice donor site, whereas sequences on the 3' side the junction are referred to as the 3' splice site, or the splice acceptor site. In splicing, the 3' end of an upstream exon is joined to the 5' end of the downstream exon. Thus, the un-spliced RNA (or pre-mRNA) has an exon/intron junction at the 5' end of an intron and an intron/exon junction at the 3' end of an intron. After the intron is removed, the exons are contiguous at what is sometimes referred to as the exon/exon junction or boundary in the mature mRNA. Cryptic splice sites are those which are less often used but may be used when the usual splice site is blocked or unavailable. The use of different combinations of exons by the cell can result in multiple mRNA transcripts from a single gene.

In one application of antisense technology, an antisense oligonucleotide (AON) binds to a mRNA molecule transcribed from a gene of interest and inactivates ("turns off") the mRNA by increasing its degradation or by preventing translation or translocation of the mRNA by steric hindrance. The end result is that expression of the corresponding gene (i.e., final production of the protein encoded by the corresponding gene) is prevented.

Alternatively, antisense technology can be used to affect splicing of a gene transcript. In this application, the antisense oligonucleotide binds to a pre-spliced RNA molecule (pre-messenger RNA or pre-mRNA) and re-directs the cellular splicing apparatus, thereby resulting in modification of the exon content of the spliced mRNA molecule. Thus, the overall sequence of a protein encoded by the modified mRNA differs from a protein translated from mRNA, the splicing of which was not altered (i.e., the full length, wild-type protein). The protein that is translated from the altered mRNA may be truncated and/or it may be missing critical sequences required for proper function. Typically, the compounds used to affect splicing are, or contain, oligonucleotides having a base sequence complementary to the mRNA being targeted. Such oligonucleotides are referred to herein as "antisense oligonucleotides" (AONs).

This disclosure provides antisense technology to modulate splicing of mRNA encoding an FcεRIβ protein, thereby causing a decrease in the amount or "level" of FcεRI protein expressed on the surface of a cell. Accordingly, a method as set forth herein can generally be accomplished by contacting a cell expressing an MS4A2 transcript, with an antisense oligomer targeted to a region of the MS4A2 pre-mRNA. Such contact results in uptake of the antisense oligomer by the cell, hybridization of the oligomer to the MS4A2 mRNA, and subsequent modulation of splicing of the MS4A2 pre-mRNA. In some embodiments, such modulation of splicing of the MS4A2 mRNA decreases cell-surface expression of FcεRI.

The presently disclosed subject matter is not limited to the particular embodiments described herein, as such may vary. Additionally, the terminology used herein is for the purpose of describing particular embodiments only, and is not intended to be limiting on the finally claimed invention, since the scope of the invention will be limited only by the claims.

As used herein and in the appended claims, the singular forms "a," "an," and "the" include plural referents unless the context clearly dictates otherwise. For example, a nucleic acid molecule refers to one or more nucleic acid molecules. As such, the terms "a", "an", "one or more" and "at least one" can be used interchangeably. Similarly, the terms "comprising", "including" and "having" can be used interchangeably. It is further noted that the claims may be drafted to exclude any optional element. As such, this statement is intended to serve as antecedent basis for use of such exclusive terminology as "solely," "only" and the like, in connection with the recitation of claim elements, or use of a "negative" limitation.

As used herein, an MS4A6A gene, MS4A6A, and the like, refer to a gene encoding an MS4A6A protein from a mammal. Examples of MS4A6A genes include, but are not limited to, Accession Numbers NM_152852.3 (human), NM_027209.3 (mouse MS4A6Ab, encoding NP_081485.2), NM_028595.4 (mouse MS4A6Ac, encoding NP_082871.2), and NM_026835.2 (mouse MS4A6Ad, encoding NP_081111.1) of the GENBANK® biosequence database. Similarly, an MS4A6A coding sequence refers to a nucleic acid sequence encoding at least a portion of an MS4A6A protein. Such a portion can be a fragment of the protein (e.g., a 10, 20, 30, 40, 50, 60, 70, 80, 90 or 100 contiguous amino acid segment from any part of the whole protein), an exon, or a domain (e.g., a transmembrane domain), or it can refer to the entire protein, including any splicing variants. MS4A6A genes or coding sequences as set forth herein can be from any mammal having such gene or coding sequence. The MS4A6A gene or coding sequence may be from a human, mouse, canine, feline or equine.

The MS4A6A genomic locus can be found on human chromosome 11 and on mouse chromosome 19. The nucleotide sequences of the human and mouse MS4A6A genomic loci are presented in SEQ ID NOs: 3 and 9, respectively.

As used herein, an MS4A6A transcript is an RNA molecule transcribed from an MS4A6A gene. In some embodiments, MS4A6A transcripts targeted by oligomers as set forth herein are primary transcripts or pre-mRNA molecules. As used herein, primary mRNA or pre-mRNA is an mRNA transcript that has not yet undergone splicing.

Accordingly, a mature mRNA molecule is an mRNA molecule that has undergone splicing.

With respect to the human and mouse MS4A6A genomic loci set forth in SEQ ID NOs: 3 and 9, respectively, intron and exon boundaries for these loci are presented in Table 1.

TABLE 1

| Summary of Human and Mouse MS4A6A Intron/Exon Boundaries | | |
| --- | --- | --- |
| | Nucleotides in SEQ ID NO: 3 | Nucleotides in SEQ ID NO: 9 |
| Exon 1 | 1-125 | 1-116 |
| Intron 1 | 126-1335 | 117-1764 |
| Exon 2 | 1336-1689 | 1765-1927 |
| Intron 2 | 1690-2925 | 1928-3112 |
| Exon 3 | 2926-3086 | 3113-3247 |
| Intron 3 | 3087-4701 | 3248-5251 |
| Exon 4 | 4702-4836 | 5352-5408 |
| Intron 4 | 4837-6350 | 5409-8141 |
| Exon 5 | 6351-6407 | 8142-8339 |
| Intron 5 | 6408-9057 | 8340-10015 |
| Exon 6 | 9058-9265 | 10016-10117 |
| Intron 6 | 9266-11537 | 10118-10929 |
| Exon 7 | 11538-11639 | 10930-11845 |
| Intron 7 | 11640-12413 | |
| Exon 8 | 12414-13060 | |

17

SEQ ID NO: 1 is an exemplary cDNA sequence derived from the human MS4A6A genomic locus. The eight (8) exons noted in Table 1 correspond to the following nucleotide positions of SEQ ID NO: 1: 1-125 (exon 1), 126-478 (exon 2), 479-640 (exon 3), 641-775 (exon 4), 776-832 (exon 5), 833-1042 (exon 6), 1043-1144 (exon 7), and 1145-1791 (exon 8). The initiator codon (ATG) corresponds to nucleotides 494-496 of SEQ ID NO: 1 and the stop codon (TAA) corresponds to nucleotides 1238-1240 of SEQ ID NO: 1. Oligonucleotide primer hMS4A6A-Fw (5'-GAGGACTCAGCTGGAACCAA-3'; SEQ ID NO: 13) corresponds to nucleotides 451-470 of SEQ ID NO: 1, and oligonucleotide primer hMS4A6A-Rv (5'-GGCAGACAGAGCACTCAGAA'3' (SEQ ID NO: 14), which can be used with oligonucleotide primer hMS4A6A-Fw in a polymerase chain reaction (PCR) to amplify subsequences of the human MS4A6A transcript including to assay for deletions in the same, corresponds to the reverse complement of nucleotides 585-877 of SEQ ID NO: 1. By referring to the overlapping antisense oligomer sequences disclosed particularly as SEQ ID NOs: 23-1006 of U.S. Patent Application Publication No. 2019/0062756 and how they relate to the sequence of the human MS4A2 pre-mRNA, one of ordinary skill in the art can design a full panel of antisense oligomers that target human and mouse MS4A6A gene products.

As used herein, an MS4A2 gene, MS4A2, and the like, refer to a gene encoding an FcεRIβ protein from a mammal. Examples of MS4A2 genes include, but are not limited to, Accession Numbers NM_000139.5 (human) and NM_013516.2 (mouse) of the GENBANK® biosequence database. Similarly, an MS4A2 coding sequence refers to a nucleic acid sequence encoding at least a portion of an FcεRIβ protein. Such a portion can be a fragment of the protein (e.g., a 10, 20, 30, 40, 50, 60, 70, 80, 90 or 100 contiguous amino acid segment from any part of the whole protein), an exon, or a domain (e.g., a transmembrane domain), or it can refer to the entire protein, including any splicing variants. MS4A2 genes or coding sequences as set forth herein can be from any mammal having such gene or coding sequence. The MS4A2 gene or coding sequence may be from a human, mouse, canine, feline or equine.

The MS4A2 genomic locus can be found on human chromosome 11 and on mouse chromosome 19. The nucleotide sequences of the human and mouse MS4A2 genomic loci are presented in SEQ ID NOs: 6 and 12, respectively.

As used herein, an MS4A2 transcript is an RNA molecule transcribed from an MS4A2 gene. In some embodiments, MS4A2 transcripts targeted by oligomers as set forth herein are primary transcripts or pre-mRNA molecules. As used herein, primary mRNA or pre-mRNA is an mRNA transcript that has not yet undergone splicing. Accordingly, a mature mRNA molecule is an mRNA molecule that has undergone splicing.

With respect to the human and mouse MS4A2 genomic loci set forth in SEQ ID NOs: 6 and 12, respectively, intron and exon boundaries for these loci are presented in Table 2.

TABLE 2

| | Summary of Human and Mouse MS4A2 Intron/Exon Boundaries | |
| | Nucleotides in SEQ ID NO: 6 | Nucleotides in SEQ ID NO: 12 |
| --- | --- | --- |
| Exon 1 | 1-158 | 1-160 |
| Intron 1 | 159-1028 | 161-937 |

18

TABLE 2-continued

| | Summary of Human and Mouse MS4A2 Intron/Exon Boundaries | |
| | Nucleotides in SEQ ID NO: 6 | Nucleotides in SEQ ID NO: 12 |
| --- | --- | --- |
| Exon 2 | 1029-1158 | 938-1037 |
| Intron 2 | 1159-1672 | 1038-1542 |
| Exon 3 | 1673-1807 | 1543-1677 |
| Intron 3 | 1808-4126 | 1678-4046 |
| Exon 4 | 4127-4185 | 4047-4103 |
| Intron 4 | 4186-4736 | 4104-4710 |
| Exon 5 | 4737-4895 | 4711-4866 |
| Intron 5 | 4896-6300 | 4867-5205 |
| Exon 6 | 6301-5399 | 5206-5304 |
| Intron 6 | 5400-6894 | 5305-6148 |
| Exon 7 | 6895-9804 | 6149-8200 |

Exemplary antisense oligomers that can target human or mouse MS4A2 pre-mRNAs are disclosed in U.S. Patent Application Publication No. 2019/0062756, which is incorporated by reference in its entirety.

As used herein, the term antisense oligomer refers to a polymeric molecule comprising nucleobases, which is capable of hybridizing to a sequence in a nucleic acid molecule, such as an mRNA molecule. The term nucleobase, as used herein, refers to the heterocyclic base portion of a nucleoside. In general, a nucleobase is any group that contains one or more atoms, or groups of atoms, capable of hydrogen bonding to a base of another nucleoside. In addition to "unmodified" or "natural" nucleobases such as the purine nucleobases adenine (A) and guanine (G), and the pyrimidine nucleobases thymine (T), cytosine (C) and uracil (U), modified nucleobases or nucleobase mimetics known to those skilled in the art are also amenable to this disclosure. The term "modified nucleobase" refers to a nucleobase that is similar in structure to the parent nucleobase, such as for example, a 7-deaza purine, a 5-methyl cytosine, a G-clamp, or a tricyclic phenoxazine nucleobase mimetic. Methods for preparation of these modified nucleobases are known to those skilled in the art.

As is known in the art, a nucleoside is a base-sugar combination. The base portion of the nucleoside is normally a heterocyclic base (e.g., a nucleobase or simply a "base"). The two most common classes of such heterocyclic bases are purines and the pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. Within oligonucleotides, the phosphate groups are commonly referred to as forming the internucleoside backbone of the oligonucleotide. The normal linkage or backbone of RNA and DNA is a 3' to 5' phosphodiester linkage.

It is understood in the art that RNA molecules often have a short half-life, making their use as therapeutic agents problematic. Thus, it is often preferable to include chemical modifications in oligonucleotides to alter their activity. Chemical modifications can alter oligomer activity by, for example, increasing affinity of an antisense oligomer for its target RNA, increasing nuclease resistance (e.g., resistance to ribonucleases such as RNaseH), and/or altering the pharmacokinetics (e.g., half-life) of the oligomer. For example, it is possible to replace sugars, nucleobases and/or internucleoside linkages with a group that maintains the ability of the oligomer to hybridize to its target sequence, but which imparts a desirable characteristic to the oligomer (e.g., resistance to degradation, increased half-life, etc.). Such groups can be referred to as analogs (e.g., sugar analog, nucleobase analog, etc.). Generally, an analog is used in place of the sugar or sugar-internucleoside linkage combination, and the nucleobase is maintained for hybridization to a selected target. Representative examples of a sugar mimetic include, but are not limited to, cyclohexenyl or morpholino. Representative examples of a mimetic for a sugar-internucleoside linkage combination include, but are not limited to, peptide nucleic acids (PNA) and morpholino groups linked by uncharged, achiral linkages. In some instances, an analog is used in place of the nucleobase. Representative nucleobase mimetics are well known in the art and include, but are not limited to, tricyclic phenoxazine analogs and universal bases (Berger et al., 2000, incorporated herein by reference). Examples of such sugar, nucleoside and nucleobase mimetics are disclosed in U.S. Pat. Nos. 8,765,703 and 8,946,183, which are incorporated herein by reference). Methods of synthesis of sugar, nucleoside and nucleobase mimetics, and the use of such mimetics to produce oligonucleotides are well known to those skilled in the art.

The term oligomer includes oligonucleotides, oligo-nucleosides, oligonucleotide analogs, oligonucleotide mimetics and chimeric combinations thereof. Such molecules are generally known to those skilled in the art. Oligomers as set forth herein include, but are not limited to, primers, probes, antisense compounds, antisense oligonucle-otides, external guide sequence (EGS) oligonucleotides, alternate splicers, and siRNAs. As such, these compounds can be introduced in the form of single-stranded, double-stranded, circular, branched or hairpins and can contain structural elements such as internal or terminal bulges or loops.

Oligomers as set forth herein can be any length suitable for administering to a cell or individual in order to modulate splicing of an mRNA molecule. For example, antisense oligomers as set forth herein can comprise from about 10 to about 50 nucleobases (i.e. from about 10 to about 50 linked nucleosides). One having ordinary skill in the art will appreciate that this embodies antisense oligomers of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases. In some embodiments, antisense oligomers as set forth herein can comprise, or consist of, 10 to 30 nucleobases, or 10 to 25 nucleobases. Methods of determining the appropriate length for antisense oligomers as set forth herein are known to those skilled in the art.

As used herein, the terms "targeted to," "targeting," and the like, refer to a process of designing an antisense oli-gomer so that it specifically hybridizes with a desired nucleic acid molecule, such as a desired mRNA molecule. The terms "hybridizes," "hybridization," "hybridize to," and the like, are terms of art, and refer to the pairing of nucleobases in complementary strands of oligonucleotides (e.g., an antisense oligomer and a target sequence in a mRNA molecule). While not limited to a particular mecha-nism, the most common mechanism of pairing involves hydrogen bonding, which may be Watson-Crick, Hoogsteen, or reversed Hoogsteen hydrogen bonding, between comple-mentary nucleoside or nucleotide bases (nucleobases). For example, the natural base adenine is complementary to the natural nucleobases thymidine and uracil, which pair through the formation of hydrogen bonds. Similarly, the natural base guanine is complementary to the natural bases cytosine and 5-methyl cytosine.

In the context as set forth herein, the phrase "specifically hybridizes" refers to the capacity of an antisense oligomer as set forth herein to preferentially bind an mRNA (e.g., a pre-mRNA) encoding an MS4A6A or FcεRIβ protein rather than binding an mRNA encoding a protein unrelated in structure to an MS4A6A or FcεRIβ protein. Further, an antisense oligomer that preferentially binds a target sequence is one that hybridizes with an mRNA encoding an MS4A6A or FcεRIβ protein (an MS4A6A or FcεRIβ pre-mRNA), but which does not exhibit significant hybridization with mRNA molecules encoding proteins unrelated in struc-ture to an MS4A6A or FcεRIβ protein. In the context used herein, significant hybridization is, for example, binding of an oligomer as set forth herein to an mRNA encoding a protein unrelated in structure to an MS4A6A or FcεRIβ protein, with an affinity or avidity sufficiently high enough to interfere with the ability of the antisense oligomer to achieve the desired effect. Examples of such desired effects include, but are not limited to, modulation of splicing of an MS4A6A or MS4A2 pre-mRNA, reduction in the level of surface expression of FcεRI protein, and a reduction or inhibition in allergic symptoms in an individual. Thus, it will be understood by those skilled in the art that an antisense oligomer is considered specific for a target sequence (is specifically hybridizable, specifically hybridizes, etc.) when there is a sufficient degree of complementarity between the linear sequence of nucleobases in the antisense oligomer and a linear sequence of nucleobases in the target sequence, to avoid significant binding of the antisense oligomer to non-target nucleic acid sequences under conditions in which specific binding is desired (i.e., under physiological condi-tions in the case of in vivo assays or therapeutic treatment, and under conditions in which assays are performed in the case of in vitro assays).

A used herein, the terms "complement," "complemen-tary," "complementarity," and the like, refer to the capacity for precise pairing between nucleobases in an oligomer and nucleobases in a target sequence. Thus, if a nucleobase (e.g., adenine) at a certain position of an oligomer is capable of hydrogen bonding with a nucleobase (e.g., uracil) at a certain position in a target sequence in a target nucleic acid, then the position of hydrogen bonding between the oligomer and the target nucleic acid is considered to be a comple-mentary position. Usually, the terms complement, comple-mentary, complementarity, and the like, are viewed in the context of a comparison between a defined number of contiguous nucleotides in a first nucleic acid molecule (e.g., an oligomer) and a similar number of contiguous nucleotides in a second nucleic acid molecule (e.g., a mRNA molecule), rather than in a single base to base manner. For example, if an antisense oligomer is 25 nucleotides in length, its comple-mentarity with a target sequence is usually determined by comparing the sequence of the entire oligomer, or a defined portion thereof, with a number of contiguous nucleotides in a mRNA molecule. An oligomer and a target sequence are complementary to each other when a sufficient number of corresponding positions in each molecule are occupied by nucleobases which can hydrogen bond with each other. Positions are corresponding when the bases occupying the positions are spatially arranged such that, if complementary, the bases form hydrogen bonds. As an example, when comparing the sequence of an oligomer to a similarly sized sequence in a target sequence, the first nucleotide in the oligomer is compared with a chosen nucleotide at the start of the target sequence. The second nucleotide in the oligomer (3' to the first nucleotide) is then compared with the nucleotide directly 3' to the chosen start nucleotide. This process is then continued with each nucleotide along the length of the oligomer. Thus, the terms "specifically hybridizable" and "complementary" are terms which are used to indicate a sufficient degree of precise pairing or complementarity over a sufficient number of contiguous nucleobases such that stable and specific binding occurs between the antisense compound and a target nucleic acid.

Hybridization conditions under which a first nucleic acid molecule will specifically hybridize with a second nucleic acid molecule are commonly referred to in the art as stringent hybridization conditions. It is understood by those skilled in the art that stringent hybridization conditions are sequence-dependent and can be different in different circumstances. Thus, stringent conditions under which an oligomer as set forth herein specifically hybridizes to a target sequence are determined by the complementarity of the oligomer sequence and the target sequence and the nature of the assays in which they are being investigated. Persons skilled in the relevant art are capable of designing complementary sequences that specifically hybridize to a particular target sequence for a given assay or a given use.

The process of designing an antisense oligomer that is targeted to a nucleic acid molecule usually begins with identification of a target nucleic acid, the expression of which is to be modulated, and determining the sequence of the target nucleic acid molecule. As used herein, the terms "target nucleic acid," "nucleic acid encoding an MS4A6A or FcεRIβ protein," and the like, encompass, for example, DNA encoding an MS4A6A or FcεRIβ protein, RNA (including pre-mRNA and mRNA) transcribed from such DNA, and cDNA derived from such RNA. For example, the target nucleic acid can be a cellular gene (or pre-mRNA or mRNA transcribed therefrom), the expression of which is associated with a particular disorder or disease state. Thus, in some embodiments a useful target nucleic acid encodes an MS4A6A protein or an FcεRIβ protein. In some embodiments, the target nucleic acid is an MS4A6A transcript or an MS4A2 transcript. In some embodiments, the target nucleic acid is an MS4A6A or an MS4A2 pre-mRNA.

Once a target nucleic acid has been identified, the targeting process includes determining at least one target region in which the antisense interaction will occur, thereby modulating splicing of the target nucleic acid. As used herein, a target region is defined as a portion of the target nucleic acid having at least one identifiable structure, function, or characteristic. Exemplary target regions are those comprising sequences involved in splicing of pre-mRNA molecules. Examples of such identifiable structures, functions, or characteristics include, but are not limited to, at least a portion of an intron or exon, an intron/exon junction, a splice donor site, a splice acceptor site, a splice branch point or a splice enhancer site. Thus, in some embodiments, the target region comprises at least part of an intron or exon, a splice donor site, a splice acceptor site, a splice branch point, and/or a splice enhancer site. In some embodiments, the target region comprises at an intron or exon, a splice donor site, a splice acceptor site, a splice branch point, and/or a splice enhancer site.

Following identification of a target region, a target sequence within the target region can then be identified. As used herein, a target sequence is a nucleic acid sequence in a target region, to which an antisense oligomer as set forth herein specifically hybridizes. Exemplary target sequences are those involved in splicing of pre-mRNA. Once a target sequence has been identified, the antisense oligomer is designed to include a nucleobase sequence sufficiently complementary to the target sequence so that the antisense oligomer specifically hybridizes to the target nucleic acid. More specifically, the nucleotide sequence of the antisense oligomer is designed so that it contains a region of contiguous nucleotides sufficiently complementary to the target sequence so that the antisense oligomer specifically hybridizes to the target nucleic acid. Such a region of contiguous, complementary nucleotides in the oligomer can be referred to as an "antisense sequence" or a "targeting sequence."

It is well known in the art that the greater the degree of complementarity between two nucleic acid sequences, the stronger and more specific is the hybridization interaction. It is also well understood that the strongest and most specific hybridization occurs between two nucleic acid molecules that are fully complementary. As used herein, the term fully complementary refers to a situation when each nucleobase in a nucleic acid sequence is capable of hydrogen binding with the nucleobase in the corresponding position in a second nucleic acid molecule. In some embodiments, the targeting sequence is fully complementary to the target sequence. In some embodiments, the targeting sequence comprises an at least 6 contiguous nucleobase region that is fully complementary to an at least 6 contiguous nucleobase region in the target sequence. In some embodiments, the targeting sequence comprises an at least 8 contiguous nucleobase sequence that is fully complementary to an at least 8 contiguous nucleobase sequence in the target sequence. In some embodiments, the targeting sequence comprises an at least 10 contiguous nucleobase sequence that is fully complementary to an at least 10 contiguous nucleobase sequence in the target sequence. In some embodiments, the targeting sequence comprises an at least 12 contiguous nucleobase sequence that is fully complementary to an at least 12 contiguous nucleobase sequence in the target sequence. In some embodiments, the targeting sequence comprises an at least 14 contiguous nucleobase sequence that is fully complementary to an at least 14 contiguous nucleobase sequence in the target sequence. In some embodiments, the targeting sequence comprises an at least 16 contiguous nucleobase sequence that is fully complementary to an at least 16 contiguous nucleobase sequence in the target sequence. In some embodiments, the targeting sequence comprises an at least 18 contiguous nucleobase sequence that is fully complementary to an at least 18 contiguous nucleobase sequence in the target sequence. In some embodiments, the targeting sequence comprises an at least 20 contiguous nucleobase sequence that is fully complementary to an at least 20 contiguous nucleobase sequence in the target sequence.

It will be understood by those skilled in the art that the targeting sequence may make up the entirety of an antisense oligomer as set forth herein, or it may make up just a portion of an antisense oligomer as set forth herein. For example, in an oligomer consisting of 30 nucleotides, all 30 nucleotides can be complementary to a 30 contiguous nucleotide target sequence. Alternatively, for example, only 20 contiguous nucleotides in the oligomer may be complementary to a 20-contiguous nucleotide target sequence, with the remaining 10 nucleotides in the oligomer being mismatched to nucleotides outside of the target sequence. In some embodiments, oligomers as set forth herein have a targeting sequence of at least 10 nucleobases, at least 11 nucleobases, at least 12 nucleobases, at least 13 nucleobases, at least 14 nucleobases, at least 15 nucleobases, at least 16 nucleobases, at least 17 nucleobases, at least 18 nucleobases, at least 19 nucleobases, at least 20 nucleobases, at least 21 nucleobases, at least 22 nucleobases, at least 23 nucleobases, at least 24 nucleobases, at least 25 nucleobases, at least 26 nucleobases, at least 27 nucleobases, at least 28 nucleobases, at least 29 nucleobases, or at least 30 nucleobases, at least 35 nucleobases, at least 40 nucleobases, at least 45 nucleobases, or at least 50 nucleobases in length or longer.

It will be understood by those skilled in the art that the inclusion of mismatches between a targeting sequence and a target sequence is possible without eliminating the activity of the oligomer (e.g., modulation of splicing). Moreover, such mismatches can occur anywhere within the antisense interaction between the targeting sequence and the target sequence, so long as the antisense oligomer is capable of specifically hybridizing to the targeted nucleic acid molecule. Thus, antisense oligomers as set forth herein may comprise up to about 20% nucleotides that are mismatched, thereby disrupting base pairing of the antisense oligomer to a target sequence, as long as the antisense oligomer specifically hybridizes to the target sequence. In some embodiments, antisense oligomers comprise no more than 20%, no more than about 15%, no more than about 10%, no more than about 5% or not more than about 3% of mismatches, or less. In some embodiments, there are no mismatches between nucleotides in the antisense oligomer involved in pairing and a complementary target sequence. In some embodiments, mismatches do not occur at contiguous positions. For example, in an antisense oligomer containing 3 mismatch positions, in some embodiments the mismatched positions are separated by runs (e.g., 3, 4, 5, etc.) of contiguous nucleotides that are complementary with nucleotides in the target sequence The use of percent identity is a common way of defining the number of mismatches between two nucleic acid sequences. For example, two sequences having the same nucleobase pairing capacity would be considered 100% identical. Moreover, it should be understood that both uracil and thymidine will bind with adenine. Consequently, two molecules that are otherwise identical in sequence would be considered identical, even if one had uracil at position x and the other had a thymidine at corresponding position x. Percent identity may be calculated over the entire length of the oligomeric compound, or over just a portion of an oligomer. For example, the percent identity of a targeting sequence to a target sequence can be calculated to determine the capacity of an oligomer comprising the targeting sequence to bind to a nucleic acid molecule comprising the target sequence. In some embodiments, the targeting sequence is at least 80% identical, at least 85% identical, at least 90% identical, at least 95% identical, at least 97% identical, at least 98% identical or at least 99% identical over its entire length to a target sequence in a target nucleic acid molecule. In some embodiments, the targeting sequence is identical over its entire length to a target sequence in a target nucleic acid molecule.

It is understood by those skilled in the art that an antisense oligomer need not be identical to the oligomer sequences disclosed herein to function similarly to the antisense oligomers described herein. Shortened versions of antisense oligomers taught herein, or non-identical versions of the antisense oligomers taught herein, fall within the scope as set forth herein. Non-identical versions are those wherein each base does not have 100% identity with the antisense oligomers disclosed herein. Alternatively, a non-identical version can include at least one base replaced with a different base with different pairing activity (e.g., G can be replaced by C, A, or T). Percent identity is calculated according to the number of bases that have identical base pairing corresponding to the oligomer to which it is being compared. The non-identical bases may be adjacent to each other, dispersed throughout the oligomer, or both. For example, a 16-mer having the same sequence as nucleobases 2-17 of a 20-mer is 80% identical to the 20-mer. Alternatively, a 20-mer containing four nucleobases not identical to the 20-mer is also 80% identical to the 20-mer. A 14-mer having the same sequence as nucleobases 1-14 of an 18-mer is 78% identical to the 18-mer. Such calculations are well within the ability of those skilled in the art. Thus, antisense oligomers as set forth herein comprise oligonucleotide sequences at least 80% identical, at least 85% identical, at least 90% identical, at least 92% identical, at least 94% identical at least 96% identical or at least 98% identical to sequences disclosed herein, as long as the antisense oligomers are able to modulate splicing of a desired mRNA molecule.

Antisense oligomers as set forth herein are capable of modulating splicing of mRNA molecules. As used herein, "modulation" of splicing refers to the ability of an antisense oligomer to affect the processing of a pre-mRNA transcript such that the resulting spliced mRNA molecule contains a desired combination of exons as a result of exon skipping (or exon inclusion), a deletion in one or more exons, or additional sequence not normally found in the spliced mRNA (e.g., intronic sequences). For example, modulation of splicing can refer to affecting the splicing of an MS4A6A pre-mRNA and/or an MS4A2 pre-mRNA such that the spliced mRNA (mature mRNA) is missing at least a portion, or the entirety, of one exon. In some embodiments, the spliced mRNA lacks at least a portion of exon 3.

It has previously been discussed that a truncated isoform of the FcεRIβ protein (t-FcεRIβ) is present in cells, and that such truncation is due to a truncation in exon 3 of the mRNA encoding the FcεRIβ protein. It has been shown that the number or "level" of such truncated mRNA molecules is far less than the level of MS4A2 mRNA molecules including full-length exon 3. Thus, for the purposes of describing this disclosure, splicing of an MS4A2 pre-mRNA, due to the influence of an antisense oligomer, to produce a truncated mRNA encoding a truncated FcεRIβ protein, can be referred to as alternative splicing. Further, an MS4A2 mRNA transcript lacking at least a portion, or the entirety, of exon 3, due to the influence of an antisense oligomer, is a product of alternative splicing.

Thus, in the context as set forth herein, modulation of splicing can refer to inducing alternative splicing of an MS4A2 pre-mRNA molecule, thereby reducing the level of mRNA molecules containing the entirely of exon 3, and increasing the level of mRNA molecules lacking at least a portion of exon 3.

As such, some embodiments as set forth herein relate to an antisense oligomer comprising 10 to 50 linked nucleosides, wherein the oligomer is targeted to a region of an RNA molecule encoding an MS4A6 or FcεRIβ protein. In some embodiments, hybridization of the oligomer to the RNA molecule modulates splicing of the RNA molecule.

Some embodiments as set forth herein relate to antisense oligomers comprising a nucleic acid sequence sufficiently complementary to a target sequence in a target region of an MS4A6A mRNA molecule and/or an MS4A2 mRNA molecule, such that the antisense oligomer specifically hybridizes to the target sequence, thereby modulating splicing of an MS4A6A mRNA transcript and/or an MS4A2 mRNA transcript.

These antisense oligomers may consist of 10 to 50 linked nucleosides. These antisense oligomers may comprise 15 to 35 linked nucleotides. These antisense oligomers may consist of 15 to 35 linked nucleotides. These antisense oligomers may comprise or consist of 10 linked nucleosides, 11 linked nucleosides, 12 linked nucleosides, 13 linked nucleosides, 14 linked nucleosides, 15 linked nucleosides, 16 linked nucleosides, 17 linked nucleosides, 18 linked nucleosides, 19 linked nucleosides, 20 linked nucleosides, 21 linked nucleosides, 22 linked nucleosides, 23 linked nucleosides, 24 linked nucleosides, 25 linked nucleosides, 26 linked nucleosides, 27 linked nucleosides, 28 linked nucleosides, 29 linked nucleosides, 30 linked nucleosides, 31 linked nucleosides, 32 linked nucleosides, 33 linked nucleosides, 34 linked nucleosides, 34 linked nucleosides, 36 linked nucleosides, 37 linked nucleosides, 38 linked nucleosides, 39 linked nucleosides, 40 linked nucleosides, 41 linked nucleosides, 42 linked nucleosides, 43 linked nucleosides, 44 linked nucleosides, 45 linked nucleosides, 46 linked nucleosides, 47 linked nucleosides, 48 linked nucleosides, 49 linked nucleosides, or 50 linked nucleosides.

The mRNA molecule may encode an MS4A6A protein or an FcεRIβ protein from any mammal that produces an MS4A6A protein or an FcεRIβ protein. Examples of such mammals include, but are not limited to, a human, a mouse, a dog, a cat, and a horse. In some embodiments, the mRNA comprises a nucleotide sequence at least 80%, at least 85%, at least 90%, at least 95%, at least 97%, at least 99%, or 100% identical to any one of SEQ ID NOs: 1, 4, 7, and 10. In some embodiments, the mRNA encodes a protein comprising an amino acid sequence at least 80%, at least 85%, at least 90%, at least 95%, at least 97%, at least 99% identical to any one of SEQ ID NOs: 2, 5, 8, and 11. In some embodiments, the mRNA encodes a protein comprising SEQ ID NO: 2 or SEQ ID NO: 5.

The RNA molecule may be an MS4A6A mRNA transcript or an MS4A2 transcript. In some embodiments, the RNA molecule is an MS4A6A mRNA molecule. In some embodiments, the RNA molecule is an MS4A2 mRNA molecule. In some embodiments, the RNA molecule is an MS4A6A pre-mRNA. In some embodiments, the RNA molecule is an MS4A2 pre-mRNA.

The target region targeted by the antisense oligomer can be any region of the RNA molecule that is functionally involved in splicing of the RNA molecule. By "functionally involved in splicing" is meant the sequences in the target region are utilized by the cellular splicing apparatus (e.g., the spliceosome or components thereof) to effect splicing of the mRNA molecule. Examples of such regions include, but are not limited to, regions comprising intron sequences, regions comprising exon sequences, regions comprising intron/exon junctions, regions comprising splice donor site sequences, regions comprising splice acceptor site sequences, regions comprising splice enhancer site sequences, regions comprising branch point sequences, and regions comprising polypyrimidine tracts. Such sequences are known to those skilled in the art. Such sequences are also disclosed herein.

Thus in some embodiments, the target region comprises at least a portion of a sequence selected from the group consisting of an exon sequence, an intron sequence, a sequence comprising an exon/intron junction, a splice donor site sequence, a splice acceptor site sequence, a splice enhancer site sequence, a branch point sequence, and a polypyrimidine tract. In the context as set forth herein, "at least a portion" refers to at least 5 nucleosides, at least 6 nucleosides, at least 7 nucleosides, at least 8 nucleosides, at least 9 nucleosides, at least 10 nucleosides, at least 11 nucleotides, at least 12 nucleosides, at least 13 nucleotides, at least 14 nucleosides, at least 15 nucleosides, at least 16 nucleosides, at least 17 nucleosides, at least 18 nucleosides, at least 19 nucleosides, or at least 20 nucleosides in length. In some embodiments, the at least a portion comprises at least 10%, at least 25%, at least 50%, at least 75%, at least 90%, at least 90%, at least 95% or at least 97% of a known splice donor site sequence, splice acceptor site sequence, splice enhancer site sequence, branch point sequence or polypyrimidine sequence. The splice donor site sequence, splice acceptor site sequence, splice enhancer site sequence, branch point sequence, or polypyrimidine sequence may be from an MS4A6A pre-MRNA or an MS4A2 pre-MRNA.

In some embodiments, the target region comprises at least a portion of an MS4A6A sequence or an MS4A2 sequence as set forth herein, which may be any one of SEQ ID Nos: 1, 3, 4, 6, 7, 9, 10, and 12, including in some embodiments a portion of SEQ ID NO: 3, SEQ ID NO: 6, SEQ ID NO: 9, or SEQ ID NO: 12. In some embodiments, the at least a portion comprises at least 10%, at least 25%, at least 50%, at least 75%, at least 80%, at least 90% at least 95% or at least 97% of an MS4A6A sequence or an MS4A2 sequence as set forth herein. In some embodiments, the at least a portion comprises a polynucleotide sequence at least 80%, at least 90% at least 95% or at least 97% identical to a portion of an MS4A6A sequence or an MS4A2 sequence as set forth herein.

In some embodiments, the target region comprises a nucleotide sequence at least 80%, at least 90%, at least 95%, at least 97%, at least 99%, or 100% identical to at least a portion of a sequence selected from the group consisting of SEQ ID NOs: 3, 6, 9, and 12. In some embodiments, the target region comprises at least a portion of a sequence selected from the group consisting of SEQ ID NOs: 3, 6, 9, and 12.

In some embodiments, the antisense oligomer is targeted to a region or sequence involved in splicing of an MS4A6A pre-mRNA or an MS4A2 pre-mRNA. In some embodiments, the antisense oligomer is target to an MS4A6A or an MS4A2 intron sequence, an MS4A6A or an MS4A2 exon sequence, an MS4A6A or an MS4A2 splice donor site sequence, an MS4A6A or an MS4A2 splice acceptor site sequence, an MS4A6A or an MS4A2 splice enhancer site sequence, an MS4A6A or an MS4A2 branch point sequence, or an MS4A6A or an MS4A2 polypyrimidine tract. In some embodiments, the antisense oligomer is targeted to exon 4 of an MS4A6A pre-mRNA or exon 3 of an MS4A2 pre-mRNA. In some embodiments, the antisense oligomer is targeted to an MS4A6A exon 4 splice donor sequence or an MS4A2 exon 3 splice donor sequence, an MS4A6A exon 4 or MS4A2 exon 3 splice acceptor sequence, or an MS4A6A exon 4 or an MS4A2 exon 3 splice enhancer sequence.

In some embodiments, the antisense oligomer comprises a targeting sequence at least 80%, at least 90%, at least 95%, at least 97%, or at least 99% identical to a sequence fully complementary to at least a portion of a splice donor site sequence, a splice acceptor site sequence, a splice enhancer site sequence, a branch point sequence or a polypyrimidine sequence from an MS4A6A or an MS4A2 mRNA. In some embodiments, the antisense oligomer comprises a targeting sequence fully complementary to at least a portion of a splice donor site sequence, a splice acceptor site sequence, a splice enhancer site sequence, a branch point sequence, or a polypyrimidine sequence from an MS4A6A or an MS4A2 mRNA. In some embodiments, the antisense oligomer comprises a targeting sequence at least 80%, at least 90%, at least 95%, at least 97%, at least 99%, or 100% identical to a sequence fully complementary to at least a portion of a sequence selected from the group consisting of SEQ ID NOs: 3, 6, 9, and 12. In some embodiments, the antisense oligomer comprises a targeting sequence at least 80%, at least 90%, at least 95%, at least 97%, at least 99%, or 100% identical to a sequence fully complementary to at least a portion of a sequence selected from the group consisting of SEQ ID NOs: 3, 6, 9, and 12. The portion is in some embodiments least 10 nucleotides in length. The antisense oligomer may modulate splicing of an MS4A6A pre-mRNA molecule or an MS4A2 pre-mRNA molecule.

In some embodiments, the target region comprises at least a portion of a sequence selected from an MS4A6A or an MS4A2 splice donor site sequence, an MS4A6A or an MS4A2 splice acceptor site sequence, an MS4A6A or an MS4A2 splice enhancer site sequence, an MS4A6A or an MS4A2 branch point sequence, and an MS4A6A or an MS4A2 polypyrimidine sequence. In some embodiments, the at least a portion comprises at least 10%, at least 25%, at least 50%, at least 75%, at least 90% or at least 90% of an MS4A6A or an MS4A2 splice donor site sequence, an MS4A6A or an MS4A2 splice acceptor site sequence, an MS4A6A or an MS4A2 splice enhancer site sequence, an MS4A6A or an MS4A2 branch point sequence, or an MS4A6A or an MS4A2 polypyrimidine sequence. The MS4A6A or MS4A2 splice donor site sequence, the MS4A6A or MS4A2 splice acceptor site sequence, the MS4A6A or MS4A2 splice enhancer site sequence, the MS4A6A or MS4A2 branch point sequence, or MS4A6A or the MS4A2 polypyrimidine sequence, may be from exon 3 or exon 4 of an MS4A6A or an MS4A2 pre-mRNA. The portion may be at least 10 nucleotides in length. The antisense oligomer may modulate splicing of an MS4A6A or an MS4A2 pre-mRNA molecule.

In some embodiments, the complementary nucleic acid sequence comprised by the antisense oligomer (i.e., the "targeting sequence") is at least 80%, at least 90%, at least 95%, at least 97%, or at least 99% identical to a sequence fully complementary to at least a portion of a splice donor site sequence, splice acceptor site sequence, splice enhancer site sequence, branch point sequence or polypyrimidine sequence from an MS4A6A mRNA or an MS4A2 mRNA. In some embodiments, the complementary nucleic acid sequence comprised by the antisense oligomer comprises a sequence at least 80%, at least 90%, at least 95%, at least 97%, at least 99%, or 100% identical to a sequence fully complementary to a portion of a sequence selected from the group consisting of SEQ ID NOs: 3, 6, 9, or 12. The portion can in some embodiments be at least 10 nucleotides in length. The antisense oligomer can in some embodiments modulate splicing of an MS4A6A or an MS4A2 pre-mRNA molecule.

With reference now to genomic sequences, in some embodiments the target region comprises at least a portion of a sequence selected from an MS4A6A or an MS4A2 splice donor site sequence, an MS4A6A or an MS4A2 splice acceptor site sequence, an MS4A6A or an MS4A2 splice enhancer site sequence, an MS4A6A or an MS4A2 branch point sequence, and an MS4A6A or an MS4A2 polypyrimidine sequence, each of which is a subsequence of SEQ ID NO: 3 (e.g., an exemplary nucleotide sequence the human MS4A6A genomic locus), SEQ ID NO: 6 (e.g., an exemplary nucleotide sequence the human MS4A2 genomic locus), SEQ ID NO: 9 (e.g., an exemplary nucleotide sequence the murine MS4A6A genomic locus), or SEQ ID NO: 12 (e.g., an exemplary nucleotide sequence the murine MS4A2 genomic locus). In some embodiments, the target region comprises nucleotides on each side of an intron/exon boundary, which in some embodiments comprises at least 5, 6, 7, 8, 9, 10, 11, 12, 13, 14, 15, 16, 17, 18, 19, 20, or more nucleotides 5' to the intron/exon boundary, at least 5, 6, 7, 8, 9, 10, 11, 12, 13, 14, 15, 16, 17, 18, 19, 20, or more nucleotides 3' to the intron/exon boundary, or at least 5, 6, 7, 8, 9, 10, 11, 12, 13, 14, 15, 16, 17, 18, 19, 20, or more nucleotides 5' to and 3' to the intron/exon boundary, in any combination. The intron/exon boundaries for the human and murine MS4A6A and MS4A2 genetic loci are set forth in Tables 1 and 2, respectively.

Some embodiments of the presently disclosed subject matter as set forth herein relate to an expression vector that expresses an antisense oligomer as set forth herein. As used herein, an "expression vector" is a nucleic acid molecule comprising a polynucleotide sequence functionally linked to a promoter, such that transcription of the polynucleotide sequence by a polymerase results in production of an antisense oligomer as set forth herein. Exemplary expression vectors include polynucleotide molecules, in some embodiments DNA molecules, that are derived, for example, from a plasmid, bacteriophage, yeast or virus (e.g., adenovirus, adeno-associated virus, lentivirus, retrovirus, etc.), into which a polynucleotide can be inserted or cloned. Suitable expression vectors are known to those skilled in the art.

Some embodiments of the presently disclosed subject matter as set forth herein relate to a pharmaceutical composition comprising an antisense oligomer or expression vector as set forth herein. Such compositions are suitable for the therapeutic delivery of antisense oligomers, or expression vectors, described herein. Hence, this disclosure provides pharmaceutical compositions that comprise a therapeutically-effective amount of one or more of the antisense oligomers or expression vectors described herein, formulated together with one or more pharmaceutically-acceptable carriers (additives) and/or diluents. While it is possible in some embodiments for an antisense oligomers and/or expression vectors as set forth herein to be administered alone, in some embodiments the compounds of the presently disclosed subject matter are administered as a pharmaceutical composition.

Pharmaceutical compositions as set forth herein may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) inhaled into the lungs, for example, by nebulizer or aerosol inhaler; or (9) nasally. Examples of suitable carriers, additives and diluents are described in U.S. Patent Application Publication No. 2015/0361428, which is incorporated herein by reference in its entirety.

As has been described above, antisense oligomers as set forth herein are capable of reducing cell-surface expression of FcRI, the product of the MS4A2 gene. Such reduction is achieved by modulating splicing of an mRNA molecule encoding an MS4A6A and/or a FcεRIβ protein. More specifically, antisense oligomers as set forth herein decrease the production of MS4A6A and/or FcεRIβ-encoding mRNA molecules comprising exon 4 or exon 3, respectively, and increase the production of MS4A6A and/or FcεRIβ-encoding mRNA molecules lacking exon 4 or exon 3, respectively. Because these latter MS4A6A and/or FcεRIβ-encoding mRNA molecules lack exon 4 or exon 3, respectively, the encoded MS4A6A and/or FcεRIβ proteins lack the first transmembrane domain, which is required for trafficking of FcεRI complex to the cell membrane.

Thus, some embodiments of the presently disclosed subject matter as set forth herein relate to methods for modulating splicing of an MS4A6A and/or an FcεRIβ mRNA in a cell, the method comprising contacting the cell with one or more antisense oligomers as set forth herein. The cell may be any cell expressing an MS4A6A and/or an FcεRIβ mRNA molecule. Accordingly, the cell can be a cell in culture, or a cell in the body of an individual. In some embodiments, the cell is an epidermal Langerhans cell, an eosinophil, a mast cell, or a basophil. In a specific embodiment, the cell is a mast cell.

The mRNA may comprise a nucleotide sequence at least 80%, at least 85%, at least 90%, at least 95%, at least 97%, at least 99%, or 100% identical to one of SEQ ID NOs: 1 and 7 (MS4A6A) or SEQ ID NOs: 4 and 10 (MS4A2). In some embodiments, the mRNA encodes a protein comprising an amino acid sequence at least 80%, at least 85%, at least 90%, at least 95%, at least 97%, or at least 99% identical to one of SEQ ID NOs: 2 and 8 (MS4A6A) or SEQ ID NOs: 5 and 11 (MS4A2). In some embodiments, the mRNA encodes a protein comprising SEQ ID NO: 2, SEQ ID NO: 5, SEQ ID NO: 8, or SEQ ID NO: 11.

In some embodiments, the antisense oligomer hybridizes to a target region that is involved in splicing of an MS4A6A and/or MS4A2 pre-mRNA. In some embodiments, the antisense oligomer hybridizes to a target region in the mRNA comprising at least a portion of a sequence selected from the group consisting of an MS4A6A and/or an MS4A2 splice donor site sequence, an MS4A6A and/or an MS4A2 splice acceptor site sequence, an MS4A6A and/or an MS4A2 splice enhancer site sequence, an MS4A6A and/or an MS4A2 branch point sequence, and an MS4A6A and/or an MS4A2 polypyrimidine sequence. The MS4A6A and/or MS4A2 splice donor site sequence, the MS4A6A and/or MS4A2 splice acceptor site sequence, the MS4A6A and/or MS4A2 splice enhancer site sequence, the MS4A6A and/or MS4A2 branch point sequence, or the MS4A6A and/or MS4A2 polypyrimidine sequence may be from exon 4 of an MS4A6A and/or exon 3 of an MS4A2 pre-mRNA.

Modulation of splicing of an MS4A6A and/or FcεRIβ pre-mRNA by antisense oligomers as set forth herein can result in production of a truncated mRNA (t-MS4A6A and/or t-FcεRIβ mRNA), which produces a truncated form of the MS4A6A and/or FcεRIβ protein. t-MS4A6A and t-FcεRIβ mRNAs differ from full-length MS4A6A and FcεRIβ mRNAs (FL-MS4A6A and FL-FcεRIβ mRNAs, respectively) in that they are truncated in exon 4 or exon 3, respectively, thereby producing MS4A6A and FcεRIβ proteins lacking the first and second membrane-spanning regions. Normally, the amount of FL-MS4A6A and FL-FcεRIβ mRNAs in mast cells is greater than the amount of t-MS4A6A and t-FcεRIβ mRNAs. Thus, some embodiments of the presently disclosed subject matter as set forth herein relate to methods for altering the ratio of FL-MS4A6A and/or FL-FcεRIβ mRNAs to t-MS4A6A and/or t-FcεRIβ mRNAs in a mast cell, the method comprising contacting the mast cell with one or more antisense oligomers as set forth herein. Contact of a mast cell with one or more antisense oligomers as set forth herein may cause a decrease in the amount of FL-MS4A6A and/or FL-FcεRIβ mRNAs and an increase in the amount of t-MS4A6A and/or t-FcεRIβ mRNAs. Contact of a mast cell with an antisense oligomer as set forth herein may result in a decreased FL-MS4A6A mRNA/t-MS4A6A mRNA and/or FL-FcεRIβ mRNA/t-FcεRIβ mRNA ratio. In some embodiments, the amount of FL-MS4A6A and/or FL-FcεRIβ mRNAs produced by the cell is decreased by at least 50%, at least 60%, at least 70%, at least 80%, at least 90%, at least 95%, least 97%, or at least 99%.

The presently disclosed subject matter also relates in some embodiments to methods for reducing cell surface expression of FcεRI protein in a cell, the method comprising contacting the cell with one or more antisense oligomers as set forth herein. In embodiments as set forth herein, the cell can be any cell expressing an FcεRI protein on its surface. Accordingly, the cell can be a cell in culture (e.g., tissue culture) or a cell in the body of an individual. In some embodiments, the cell is an epidermal Langerhans cell, an eosinophil, a mast cell or a basophil. In a specific embodiment, the cell is a mast cell.

In some embodiments, the amount of FcεRI expressed on the surface of the cell is decreased by at least 50%, at least 60%, at least 70%, at least 80%, at least 90%, at least 95%, at least 97%, or at least 99%.

Mast cells are tissue-bound cells of the innate immune system which are well known for immunoglobulin (Ig)E-triggered degranulation in allergic reactions. Consequently, mast cells express large quantities of FcεRI receptor on their surface. As the binding of IgE to FcεRI is essentially irreversible, mast cells are largely covered with IgE. The main function of mast cells is considered to be degranulation, with immunoglobulin (Ig)E as the main trigger. Once an IgE molecule encounters a specific antigen or allergen, IgE:FcεRI-crosslinking and calcium influx leads to degranulation of the mast cells. As a result, histamine is released and causes the well-known symptoms such as bronchoconstriction or pruritus. Thus, one embodiment as set forth herein is a method for modulating FcεRI-dependent mast-cell degranulation, the method comprising contacting a mast cell with an antisense oligomer as set forth herein. In accordance with this disclosure, the cell can be a cell in culture (e.g., tissue culture) or a cell in the body of an individual.

Upon activation, mast cells rapidly release pre-formed mediators from cytoplasmic granules, such as vasoactive amines (e.g., histamine and serotonin), proteoglycans (e.g., heparin), proteases (e.g., tryptases and chymases), and some pre-stored cytokines (e.g., TNFα). They also release a plethora of mediators, including growth factors, cytokines, and chemokines, such as IL-1, IL-6, IL-8, IL-10, TNFα, VEGF, TGFβ, CCL2-4, as well as pro-inflammatory lipid mediators, such as prostaglandins and leukotrienes. Thus, one embodiment as set forth herein is a method for modulating the release of one or more mediators from a mast cell, the method comprising contacting a mast cell with an antisense oligomer as set forth herein, where the one or more mediators is selected from the group consisting of a mast cell-produced vasoactive amine, a mast cell-produced proteoglycan, a mast cell-produced protease, a cytokine, a growth factor, a chemokine, and a pro-inflammatory lipid mediator. The one or more mediator may be any one of histamine, serotonin, heparin, tryptase, chymase, TNFα, IL-1, IL-6, IL-8, IL-10, TNFα, VEGF, TGFβ, CCL2-4, a prostaglandin, and a leukotriene. In specific embodiments, the mast cell can be a cell in culture, or a cell in the body of an individual.

As players in innate immunity, mast cells have the capacity to initiate and amplify immune responses (see Bulfone-Paus & Rahri, 2015). Several lines of evidence have demonstrated that mast cells participate in the sensitization phase of acquired immune responses via the secretion of mediators, which sustain dendritic cell (DC) maturation, function, and recruitment to the tissue or their migration to local draining lymph nodes. However, mast cells also exert important effector functions, since mast cells and T cells of different origin and subsets establish tight cell-cell interactions and modulate their respective effector functions in a bidirectional manner; this has been shown in a variety of models. Thus, one embodiment as set forth herein is a method for reducing an immune response in an individual, the method comprising administering an antisense oligomer as set forth herein to the individual. Such immune response can, but need not be, IgE-mediated immune responses.

The antisense oligomers as set forth herein may be administered to any individual expressing an FcεRIβ protein. As used herein, the terms individual, subject, patient, and the like, are meant to encompass any mammal that expresses an FcεRIβ protein, with an exemplary mammal being a human. The terms individual, subject, and patient by themselves do not denote a particular age, sex, race, and the like. Thus, individuals of any age, whether male or female, are intended to be covered by this disclosure. Likewise, the methods as set forth herein can be applied to any race of human, including, for example, Caucasian (white), African-American (black), Native American, Native Hawaiian, Hispanic, Latino, Asian, and European. In some embodiments as set forth herein, such characteristics may be significant. In such cases, the significant characteristic(s) (e.g., age, sex, race, etc.) will be indicated. Additionally, the term "individual" encompasses both human and non-human animals. Suitable non-human animals to which antisense oligomers as set forth herein may be administered include, but are not limited to companion animals (i.e. pets), food animals, work animals, or zoo animals. Exemplary animals include, but are not limited to, cats, dogs, horses, ferrets and other Mustelids, cattle, sheep, swine, and rodents.

Antisense oligomers as set forth herein can be administered to an individual by any suitable route of administration. Examples of such routes include, but are not limited to, oral and parenteral routes, (e.g., intravenous (IV), subcutaneous, intraperitoneal (IP), and intramuscular), inhalation (e.g., nebulization and inhalation) and transdermal delivery (e.g., topical). Any methods effective to deliver an antisense oligomer as set forth herein into the bloodstream of an individual are also contemplated in these methods. For example, transdermal delivery of antisense oligomers may be accomplished by use of a pharmaceutically acceptable carrier adapted for topical administration. Antisense oligomers can be administered in the absence of other molecules, such as proteins or lipids, or they be administered in a complex with other molecules, such as proteins or lipids. For example, the use of cationic lipids to encapsulate antisense oligomers is disclosed in U.S. Pat. Nos. 8,569,256, and 6,806,084, which are incorporated herein by reference in their entirety. Similarly, the use of peptide-linked morpholino antisense oligonucleotides is disclosed in U.S. Patent Application Publication No. 2015/0238627, which is incorporated herein by reference. IgE and IgE-mediated immune responses are known to be involved in numerous allergic conditions. Because antisense oligomers as set forth herein can reduce FcεRI-mediated responses, such antisense oligomers can be used to treat allergic conditions. Thus, one embodiment as set forth herein is a method for treating an allergic condition in an individual, by administering to an individual in need of such treatment an antisense oligomer as set forth herein. Allergic conditions being treated can be any condition mediated by a pathway comprising FcεRI. Such conditions include, but are not limited to, asthma, food allergies allergic conjunctivitis, and atopic dermatitis. Methods and compositions for designing and administering antisense oligomers to cells and to subjects are described in, for example, U.S. Pat. Nos. 7,973,015; 8,236,557; 8,268,962; 8,304,398; 8,361,979; 8,802,645; 9,080,170; 9,238,042; 9,598,703; 9,738,891; 9,862,945; 10,030,894; 10,188,633; and 10,590,420, the entire disclosure of each of which is incorporated by reference in its entirety.

Dose ranges of antisense oligonucleotide according to the presently disclosed subject matter are in some embodiments designed on the basis of rising dose studies in clinical trials (in vivo use) for which rigorous protocol requirements exist. A molecule or an oligonucleotide as defined herein can be used at a dose which ranges in some embodiments between 0.1 and 20 mg/kg and in some embodiments between 0.5 and 10 mg/kg.

In some embodiments, a concentration of an antisense oligonucleotide as defined herein, which ranges in some embodiments between 0.1 nM and 1 μM is used. In some embodiments, the concentration used is between 0.3 to 400 nM, and in some embodiments is between 1 to 200 nM. If several oligonucleotides are used, this concentration or dose can refer in some embodiments to the total concentration or dose of oligonucleotides and in some embodiments can refer to the concentration or dose of each oligonucleotide added.

The ranges of concentration or dose of oligonucleotide(s) as given above are exemplary concentrations or doses for in vitro or ex vivo uses. The skilled person will understand that depending on the oligonucleotide(s) used, the target cell to be treated, the gene target and its expression levels, the medium used and the transfection and incubation conditions, the concentration or dose of oligonucleotide(s) used can further vary and could need to be optimized further.

An oligonucleotide as defined herein for use according to the presently disclosed subject matter can be suitable for administration to a cell, tissue, and/or an organ in vivo of individuals affected by or at risk of developing undesirable allergic reactions, and can be administered in vivo, ex vivo or in vitro. Said oligonucleotide can be directly or indirectly administrated to a cell, tissue, and/or an organ in vivo of an individual, and can be administered directly or indirectly in vivo, ex vivo, or in vitro.

An oligonucleotide of the presently disclosed subject matter can be indirectly administrated using suitable techniques known in the art. An oligonucleotide can for example be provided to an individual or a cell, tissue, or organ of said individual in the form of an expression vector wherein the expression vector encodes one or more transcripts comprising said oligonucleotide or plurality of oligonucleotides. The expression vector can in some embodiments be introduced into a cell, tissue, organ, or individual via a gene delivery vehicle. In some embodiments, there is provided a viral-based expression vector comprising an expression cassette or a transcription cassette that drives expression or transcription of a molecule as identified herein. A preferred delivery vehicle is a viral vector such as an adeno-associated virus vector (AAV), or a retroviral vector such as a lentivirus vector (see e.g., De Angelis et al.; 2002; Goyenvalle et al.; 2004; Denti et al., 2006). Also, plasmids, artificial chromosomes, including but not limited to plasmids suitable for targeted homologous recombination and integration in the human genome of cells, can be suitably applied for delivery of an oligonucleotide as defined herein.

The oligonucleotide can be delivered as is. However, the oligonucleotide can also be encoded by the viral vector. Typically, this is in the form of an RNA transcript that comprises the sequence of the oligonucleotide in a part of the transcript.

Improvements in methods for providing an individual or a cell, tissue, and/or organ of said individual with an oligonucleotide and/or an equivalent thereof, are anticipated. Such future improvements can of course be incorporated into the presently disclosed subject matter to achieve the mentioned effect on restructuring of mRNA using the compositions and methods of the presently disclosed subject matter. An oligonucleotide and/or an equivalent thereof can be delivered as is to an individual, a cell, a tissue, and/or an organ of said individual. When administering an oligonucleotide and/or an equivalent thereof, in some embodiments oligonucleotide and/or an equivalent thereof is dissolved in a solution that is compatible with the delivery method. For intravenous, subcutaneous, intramuscular, intrathecal and/or intraventricular administration, in some embodiments the solution is a physiological salt solution. In some embodiments, the use of an excipient that aids in delivery of each of the constituents as defined herein to a cell and/or into a cell, tissue, and/or organ. Exemplary excipients including, but are not limited to those capable of forming complexes, nanoparticles, micelles, vesicles, and/or liposomes that deliver each constituent as defined herein, complexed, associated with, and/or trapped in a vesicle or liposome through a cell membrane. Many of these excipients are known in the art. Suitable excipients comprise polyethylenimine (PEI), or similar cationic polymers, including polypropyleneimine or polyethylenimine copolymers (PECs) and derivatives, synthetic amphiphils (SAINT-18), LIPOFECTIN™ brand lipofection enhancer, DOTAP, and/or viral capsid proteins that are capable of self assembly into particles that can deliver each constitutent as defined herein to a cell, tissue, and/or organ. Such excipients have been shown to efficiently deliver an oligonucleotide such as antisense nucleic acids to a wide variety of cultured cells. Their high transfection potential is combined with an excepted low to moderate toxicity in terms of overall cell survival. The ease of structural modification can be used to allow further modifications and the analysis of their further (in vivo) nucleic acid transfer characteristics and toxicity.

LIPOFECTIN™ brand lipofection enhancer represents an example of a liposomal transfection agent. It consists of two lipid components, a cationic lipid N-[1-(2,3 dioleoyloxy) propyl]-N,N,N-trimethylammonium chloride (DOTMA) (cp. DOTAP which is the methylsulfate salt) and a neutral lipid dioleoylphosphatidylethanolamine (DOPE). The neutral component mediates the intracellular release. Another group of delivery systems are polymeric nanoparticles.

Polycations such like diethylaminoethylaminoethyl (DEAE)-dextran, which are well known as DNA transfection reagent can be combined with butylcyanoacrylate (PBCA) and hexylcyanoacrylate (PHCA) to formulate cationic nanoparticles that can deliver each constituent as defined herein, preferably an oligonucleotide across cell membranes into cells.

In addition to these common nanoparticle materials, the cationic peptide protamine offers an alternative approach to formulate an oligonucleotide with colloids. This colloidal nanoparticle system can form so called proticles, which can be prepared by a simple self-assembly process to package and mediate intracellular release of an oligonucleotide. The skilled person may select and adapt any of the above or other commercially available alternative excipients and delivery systems to package and deliver an oligonucleotide for use in the compositions and methods of the presently disclosed subject matter, particularly for use in humans.

In addition, an oligonucleotide could be covalently or non-covalently linked to a targeting ligand specifically designed to facilitate the uptake into the cell, cytoplasm and/or its nucleus. Such ligand could comprise (i) a compound (including but not limited to peptide(-like) structures) recognizing cell, tissue or organ specific elements facilitating cellular uptake and/or (ii) a chemical compound able to facilitate the uptake in to cells and/or the intracellular release of an oligonucleotide from vesicles, e.g. endosomes or lysosomes.

Therefore, in some embodiments, an oligonucleotide is formulated in a composition or a medicament or a composition, which is provided with at least an excipient and/or a targeting ligand for delivery and/or a delivery device thereof to a cell and/or enhancing its intracellular delivery. Accordingly, the presently disclosed subject matter also encompasses a pharmaceutically acceptable composition comprising an oligonucleotide and further comprising at least one excipient and/or a targeting ligand for delivery and/or a delivery device of said oligonucleotide to a cell and/or enhancing its intracellular delivery. It is to be understood that if a composition comprises an additional constituent such as an adjunct compound as later defined herein, each constituent of the composition may not be formulated in one single combination or composition or preparation. Depending on their identity, the skilled person will know which type of formulation is the most appropriate for each constituent as defined herein.

In some embodiments, a target cell is a mast cell. In an allergic person, whose tissue mast cells and other cell types already have antigen-specific IgE bound to FcεRI, re-exposure to the original or a cross-reactive bivalent or multivalent antigen results in the cross-linking of adjacent FcεRI-bound IgE and the consequent aggregation of surface FcεRI. When the FcεRI aggregation is of sufficient strength and duration, it triggers mast cells and basophils to initiate complex signaling events that ultimately result in the secretion of a diverse group of biologically active products. In aggregate, mediators released shortly after antigen- and IgE-induced mast cell degranulation induce a response termed an immediate hypersensitivity (or early phase) reaction within minutes of their release. If localized to the airways, this response is characterized by increased vascular permeability, contraction of the airway smooth muscle and enhanced secretion of mucus, resulting in acutely reduced airflow and wheezing. If the response is systemic, it can result in anaphylaxis, a catastrophic immune response that can rapidly result in death if not properly treated (for a review, see Galli & Tsai, 2012). Thus, some embodiments of the presently disclosed subject matter as set forth herein relate to methods for preventing or treating an anaphylactic reaction in an individual, the method comprising administering to an individual in need of such treatment one or more antisense oligomers as set forth herein. The antisense oligomers as set forth herein may be administered in advance of an anaphylactic reaction or anticipated anaphylactic reaction in the individual. The antisense oligomers as set forth herein is in some embodiments administered at regular intervals to prevent or reduce the incidence and/or severity of any anaphylactic reaction in an individual at risk of having an anaphylactic reaction or developing anaphylactic shock. The individual being treated may or may not be at immediate risk for having an anaphylactic reaction. Some embodiments of the presently disclosed subject matter as set forth herein thus relate to methods for modulating an ana- phylactic reaction in an individual, the methods comprising administering to an individual in need of such treatment an antisense oligomer as set forth herein.

Mastocytosis is a rare mast cell activation disorder caused by an individual having too many mast cells and mast cell precursors. Because mast cells are involved in atopic responses, individuals suffering from mastocytosis are sus- ceptible to hives, itching and anaphylactic shock. Thus, one method as set forth herein is a method for treating an individual suffering from mastocytosis, the method compris- ing administering to an individual in need of such treatment an antisense oligomer as set forth herein. The individual may or may not already be exhibiting symptoms of mastocytosis, such as itching, hives and anaphylaxis. In some embodi- ments, an antisense oligomer is administered to an indi- vidual at risk for developing symptoms of mastocytosis.

Mast cells are produced in the bone marrow and are found throughout the connective tissue of the body. In some individuals, mast cells accumulate the skin, forming clusters that appear as a bump. Such clusters of mast cells are referred to as mastocytomas. A common symptom resulting from a mastocytoma is itching, although afflicted individuals can also experience urticarial, pigmentosa, flushing, nausea, vomiting, diarrhea and abdominal pain. One method as set forth herein is a method for treating an individual diagnosed with a mastocytoma or suspected of having a mastocytoma, by administering to the individual an antisense oligomer as set forth herein. In some embodiments, administration of an antisense oligomer eliminates one or more symptom(s) resulting from a mastocytoma.

This disclosure also provides kits for modulating splicing of an MS4A6A and/or an FcεRIβ mRNA, reducing cell surface expression of an FcεRI protein, modulating an anaphylactic reaction in an individual, and/or treating an individual for an allergic condition, the kit comprising at least one antisense oligomer as set forth herein. The kit may also comprise instructions for using the kit, and various reagents, such as buffers, necessary to practice the methods as set forth herein. These reagents or buffers may be useful for administering the antisense oligomers as set forth herein to a cell or an individual. The kit may also comprise any material necessary to practice the methods as set forth herein, such as syringes, tubes, swabs, and the like. In some embodiments, the presently disclosed subject matter pro- vides a composition or a preparation which is in the form of a kit of parts comprising an oligonucleotide and a further adjunct compound as later defined herein.

The presently disclosed subject matter also relates in some embodiments to methods for employing the antisense oligonucleotides to treat and/or prevent various diseases, disorders, and/or conditions in subjects in need thereof. Exemplary such methods include, but are not limited to methods for modulating splicing of mRNAs encoding MS4A6A proteins in cells or tissues, methods for reducing cell surface expression of FcεRI proteins in cells, methods for modulating FcεRI receptor complex-dependent degranu- lation in mast cells, methods for modulating FcεRI receptor complex-dependent mast-cell migration, methods for modu- lating cytokine release, methods for inhibiting anaphylaxis reactions in individuals, methods for treating allergic con- ditions in individuals, methods for reducing the incidence of allergic reactions in individuals, methods for treating individuals at risk of developing anaphylactic reactions, and methods for treating mast cell-related diseases in individu- als. These and other treatment and/or prevention methods will be apparent to one of ordinary skill in the art after consideration of the present disclosure.

EXAMPLES

The following EXAMPLES as set forth herein have been presented for purposes of illustration and description. These EXAMPLES are not intended to limit the disclosure to the form disclosed herein, as variations and modifications com- mensurate with the teachings of the description of the disclosure, and the skill or knowledge of the relevant art, are within the scope as set forth herein. It is intended that the appended claims be construed to include alternative embodi- ments to the extent permitted by the prior art.

Without further description, it is believed that one of ordinary skill in the art can, using the preceding description and the following illustrative EXAMPLES, make and utilize the compounds of the presently disclosed subject matter and practice the methods of the presently disclosed subject matter. The following EXAMPLES therefore particularly point out embodiments of the presently disclosed subject matter and are not to be construed as limiting in any way the remainder of the disclosure.

Example 1

FcεRIα SSOs Eliminate Mouse FcεRI to the Plasma Mem- brane

Expression of a truncated isoform of FcεRIβ in MCs that lacks exon 3 (Cruse et al., 2010; Cruse et al., 2013) was identified. Exon 3 of MS4A2 encodes the 1st and 2nd TM domains of FcεRIβ. The 1st TM domain of FcεRIβ is critical for trafficking the FcεRI complex to the plasma membrane (Singleton et al., 2009). It was predicted that alternative splicing of FcεRIβ results in loss of association with the εcomplex. This prediction was confirmed (Cruse et al., 2010; Cruse et al., 2013), and SSOs were devised to force alternative FcεRIβ splicing to eliminate FcεRI trafficking to the cell surface. FcεRIβ SSOs were efficient in mouse bone marrow-derived cultured MCs (BMMCs) with correspond- ing elimination of surface FcεRI expression (Cruse et al., 2016). SSO-treated BMMCs were thus unresponsive to antigen with no evidence of IgE-dependent degranulation, but degranulation in response to thapsigargin was unaffected (Cruse et al., 2016). Similar results were observed with $Ca^{2+}$ signaling using ratiometric Fura2 measurements and cyto- kine production followed the same pattern (Cruse et al., 2016). Taken together, these data demonstrated that exon 3 of FcεRIβ was critical for FcεRI function.

Example 2

FcεRIβ SSOs are Less Effective in huMCs

Figure 1B:
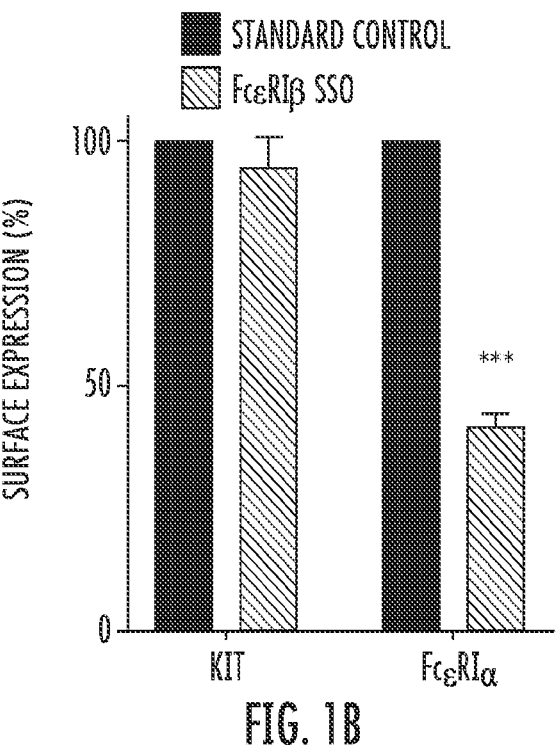
Figure 1C:
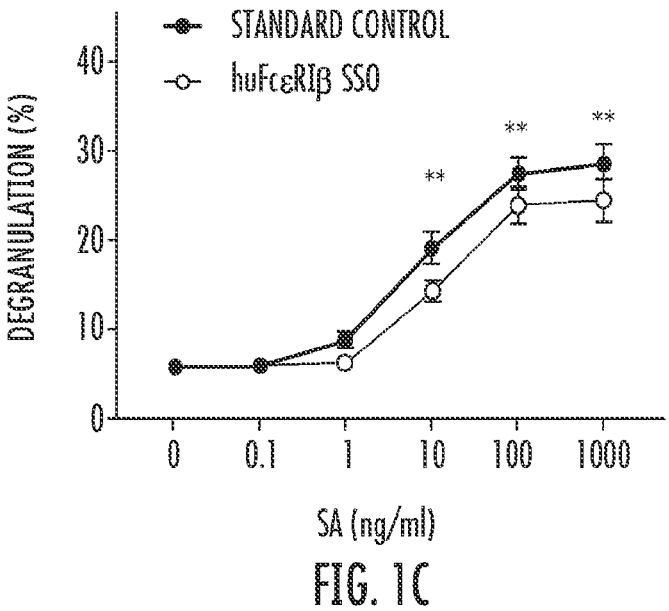
Figure 1D:
Figure 1D:
Figure 1D:
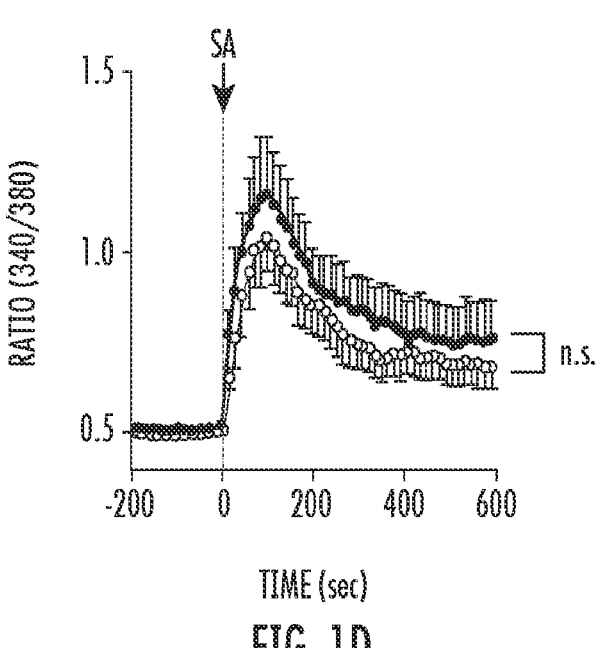

These data demonstrated the potential of this approach to target MCs, if it translates to humans. However, FcεRIβ SSOs are less effective in huMCs. We employed exon skipping of FcεRIβ exon 3 to remove the region of mature mRNA encoding the first transmembrane domain of the FcεRIβ protein. We targeted the FcεRIβ mRNA with the SSO with sequence ATAGATATATACT- CACAAATATGGCTCC (SEQ ID NO: 26) to induce exon skipping of exon 3. However, despite efficient exon skipping of FcεRIβ (FIG. 1A) a maximum of ~60% reduction in surface FcεRIα can be achieved (FIG. 1B). We also utilized FcεRIβ with SSOs targeting an internal region of FcεRIβ exon 3 with the sequence CACAAATATGGCTCCCCAGAATGGA, that also achieved highly efficient exon skipping and gave comparable results (Cruse et al., 2016). Another SSO targeting FcεRIβ exon 3 with the sequence AGTACAGAGCAGACAACTGTTCCA was comparable in efficacy. Regardless of the target SSo tested, minor reductions in degranulation (FIG. 1C) and $Ca^{2+}$ influx were observed, although the latter did not reach significance (FIG. 1D). One explanation for lack of translation to humans is that human FcεRIα can traffic to the plasma membrane in the absence of FcεRIβ when transfected into cell lines (Alber et al., 1991; Donnadieu et al., 2000; On et al., 2004). However, this is unlikely the mechanism, because while it could explain reduced efficacy in surface FcεRI expression, it cannot explain the degranulation and $Ca^{2+}$ data. FcεRIβ amplifies FcεRI signaling by 10 fold in vitro and in vivo, as shown with humanized FcεRIα (Alber et al., 1991; Dombrowicz et al., 1996; Dombrowicz et al., 1998; Donnadieu et al., 2000; On et al., 2004) and trimeric FcεRI does not trigger robust $Ca^{2+}$ influx (Dombrowicz et al., 1998). Thus, FcεRIβ may be dispensable for FcεRI function in huMCs, where an FcεRIβ-like protein may compensate for FcεRIβ.

Example 3

HuMCs Express Multiple MS4A Proteins with High Sequence Homology to FcεRIβ

Figure 2A:
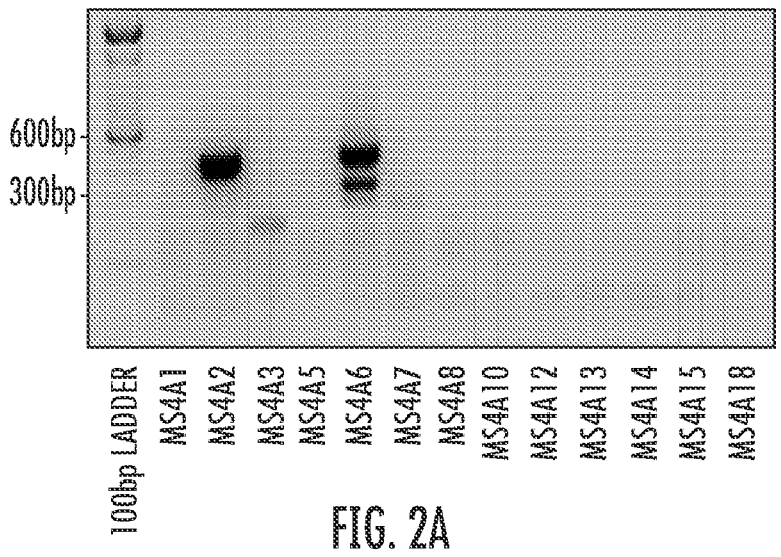
FIGS. 2A-2C. MS4A family expression in human LAD2 mast cells.
Figure 2B:
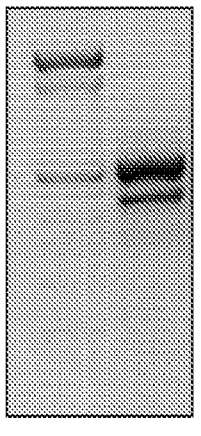

Other members of the gene family that includes FcεRIβ could be FcεRIβ-like proteins. It was determined that LAD2 human MCs express MS4A2 (FcεRIβ), MS4A3, MS4A4A, MS4A6A and MS4A7 under standard culture conditions (FIGS. 2A and 2B). RT-PCR for the other known MS4A genes were negative under normal culture conditions. MS4A3 and MS4A7 were expressed, as shown for LAD2 cells (FIG. 2A), but expression was almost undetectable under standard conditions suggesting these genes are unlikely to be the primary FcεRIβ-like protein. Since MS4A2 (FcεRIβ), MS4A4A, and MS4A6A are expressed at similar levels, MS4A4 and MS4A6A are the most likely candidates for an FcεRIβ-like protein in huMCs.

Example 4

MS4A6A Promotes Surface FcεRI Expression and IgE-Dependent Degranulation

Figure 2C:
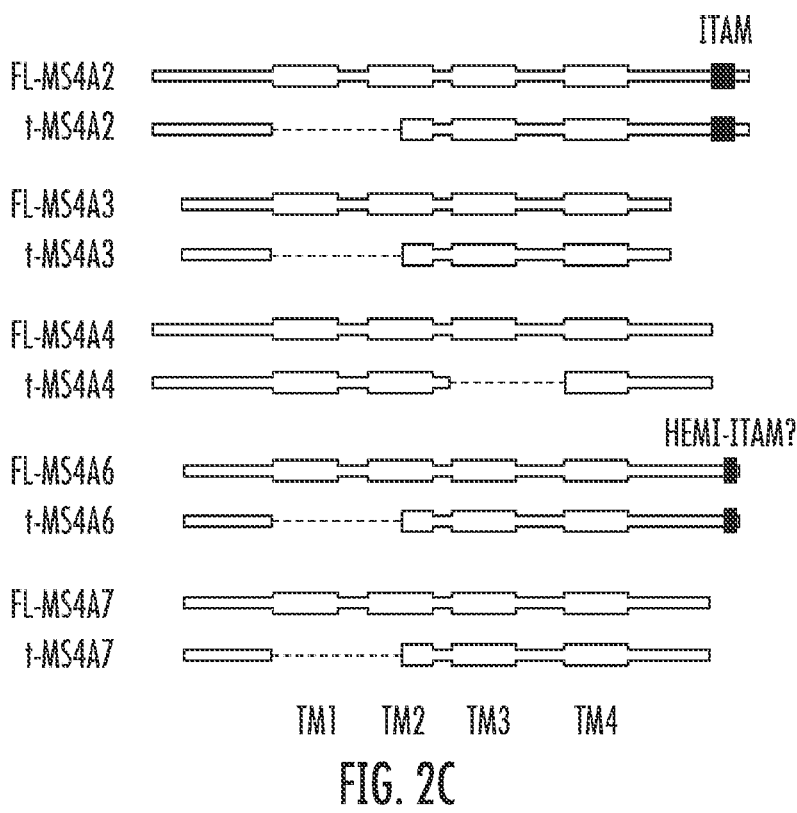
Figure 3:
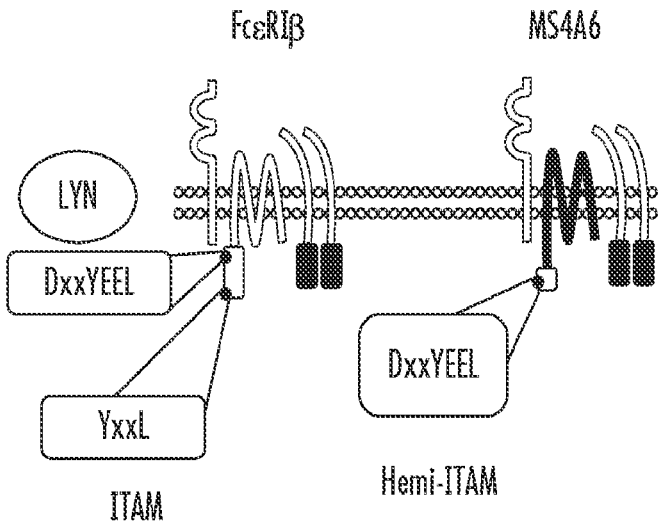
FIG. 3. MS4A6A contains a putative hemi-ITAM. MS4A6A sequencing showed that it contained a putative hemi-ITAM domain with the consensus sequence DxxYxxL in the C-terminus equivalent to the first DxxYxxL in the FcεRIβ ITAM. The first tyrosine residue of the FcεRIβ ITAM is known to bind Lyn and the hemi-ITAM of MS4A6A contains the same sequence as the Lyn binding region of FcεRIβ.
Figure 4A:
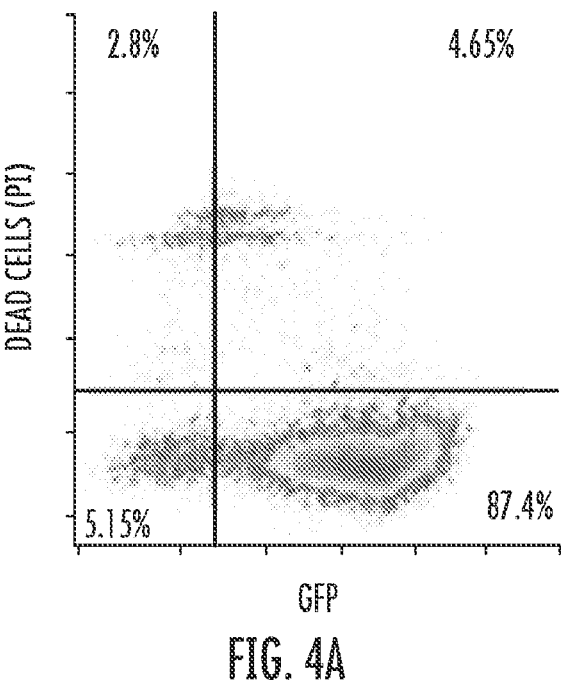
FIGS. 4A-4I. Human mast cells express MS4A6A, which contains a potential hemi-ITAM motif and has a modest role in mast cell degranulation and surface FcεRIβ expression.
Figure 4B:
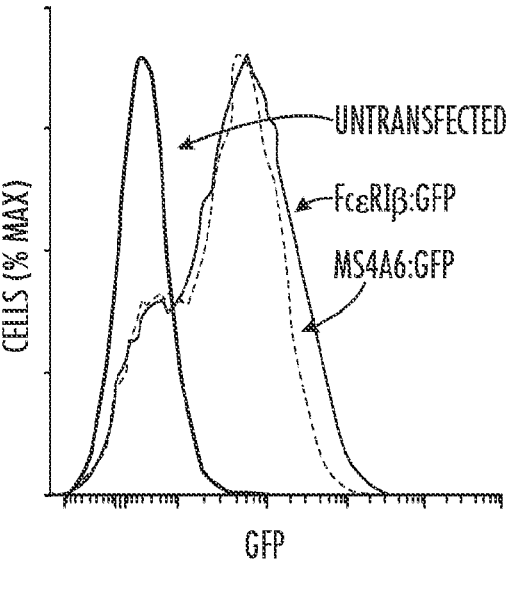
Figure 4C:
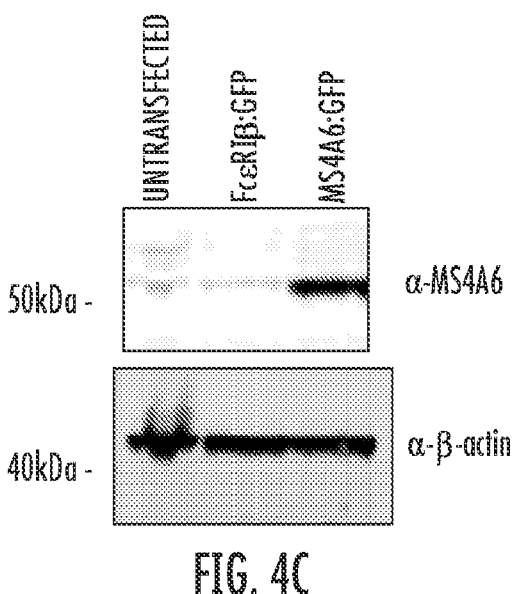
Figure 4D:
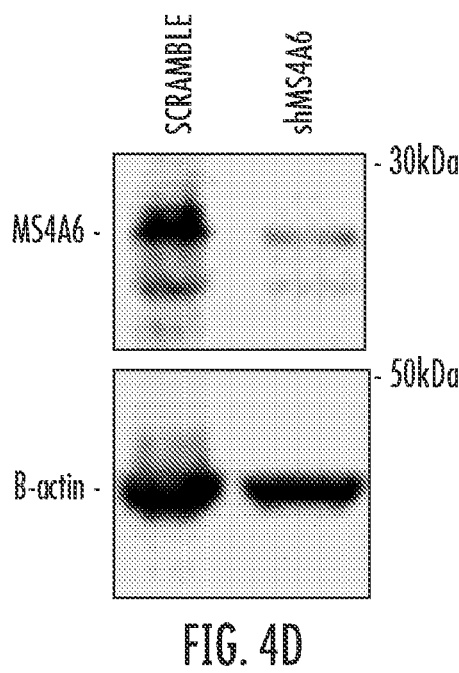
Figures 4E, 4F, 4G:
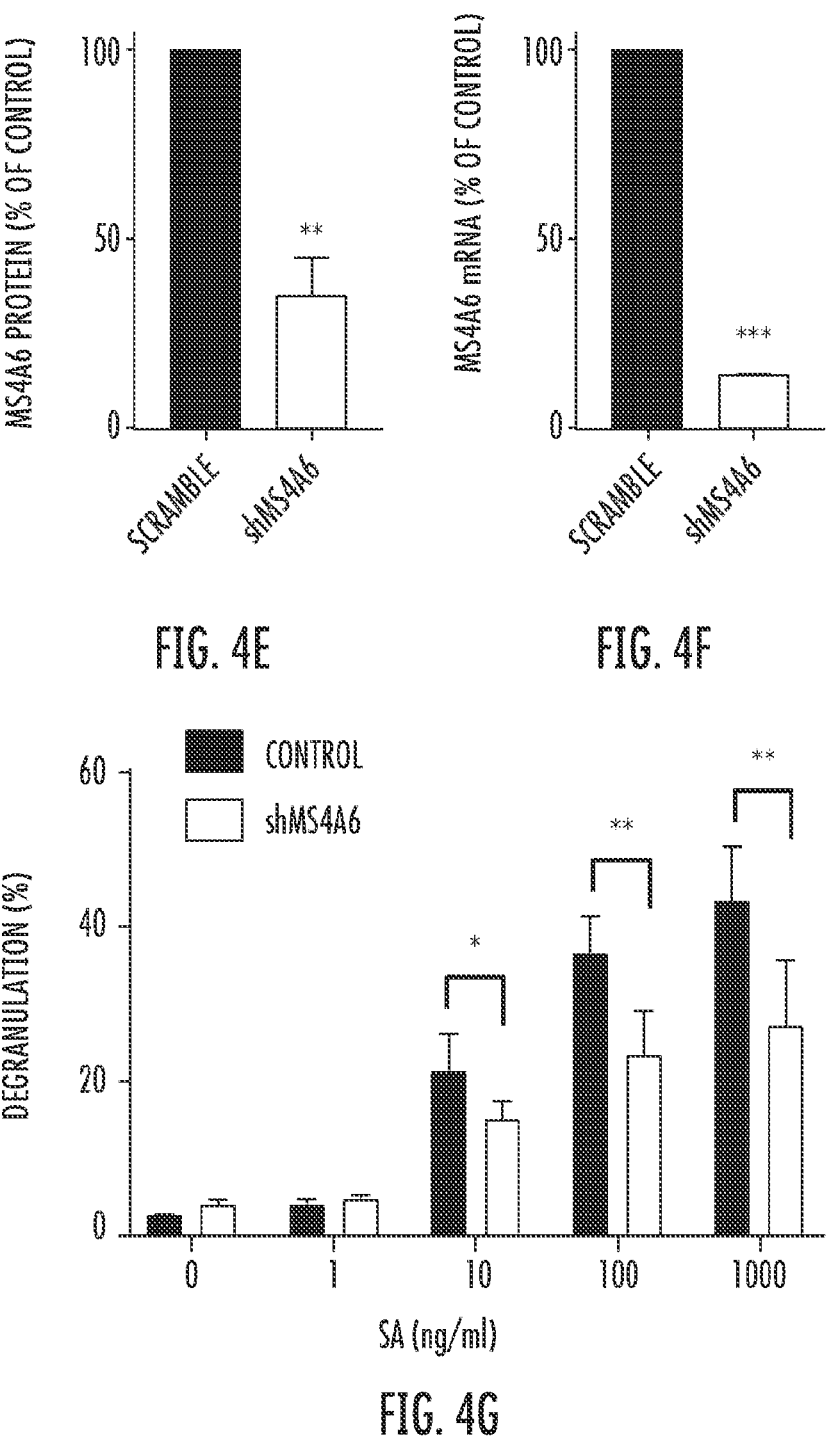

That MS4A6A could traffic FcεRI and act as an FcεRIβ-like protein was examined, because MS4A6A and MS4A2 (FcεRIβ) have conserved features (FIG. 2C). MS4A2 (FcεRIβ) has a truncated isoform that does not traffic to the plasma membrane or associate with FcεRI (Cruse et al., 2010; Cruse et al., 2013; Cruse et al., 2016). This alternative splicing of MS4A2 (FcεRIβ) is likely a regulatory process to alter FcεRI expression at the surface without requirement to alter the level of gene expression. MS4A6A has equivalent alternative splicing (see FIGS. 2A and 2C). Sequencing the RT-PCR bands of MS4A6A confirmed that the novel alternative splicing exactly aligned with MS4A2 (FcεRIβ). Sequencing also determined that MS4A6A contains a putative cytoplasmic hemi-ITAM that is predicted to have the capacity to bind Lyn kinase and signal similarly to the MS4A2 (FcεRIβ) ITAM (FIG. 3).

shRNA was first employed to knockdown gene expression using standard RNAi approaches with lentiviral delivery as described (Cruse et al., 2013; Cruse et al., 2015) to knockdown both MS4A6A isoforms. An antibody was then tested for specificity to MS4A6A that was to be used for confirming MS4A6A knockdown. MS4A6A and FcεRIβ were cloned and transfected into LAD2 cells with GFP tags to confirm expression by flow cytometry (see FIGS. 4A and 4B). After confirming transfection, cell lysates were extracted and stained by Western blot to validate MS4A6A antibody (FIG. 4C). Knockdown of MS4A6A variants was then performed and knockdown of both MS4A6A variants was confirmed by Western blot (see FIGS. 4D and 4E), as well as quantitative PCR (FIG. 4F). Knockdown of MS4A6A inhibited MC degranulation (see FIG. 4G) and calcium influx (FIG. 4H) comparably to exon skipping FcεRIβ (see FIG. 1C). Knockdown of either FcεRIβ or MS4A6A both resulted in reduction of surface FcεRI expression (see FIG. 4I). Thus, MS4A6A and FcεRIβ may perform related functions in degranulation and trafficking of FcεRI, and disruption of either protein alone could be inadequate to eliminate IgE-mediated degranulation.

Example 5

Full-Length MS4A6A Promotes FcεRI Function

Figures 4H, 4I, 5A, 5B:
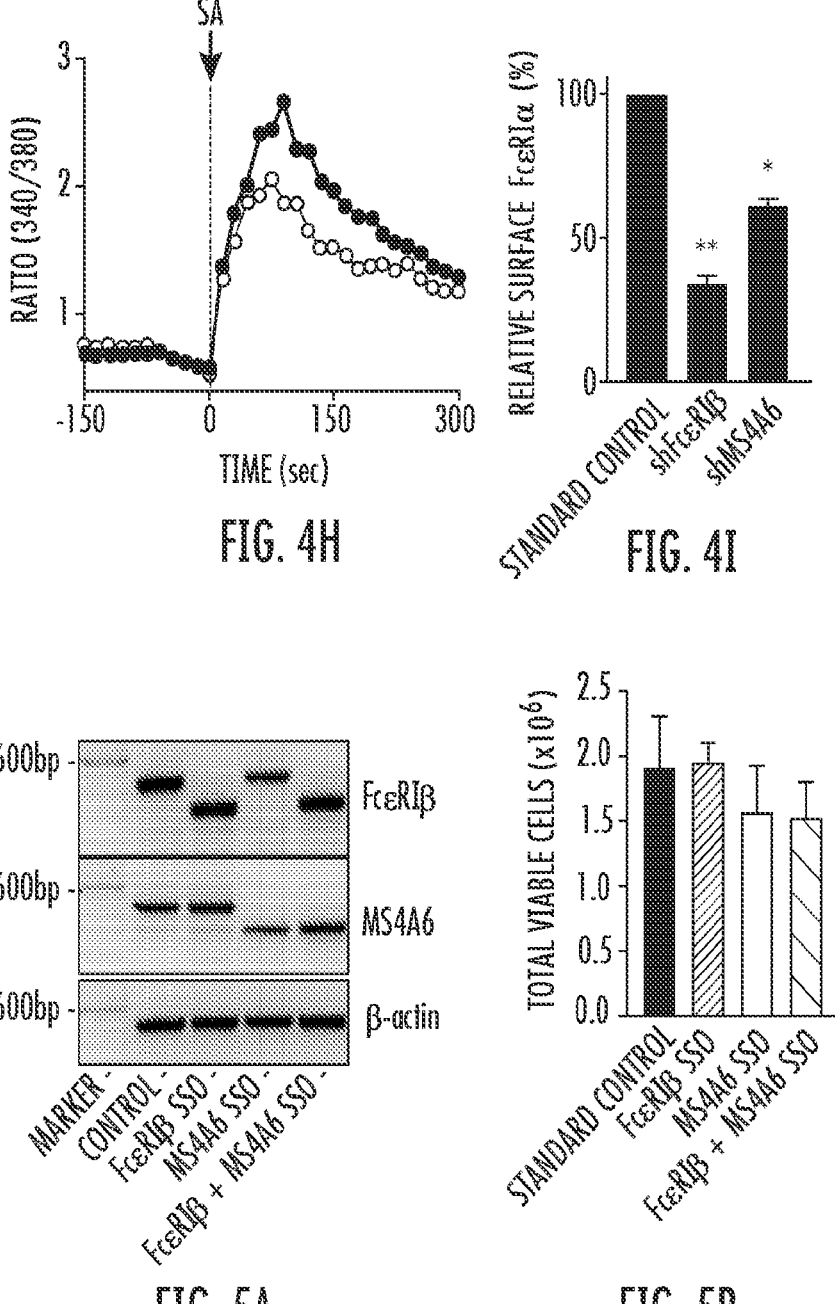
FIGS. 5A-5G. Exon skipping of MS4A6A works comparably to FcεRIβ and SSOs targeting either FcεRIβ or MS4A6A alone are insufficient to stop degranulation of human mast cells, but combined SSOs targeting both proteins have a synergistic effect.
Figure 5C:
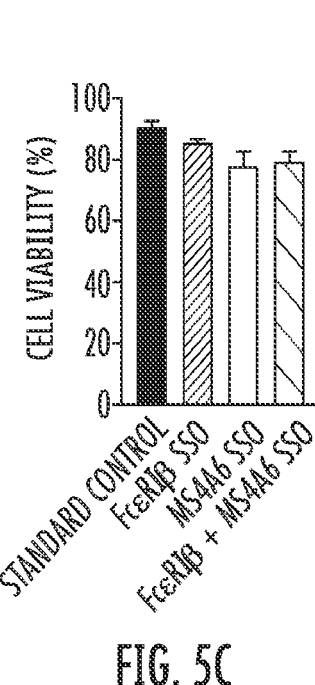
Figure 5D:
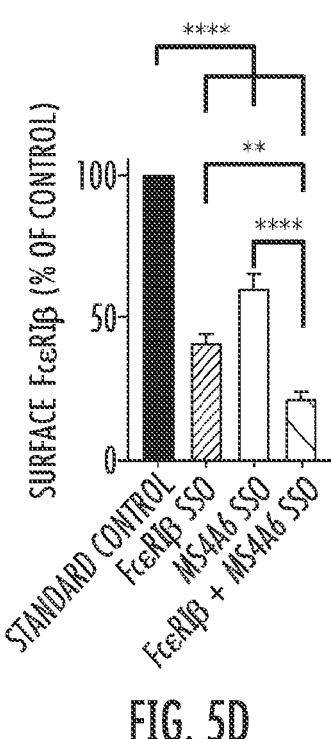
Figure 5E:
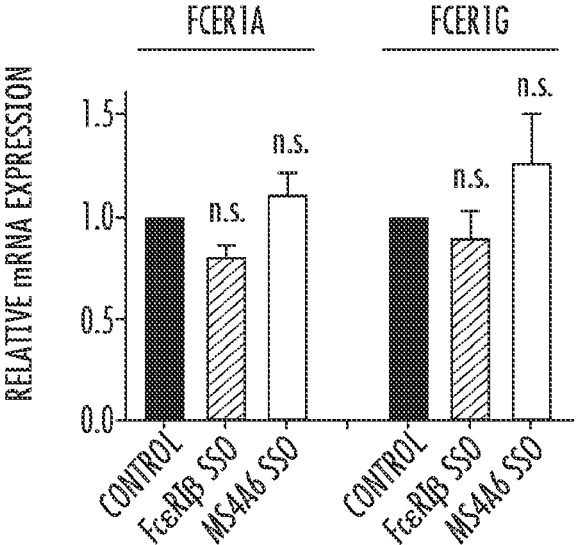
Figure 5F:
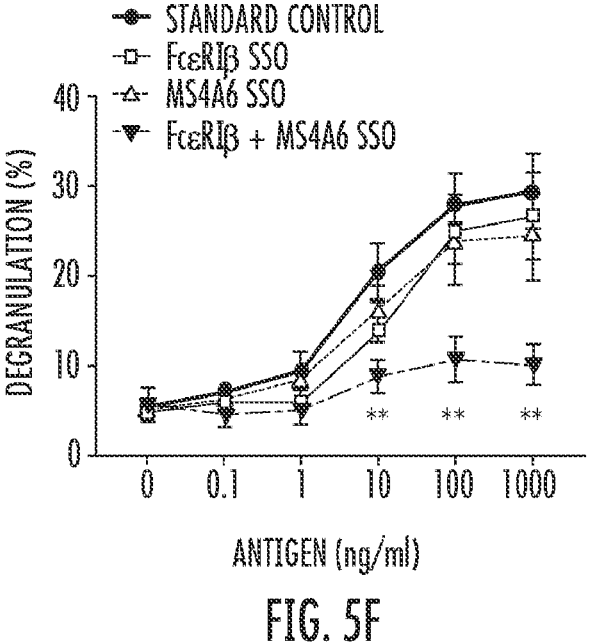
Figure 5G:
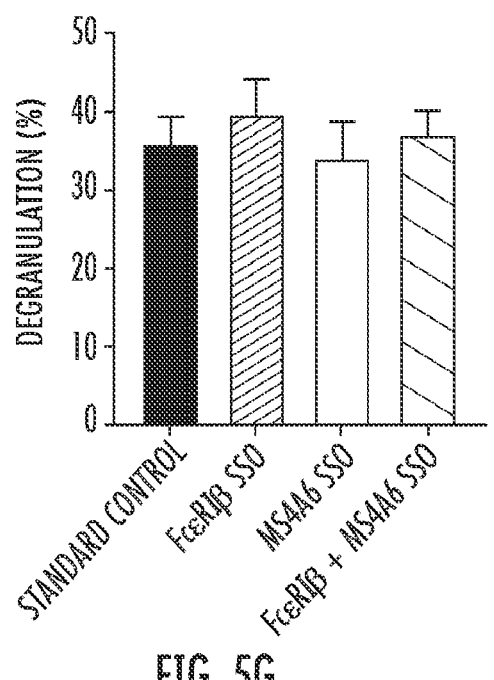

The highly conserved splicing of the 1st and 2nd transmembrane (TM) domains of FcεRIβ and MS4A6A (see FIG. 2C) indicate that exon 4 of MS4A6A, which aligns almost exactly with exon 3 of FcεRIβ, is also critical for MS4A6A function. The SSO method that was used to induce exon skipping targeting exon 3 of FcεRIβ with sequence ATAGATATATACTCACAAATATGGCTCC (SEQ ID NO: 26), was employed herein in the context of exon skipping the target exon 4 of MS4A6A with the sequence TCTGGATAGTCTGTGGGAAGAGAAA (SEQ ID NO: 22), and it was determined that MS4A6A exon 4 skipping with SSO efficiently and specifically induced exon skipping of exon 4 of MS4A6A, while FcεRIβ exon 3 SSO was specific for exon skipping of MS4A2 (see FIG. 5A). Employing both FcεRIβ exon 3 and MS4A6 exon 4 SSOs simultaneously, induced exon skipping of both mRNAs (FIG. 5A). Exon skipping with exon 3 of FcεRIβ or exon 4 of MS4A6A with SSOs did not significantly affect cell number (FIG. 5B) or viability (FIG. 5C). However, MS4A6A exon 4 and FcεRIβ exon 3 SSOs reduced surface FcεRIα expression (FIG. 5) comparably to knockdown of FcεRIβ or MS4A6A using standard shRNA lentiviral approaches (FIG. 4I). Combined FcεRIβ exon 3 SSO and MS4A6A exon 4 SSO had an additive effect reducing FcεRI surface expression by >80% (FIG. 5D). Despite the reduction in surface FcεRIα expression with FcεRIβ exon 3 SSO and MS4A6A exon 4 SSO (FIG. 5D), levels of FcεRIα and FcεRIγ transcripts were not altered suggesting a defect in FcεRI trafficking, rather than expression when either FcεRIβ or MS4A6A were targeted (FIG. 5E). Degranulation in response to IgE-crosslinking with SSOs for exon 3 of FcεRIβ or exon 4 of MS4A6A alone had only a minor effect, but FcεRIβ exon 3 SSO and MS4A6A exon 4 SSO used in combination, markedly inhibited IgE-dependent degranulation (FIG. 5F), but not compound 48/80 (FIG. 5G). Taken together, these data suggested that FcεRIβ exon 3 and MS4A6A exon 4 play redundant or partially redundant roles in FcεRI trafficking and signaling. Lack of effect with other activating mast cell receptors (MRGPRX2 activation with compound 48/80 in this case) demonstrate specificity to FcεRI rather than a generalized response.

MS4A6A exon 4 can be targeted comparably to FcεRIβ exon 3 by inducing alternative splicing to remove the first transmembrane domain of the MS4A6A or FcεRIβ protein, respectively. The result of exon skipping either exon 3 of FcεRIβ or exon 4 of MS4A6A is a reduced surface expression of FcεRIα, which is likely due to reduced trafficking to the plasma membrane. The presently disclosed data suggest that the full length splice variants of both FcεRIβ and MS4A6A can form subunits of FcεRI and traffic the receptor complex to the plasma membrane in human mast cells (see FIGS. 4I and 5D). Exon skipping either protein to induce expression of only the truncated splice variant of each protein that lacks the first and second transmembrane domains appears to reduce the incorporation of that protein into FcεRI complexes and reduce surface expression of FcεRIα (FIG. 5D). However, the remaining FcεRI complexes that contain the other protein are capable of achieving enough of a signal for degranulation to occur. Exon skipping both proteins to remove the first two transmembrane domains of each protein, on the other hand, can stop degranulation from occurring.

Figure 6A:
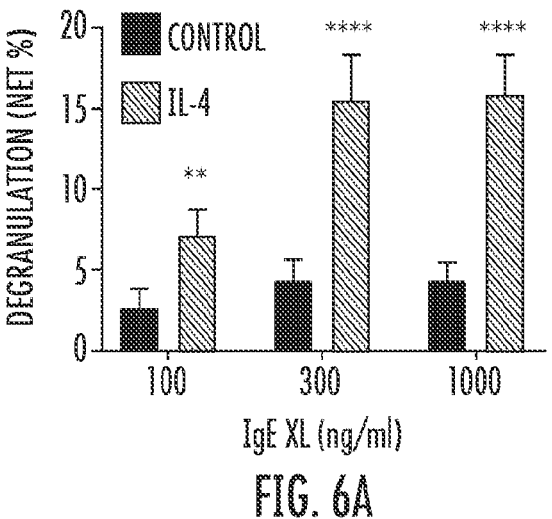
FIGS. 6A-6F. Exon skipping of MS4A6A and FcεRIβ is comparable in primary human mast cells.
Figure 6B:
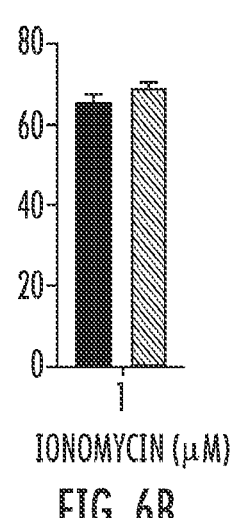
Figure 6C:
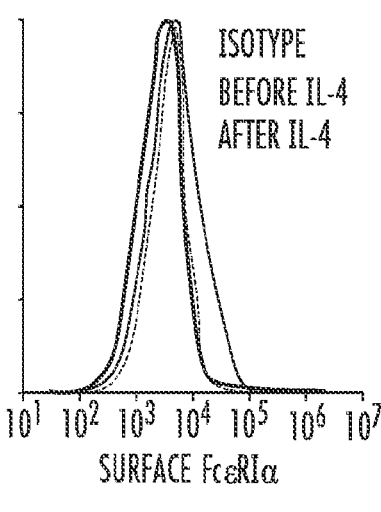
Figure 6D:
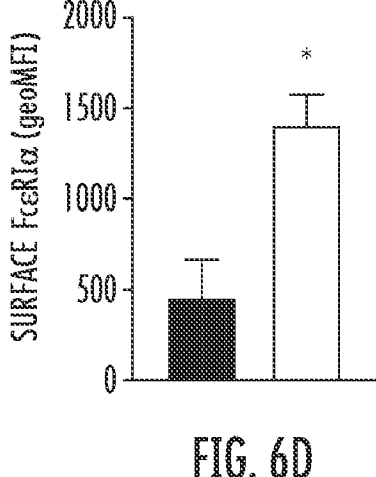
Figure 6E:
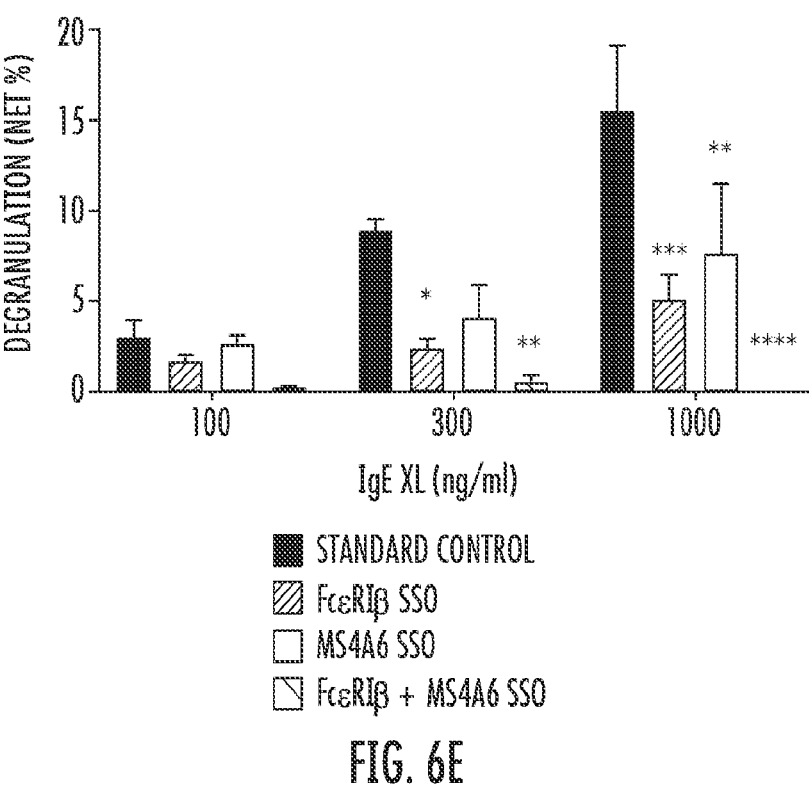
Figure 6F:
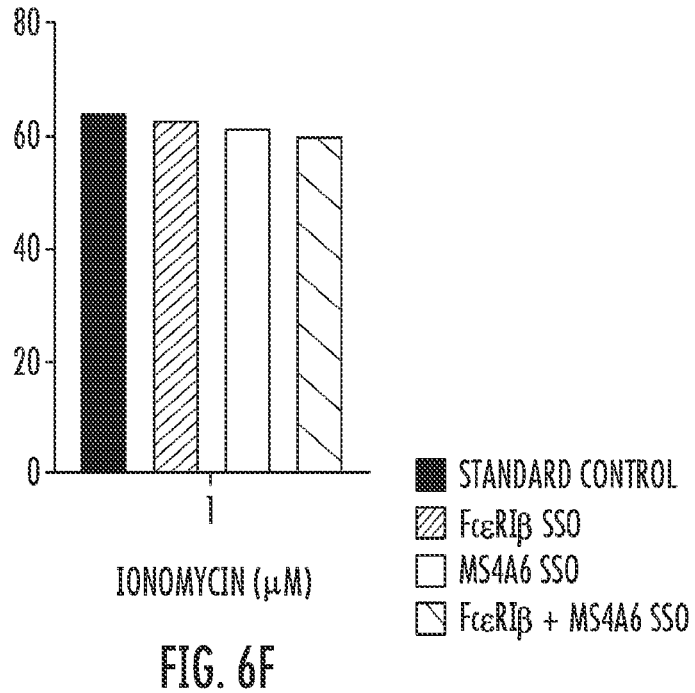

These data were next confirmed for exon skipping of FcεRIβ exon 3 and MS4A6A exon 4 using degranulation in primary cord blood-derived mast cells (CBDMCs). CBDMCs are known to maintain an immature phenotype and must be primed with IL-4 to respond to IgE crosslinking (FIG. 6A) and upregulated surface expression of FcεRI (see FIGS. 6C and 6D). Once primed, they responded and exon skipping of FcεRIβ exon 3 and MS4A6A exon 4 alone and in combination, were comparable to LAD2 mast cells (FIG. 6E). The positive control with ionomycin (FIG. 6B) was not affected by exon skipping mRNA for either protein (FIG. 6F).

Figure 7:
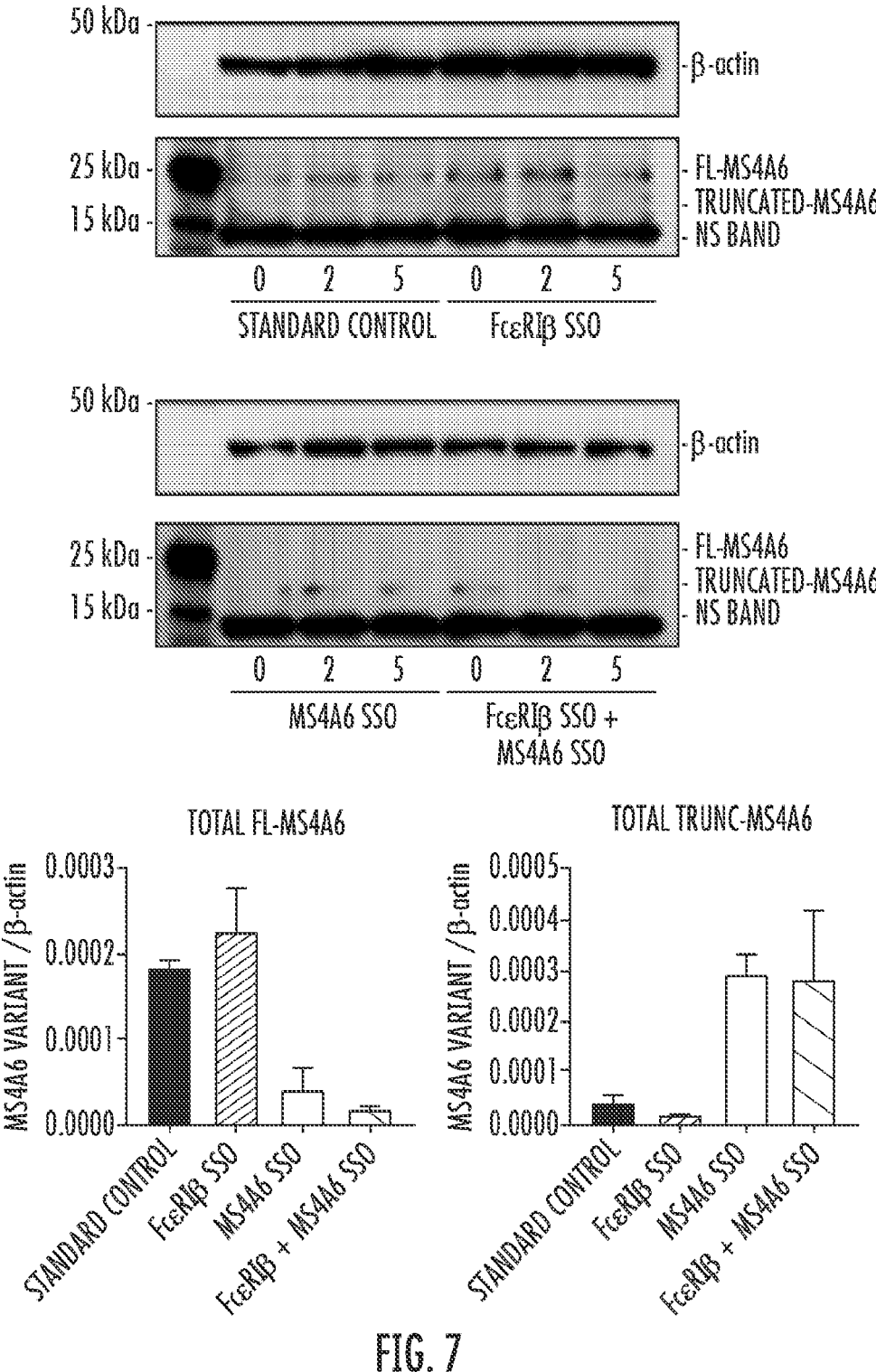
FIG. 7. Exon skipping of MS4A6A forces expression of the truncated isoform at the protein level. The MS4A6A antibody that was validated in FIG. 4, recognized both the full length (FL-MS4A6A) and truncated (truncated-MS4A6A) MS4A6A isoforms. MS4A6A SSO, but not FcεRIβ SSO, resulted in the expression of truncated MS4A6A. NS band: non-specific band of <15 kDa. FL MS4A6A is predicted to be 25 kDa and truncated MS4A6A is predicted to be 20 kDa.

Exon skipping of exon 4 of MS4A6A results in the production of the truncated MS4A6A protein rather than the full length version confirming our proposed mechanism (FIG. 7). This exon skipping of MS4A6A exon 4 is specific with no cross-reactivity with FcεRIβ exon 3 evident, allowing for the study of full length MS4A6A function.

Figure 8A:
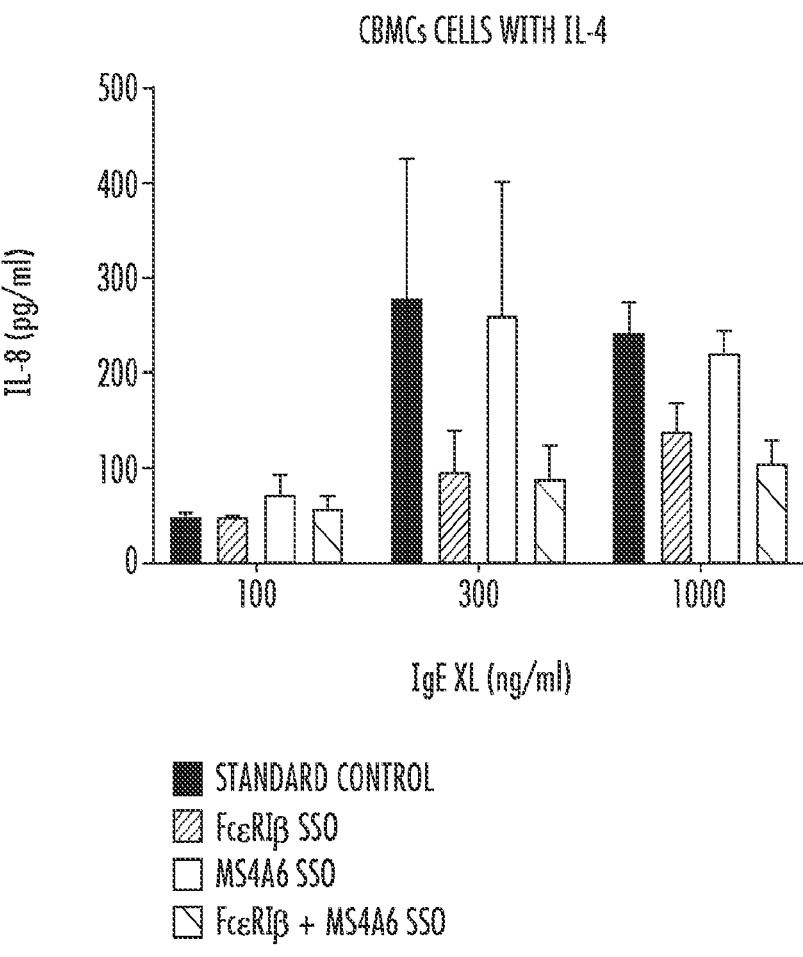
FIGS. 8A and 8B.FcεRIβ, but not MS4A6 drive FcεRI-dependent cytokine release in cord-blood-derived MCs.
Figure 8B:
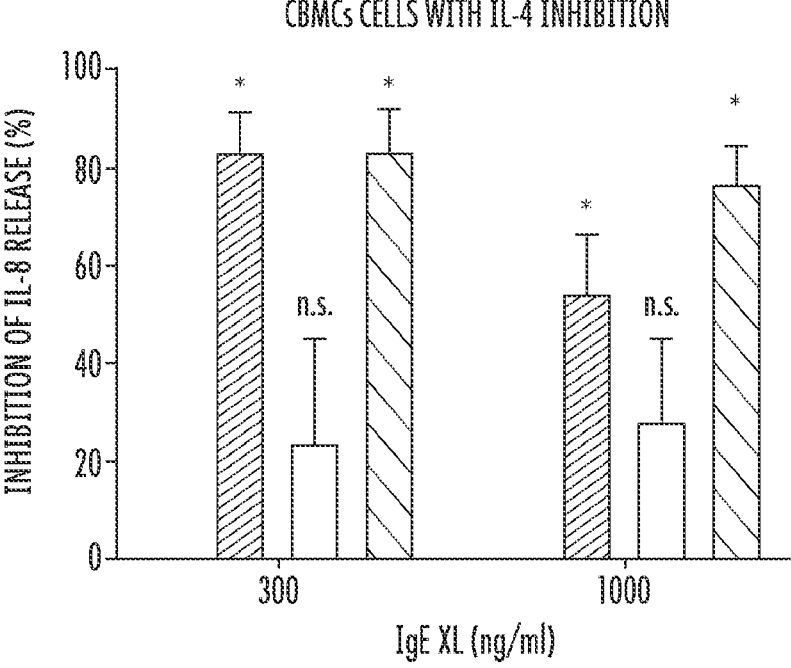

Finally, the effects of exon skipping of exon 3 of FcεRIβ and exon 4 of MS4A6A on cytokine synthesis was tested. In contrast to degranulation, it appeared as though MS4A6A was playing only a minimal role, or no role in IL-8 production in cord blood cells and that IL-8 production was mediated FcεRIβ alone (FIG. 8A). There was variation on the amount of cytokine release between cord blood MC donors (FIG. 8A), but when each donor was analyzed as % inhibition of cytokine release compared to the standard control for each donor, a consistent and significant inhibition of cytokine production (IL-8) was achieved only when FcεRIβ exon 3 was targeted (FIG. 8B). Taken together, these data suggested that FcεRIβ, but not MS4A6A, was a critical driver of cytokine production in these cells.

DISCUSSION OF THE EXAMPLES

Asthma and related allergic diseases are common. Asthma affects up to one in ten people in developed countries. About 10% of patients with asthma cannot be controlled with current therapeutic approaches. In addition to the significant morbidity associated with uncontrolled asthma, the economic burden is greater than tuberculosis and HIV/AIDS combined. Allergic diseases are increasing dramatically in prevalence and up to 50% of children in the developed world test positive to allergens and thus allergy medication is of great interest. Most current treatments target the effects of the mediators released by mast cells rather than targeting the mast cell directly, or use corticosteroids, which target a wide range of cells. The approach that is disclosed herein is a more direct approach.

The data disclosed herein demonstrate, for the first time, a redundant or partially redundant function for the membrane spanning 4A (MS4A) gene family member, MS4A6A, and another MS4A gene family member FcεRIβ (encoded by MS4A2), in trafficking and signaling of the high affinity IgE receptor, FcεRI. MS4A6A is a protein of unknown function that is in the same gene family as FcεRIβ (MS4A2). We are the first to report its function and demonstrate that the first two transmembrane domains of MS4A6A are critical for its function in FcεRI biology. FcεRIβ also functions in a comparable way and again, the first two transmembrane domains are critical for its function in FcεRI biology (Cruse et al., 2010, Cruse et al., 2013, Cruse et al., 2016). We demonstrate here that exon skipping human FcεRIβ exon 3 to remove the first two transmembrane domains reduces FcεRI surface expression, but is insufficient to eliminate degranulation in human mast cells in response to IgE activation. The same is true for MS4A6A exon 4 where exon skipping MS4A6A exon 4 to remove the first two transmembrane domains reduces surface FcεRI expression, but fails to eliminate IgE-dependent degranulation in human mast cells. However, targeting both proteins with these SSOs simultaneously, eliminates human mast cell degranulation in response to antigens through IgE. This demonstrates not only a function for MS4A6A, but also identifies that both FcεRIβ and MS4A6A exhibit redundancy in FcεRI function and thus both proteins contribute to IgE-dependent mast cell activation.

Surface FcεRI expression in mast cells can be eliminated. In addition, mast cells within specific tissues could be targeted. For example, a cream could be developed to target mast cells specifically in the skin to treat skin allergies. For asthma, an inhaler could target mast cells specifically in the lung. In allergic rhinitis, a nasal spray delivering AONs to the nasal mucosa could be used. These diseases have unmet clinical need and there are no specific inhibitors of mast cell function that are effective when administered chronically in vivo. Therefore, the potential of this approach is very significant.

Using antisense oligonucleotides (AONs) in different formulations such as inhaled micro-particles and topical creams have been reported and thus there are many applications for an AON drug that would reduce mast cell activation. If an AON and delivery method that could be administered in a cream is developed to target skin mast cells, this could eliminate mast cell activation in atopic dermatitis. An aerosol of AONs delivered as an inhaler to the lung would target lung mast cells in asthma and protect against IgE-mediated lung inflammation and wheezing in asthma. Similarly, a nasal spray would target mast cells in the nasal mucosa that could be used to target these cells specifically in allergic rhinitis. In addition, oral administration of AONs against FcεRI could be administered to protect against activation of mast cells in the gut and food allergy and anaphylaxis.

The foregoing EXAMPLES as set forth herein have been presented for purposes of illustration and description. These examples are not intended to limit the disclosure to the form disclosed herein, as variations and modifications commensurate with the teachings of the description of the disclosure, and the skill or knowledge of the relevant art, are within the scope as set forth herein. It is intended that the appended claims be construed to include alternative embodiments to the extent permitted by the prior art.

REFERENCES

All references listed in the instant disclosure and in the Appendices attached hereto, including but not limited to all patents, patent applications and publications thereof, scientific journal articles, and database entries (including but not limited to GENBANK® biosequence database entries and including all annotations available therein) are incorporated herein by reference in their entireties to the extent that they supplement, explain, provide a background for, and/or teach methodology, techniques, and/or compositions employed herein. The discussion of the references is intended merely to summarize the assertions made by their authors. No admission is made that any reference (or a portion of any reference) is relevant prior art. The right to challenge the accuracy and pertinence of any cited reference is expressly reserved.

Alber et al. (1991) Structure-function relationships in the mast cell high affinity receptor for IgE. Role of the cytoplasmic domains and of the beta subunit. J Biol Chem 266:22613-22620.

Alshahrani et al. (2014) CEACAM2 negatively regulates hemi (ITAM-bearing) GPVI and CLEC-2 pathways and thrombus growth in vitro and in vivo. Blood 124:2431-2441.

Bangur et al. (2004) Identification and characterization of L985P, a CD20 related family member over-expressed in small cell lung carcinoma. Int J Oncol 25:1583-1590.

Berger et al. (2000) Universal bases for hybridization, replication and chain termination. Nuc Acid Res 28:2911-2914.

Bieber et al. (1992) Human epidermal Langerhans cells express the high affinity receptor for immunoglobulin E (Fc epsilon RI). The Journal of Experimental Medicine 175:1285-1290.

Bubien et al. (1993) Transfection of the CD20 cell surface molecule into ectopic cell types generates a $Ca^{2+}$ conductance found constitutively in B lymphocytes. J Cell Biol 121:1121-1132.

Bulfone-Paus & Rahri (2015) Mast cells as regulators of T cell responses. Front Immunol 6:394.

Cheung et al. (2010) Cutting edge: CD49d+ neutrophils induce FcεRI expression on lung dendritic cells in a mouse model of postviral asthma. The Journal of Immunology 185:4983-4987.

Cruse & Bradding (2016) Mast cells in airway diseases and interstitial lung disease. European Journal of Pharmacology 778:125-138.

Cruse et al. (2010) A novel FcεRIβ-chain truncation regulates human mast cell proliferation and survival. The FASEB Journal 24:4047-4057.

Cruse et al. (2013) A truncated splice-variant of the FcεRIβ receptor subunit is critical for microtubule formation and degranulation in mast cells. Immunity 38:906-917.

Cruse et al. (2015) The CD20 homologue MS4A4 directs trafficking of KIT toward clathrin-independent endocytosis pathways and thus regulates receptor signaling and recycling. Mol Biol Cell 26:1711-1727.

Cruse et al. (2016) Exon skipping of FcεRIβ eliminates expression of the high-affinity IgE receptor in mast cells with therapeutic potential for allergy. Proc Natl Acad Sci USA 113:14115-14120.

Dalerba et al. (2011) Single-cell dissection of transcriptional heterogeneity in human colon tumors. Nat Biotechnol 29:1120-1127.

De Angelis et al. (2002) Chimeric snRNA molecules carrying antisense sequences against the splice junctions of exon 51 of the dystrophin pre-mRNA induce exon skipping and restoration of a dystrophin synthesis in Delta 48-50 DMD cells. Proc Natl Acad Sci USA 99:9456-9461.

Dehlink et al. (2010) Relationships between levels of serum IgE, cell-bound IgE, and IgE-receptors on peripheral blood cells in a pediatric population. PLoS One 5:e12204.

Denti et al. (2006) Chimeric adeno-associated virus/antisense U1 small nuclear RNA effectively rescues dystrophin synthesis and muscle function by local treatment of mdx mice. Hum Gene Ther 17:565-574.

Dombrowicz et al. (1996) Anaphylaxis mediated through a humanized high affinity IgE receptor. J Immunol 157: 1645-1651.

Dombrowicz et al. (1998) Allergy-associated FcRβ is a molecular amplifier of IgE- and IgG-mediated in vivo responses. Immunity 8:517-529.

Donnadieu et al. (2000) A second amplifier function for the allergy-associated FcεRIβsubunit. Immunity 12:515-523.

Furumoto et al. (2004) The FcepsilonRIbeta immunoreceptor tyrosine-based activation motif exerts inhibitory control on MAPK and IkappaB kinase phosphorylation and mast cell cytokine production. J Biol Chem 279:49177-49187.

Galli & Tsai (2012) IgE and mast cells in allergic disease. Nature Medicine 18(5):693-704.

Gould & Sutton (2008) IgE in allergy and asthma today. Nature Reviews Immunology 8:205-217.

Goyenvalle et al. (2004) Rescue of dystrophic muscle through U7 snRNA-mediated exon skipping. Science 306:1796-1799.

Greer et al. (2014) Serum IgE clearance is facilitated by human FcεRI internalization. The Journal of Clinical Investigation 124:1187-1198.

Greer et al. (2016) A Family of non-GPCR Chemosensors Defines an Alternative Logic for Mammalian Olfaction. Cell 165:1734-1748.

Hollingworth et al. (2011) Common variants at ABCA7, MS4A6A/MS4A4E, EPHA1, CD33 and CD2AP are associated with Alzheimer's disease. Nat Genet 43:429-435.

Holloway et al. (2001) Expression of the high-affinity IgE receptor on peripheral blood dendritic cells: differential binding of IgE in atopic asthma. Journal of Allergy and Clinical Immunology 107:1009-1018.

Kimura et al. (1996) Downstream signaling molecules bind to different phosphorylated immunoreceptor tyrosine-based activation motif (ITAM) peptides of the high affinity IgE receptor. J Biol Chem 271:27962-27968.

Kinet (1999) The high-affinity IgE receptor (FcεRI): from physiology to pathology. Annual Review of Immunology 17:931-972.

Koslowski et al. (2008) MS4A12 is a colon-selective store-operated calcium channel promoting malignant cell processes. Cancer Res 68:3458-3466.

Kraft & Kinet (2007) New developments in Fcε RI regulation, function and inhibition. Nature Reviews Immunology 7:365-378.

Kraft et al. (2004) The role of the FcεRI β-chain in allergic diseases. International Archives of Allergy and Immunology 135:62-72.

Küster et al. (1992) The gene and cDNA for the human high affinity immunoglobulin E receptor beta chain and expression of the complete human receptor. Journal of Biological Chemistry 267:12782-12787.

Liang & Tedder (2001) Identification of a CD20-, FcepsilonRIbeta-, and HTm4-related gene family: sixteen new MS4A family members expressed in human and mouse. Genomics 72:119-127.

Liang et al. (2001) Structural organization of the human MS4A gene cluster on Chromosome 11q12. Immunogenetics 53:357-368.

Lympany et al. (1992) Genetic analysis of the linkage between chromosome 11q and atopy. Clin Exp Allergy 22:1085-1092.

Manne et al. (2015) Distinct pathways regulate Syk protein activation downstream of immune tyrosine activation motif (ITAM) and hemITAM receptors in platelets. J Biol Chem 290:11557-11568.

Maurer et al. (1994) Expression of functional high affinity immunoglobulin E receptors (Fc epsilon RI) on monocytes of atopic individuals. The Journal of Experimental Medicine 179:745-750.

Maurer et al. (1996) Peripheral blood dendritic cells express Fc epsilon RI as a complex composed of Fc epsilon RI alpha—and Fc epsilon RI gamma—chains and can use this receptor for IgE-mediated allergen presentation. The Journal of Immunology 157:607-616.

Michel et al. (2013) Identification of the novel differentiation marker MS4A8B and its murine homolog MS4A8A in colonic epithelial cells lost during neoplastic transformation in human colon. Cell Death Dis 4:e469.

Naj et al. (2011) Common variants at MS4A4MS4A6E, CD2AP, CD33 and EPHA1 are associated with late-onset Alzheimer's disease. Nat Genet 43:436-441.

On et al. (2004) Molecular dissection of the FcRβ (3 signaling amplifier. Journal of Biological Chemistry 279:45782-45790.

Osborne et al. (1996) The inositol 5'-phosphatase SHIP binds to immunoreceptor signaling motifs and responds to high affinity IgE receptor aggregation. J Biol Chem 271:29271-29278.

Parravicini et al. (2002) Fyn kinase initiates complementary signals required for IgE-dependent mast cell degranulation. Nat Immunol 3:741-748.

Platzer et al. (2015) Dendritic cell-bound IgE functions to restrain allergic inflammation at mucosal sites. Mucosal Immunology 8:516-532.

Sandford et al. (1993) Localisation of atopy and beta subunit of high-affinity IgE receptor (Fc epsilon RI) on chromosome 11q. Lancet 341:332-334.

Singleton et al. (2009) The first transmembrane region of the β-chain stabilizes the tetrameric FcεRI complex. Molecular immunology 46:2333-2339.

Stafford et al. (1994) A 2.8 Mb YAC contig in 11q12-q13 localizes candidate genes for atopy: Fc epsilon RI beta and CD20. Hum Mol Genet 3:779-785.

U.S. Patent Application Publication Nos. 2015/0238627; 2015/0361428; 2015/0376615; 2019/0062756.

U.S. Pat. Nos. 6,806,084; 7,973,015; 8,236,557; 8,268,962; 8,304,398; 8,361,979; 8,569,256; 8,765,703; 8,802,645; 8,946,183; 9,080,170; 9,238,042; 9,598,703; 9,738,891; 9,862,945; 10,030,894; 10,188,633; and 10,590,420.

Vasudev et al. (2012) Expression of high-affinity IgE receptor on human peripheral blood dendritic cells in children. PLoS One 7:e32556.

Virk et al. (2016) Mast cells and their activation in lung disease. Transl Res 174:60-76.

Ye et al. (2014) MS4A8B promotes cell proliferation in prostate cancer. Prostate 74:911-922.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. An antisense oligomer comprising 25 to 50 linked nucleosides, wherein the antisense oligomer is targeted to a region of a pre-mRNA encoding a MS4A6A protein, and wherein the targeted region comprises sequences involved in splicing of the MS4A6A-encoding pre-mRNA, wherein the antisense oligomer comprises SEQ ID NO: 22.

2. The antisense oligomer of claim 1, wherein hybridization of the antisense oligomer to the MS4A6A-encoding pre-mRNA alters splicing of the pre-mRNA.

3. The antisense oligomer of claim 1, wherein hybridization of the antisense oligomer to the MS4A6A-encoding pre-mRNA reduces cell surface expression of high affinity IgE receptor (FcεRI).

4. The antisense oligomer of claim 1, wherein the targeted region comprises at least a portion of a polynucleotide sequence selected from the group consisting of an intron sequence, an exon sequence, a sequence comprising an intron/exon junction, a splice donor sequence, a slice accep-tor sequence, a splice enhancer sequence, a splice branch point sequence, or a polypyrimidine tract.

5. The antisense oligomer of claim 4, wherein the poly-nucleotide sequence is selected from the group consisting of an intron 3 sequence, an exon 4 sequence, a sequence comprising an intron 3/exon 4 junction, an exon 4 splice donor sequence, an exon 4 slice acceptor sequence, an exon 4 splice enhancer sequence, an exon 4 splice branch point sequence, an exon 4 polypyrimidine tract, or an exon encoding the first transmembrane domain of the MS4A6A protein.

6. The antisense oligomer of claim 1, wherein the MS4A6A protein is a human MS4A6A protein.

7. The antisense oligomer of claim 5, wherein hybridiza-tion of the antisense oligomer to the MS4A6A pre-mRNA results in production of a mature MS4A6A mRNA molecule that lacks at least a portion of exon 4.

8. The antisense oligomer of claim 5, wherein hybridization of the antisense oligomer to the MS4A6A pre-mRNA results in production of an mRNA molecule encoding a truncated MS4A6A protein.

9. The antisense oligomer of claim 1, wherein the 25 to 50 linked nucleosides comprises, consists essentially of, or consists of a targeting nucleic acid sequence sufficiently complementary to a target nucleic acid sequence in the MS4A6A-encoding pre-mRNA such that the oligonucleotide specifically hybridizes to the target sequence.

10. The antisense oligomer of claim 9, wherein hybridization of the antisense oligomer to the MS4A6A-encoding pre-mRNA alters splicing of the pre-mRNA, reduces cell surface expression of high affinity IgE receptor (FcεRI), or both.

11. The antisense oligomer of claim 1, wherein the target sequence comprises, consists essentially of, or consists of at least a portion of a polynucleotide sequence selected from the group consisting of SEQ ID NOs: 1, 3, 7, or 9.

12. The antisense oligomer of claim 1, wherein the targeting sequence is complementary to at least portion of a sequence selected from the group consisting of SEQ ID NOs: 1, 3, 7, or 9.

13. The antisense oligomer of claim 1, wherein the antisense oligomer is an antisense RNA molecule.

14. The antisense oligomer of claim 13, wherein the antisense RNA molecule comprises a modification selected from the group consisting of a nucleoside modification, an internucleoside modification, a sugar modification, a sugar-internucleoside linkage modification, and combinations thereof, optionally wherein the modification increases resistance in the antisense RNA molecule to degradation by a ribonuclease.

15. The antisense oligomer of claim 1, wherein the antisense oligomer is a morpholino oligomer.

16. A pharmaceutical composition comprising, consisting essentially of, or consisting of the antisense oligomer of claim 1.

17. A method for modulating splicing of an mRNA encoding an MS4A6A protein in cells or tissues, comprising contacting the cells or tissues with the antisense oligomer of claim 1.

* * * * *